US012674799B2

(12) United States Patent
Vogeli et al.

(10) Patent No.: US 12,674,799 B2
(45) Date of Patent: Jul. 7, 2026

(54) CELL-FREE EXPRESSION OF ANTIBODIES, ANTIGEN-BINDING FRAGMENTS THEREOF, AND ANTIBODY DERIVATIVES

(71) Applicant: Northwestern University, Evanston, IL (US)

(72) Inventors: Bastian Vogeli, Evanston, IL (US); Michael Christopher Jewett, Evanston, IL (US); Andrew Colin Hunt, Evanston, IL (US)

(73) Assignee: Northwestern University, Evanston, IL (US)

( * ) Notice: Subject to any disclaimer, the term of this patent is extended or adjusted under 35 U.S.C. 154(b) by 657 days.

(21) Appl. No.: 18/252,773

(22) PCT Filed: Nov. 12, 2021

(86) PCT No.: PCT/US2021/072371
§ 371 (c)(1),
(2) Date: May 12, 2023

(87) PCT Pub. No.: WO2022/104367
PCT Pub. Date: May 19, 2022

(65) Prior Publication Data
US 2024/0027436 A1    Jan. 25, 2024

Related U.S. Application Data

(60) Provisional application No. 63/113,076, filed on Nov. 12, 2020.

(51) Int. Cl.
*G01N 33/535*    (2006.01)
*C07K 16/104*    (2026.01)
*G01N 33/569*    (2006.01)

(52) U.S. Cl.
CPC ......... *G01N 33/535* (2013.01); *C07K 16/104* (2026.01); *G01N 33/56983* (2013.01); *C07K 2317/569* (2013.01); *G01N 2333/165* (2013.01); *G01N 2469/20* (2013.01)

(58) Field of Classification Search
None
See application file for complete search history.

(56) References Cited

FOREIGN PATENT DOCUMENTS

| | | | |
|---|---|---|---|
| EP | 3312278 A1 | 4/2018 |
| JP | 2016002009 A | 1/2016 |
| WO | 2014172631 A2 | 10/2014 |
| WO | 2018025826 A1 | 2/2018 |

(Continued)

OTHER PUBLICATIONS

Cai, Qi, et al. "A simplified and robust protocol for immunoglobulin expression in *E scherichia coli* cell-free protein synthesis systems." Biotechnology progress 31.3 (2015): 823-831.

(Continued)

*Primary Examiner* — Christopher M Gross
(74) *Attorney, Agent, or Firm* — Quarles & Brady LLP

(57) ABSTRACT

The present technology relates to cell-free systems, methods, and kits for expressing proteins in vitro and evaluating the expressed proteins. In particular, the technology relates to cell-free systems, methods, and kits for expressing antibodies, antigen-binding fragment thereof, and antibody derivatives in vitro and evaluating the expressed antibodies, antigen-binding fragment thereof, and antibody derivatives.

20 Claims, 19 Drawing Sheets

Specification includes a Sequence Listing.

Cell-free DNA assembly via Gibson assembly and amplification via PCR    Protein expression via CFPS    PPI characterization via AlphaLISA

| Antibody | Reported ELISA IC50 (µg/mL) | Measured AlphaLISA IC50 (µg/mL) | Measured AlphaLISA IC50 95% CI (µg/mL) |
|---|---|---|---|
| nAb1 | 1.47 | 0.69 | 0.43 to 1.10 |
| nAb2 | 0.55 | 0.63 | 0.50 to 0.79 |
| nAb3 | 0.13 | 0.47 | 0.35 to 0.82 |
| nAb4 | 0.09 | 0.14 | 0.14 to 0.15 |

(56) References Cited

FOREIGN PATENT DOCUMENTS

| | | |
|---|---|---|
| WO | 2018112237 A1 | 6/2018 |
| WO | 2020097385 A1 | 5/2020 |

OTHER PUBLICATIONS

Hunt, Andrew C., et al. "A high-throughput, automated, cell-free expression and screening platform for antibody discovery." bioRxiv (2021): 2021-11.

Martin, Rey W., et al. "Development of a CHO-based cell-free platform for synthesis of active monoclonal antibodies." ACS synthetic biology 6.7 (2017): 1370-1379.

Murakami, Satoshi, Rena Matsumoto, and Takashi Kanamori. "Constructive approach for synthesis of a functional IgG using a reconstituted cell-free protein synthesis system." Scientific Reports 9.1 (2019): 671.

Oh, In-Seok, et al. "Cell-free production of functional antibody fragments." Bioprocess and biosystems engineering 33 (2010): 127-132.

Ojima-Kato, Teruyo, et al. "Rapid generation of monoclonal antibodies from single B cells by ecobody technology." Antibodies 7.4 (2018): 38.

Ojima-Kato, Teruyo, Satomi Nagai, and Hideo Nakano. "Ecobody technology: rapid monoclonal antibody screening method from single B cells using cell-free protein synthesis for antigen-binding fragment formation." Scientific Reports 7.1 (2017): 13979.

Sierecki, Emma, et al. "A cell-free approach to accelerate the study of protein-protein interactions in vitro." Interface Focus 3.5 (2013): 20130018.

Sierecki, Emma, et al. "Rapid mapping of interactions between human SNX-BAR proteins measured in vitro by AlphaScreen and single-molecule spectroscopy." Molecular & Cellular Proteomics 13.9 (2014): 2233-2245.

Sun, Zachary Z., et al. "Linear DNA for rapid prototyping of synthetic biological circuits in an *Escherichia coli* based TX-TL cell-free system." ACS synthetic biology 3.6 (2014): 387-397.

Thoring, Lena, et al. "High-yield production of "difficult-to-express" proteins in a continuous exchange cell-free system based on CHO cell lysates." Scientific reports 7.1 (2017): 11710.

Ryabova, Lyubov A., et al. "Functional antibody production using cell-free translation: effects of protein disulfide isomerase and chaperones." Nature biotechnology 15.1 (1997): 79-84.

International Search Report in PCT/US2021/072371; received on Feb. 1, 2022.

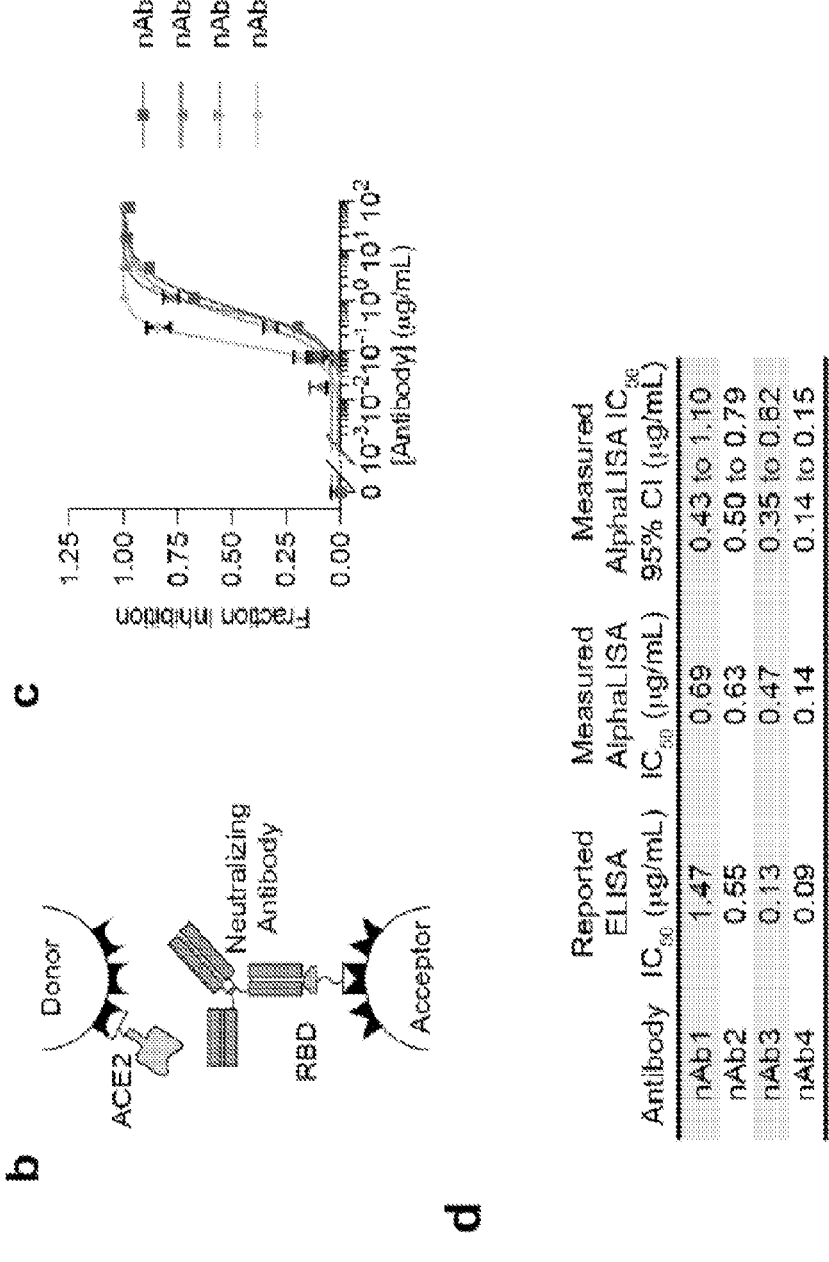
Figure 1b-d

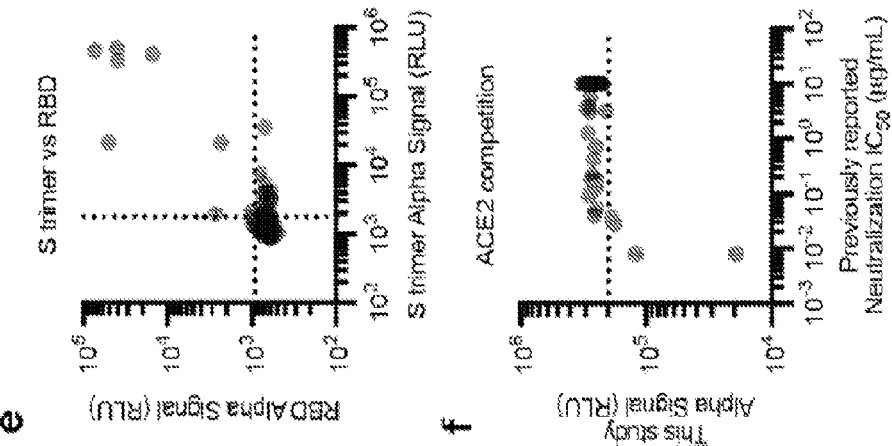
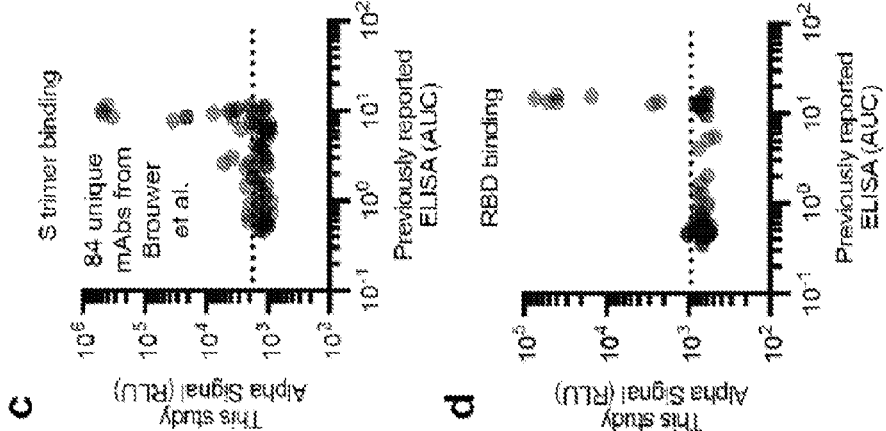
Figure 2c-f

Figure 3b-c
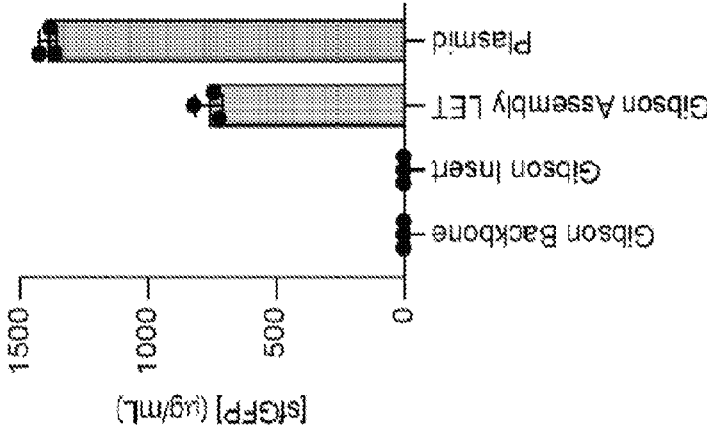
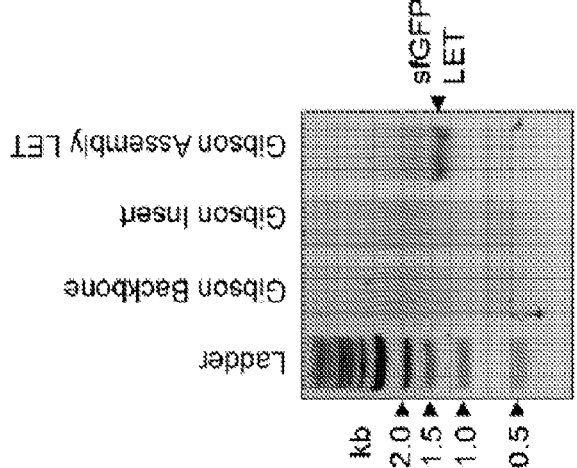

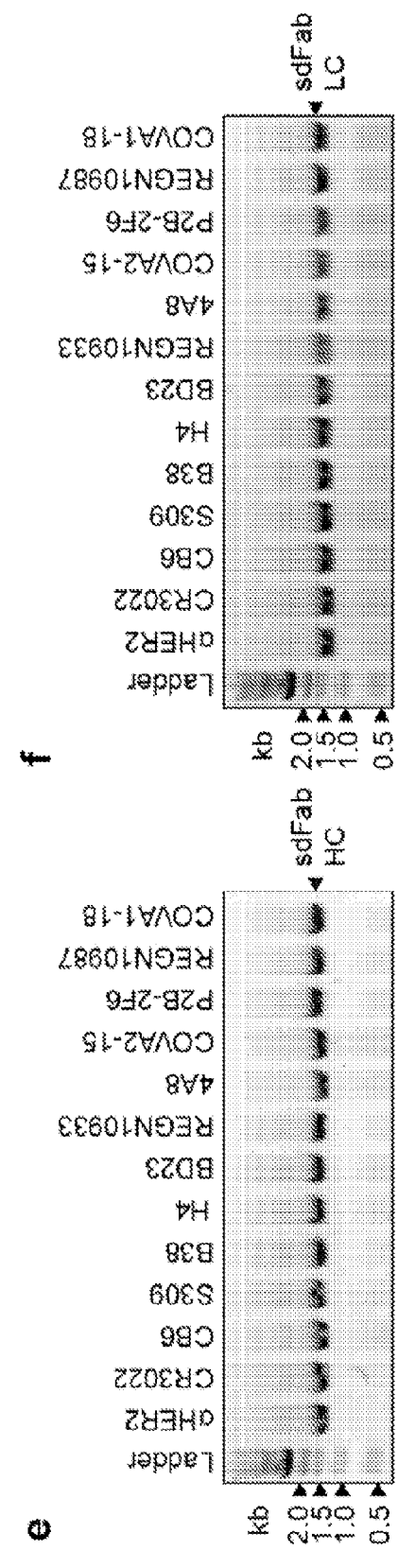
Figure 3e-f

Figure 4a-c
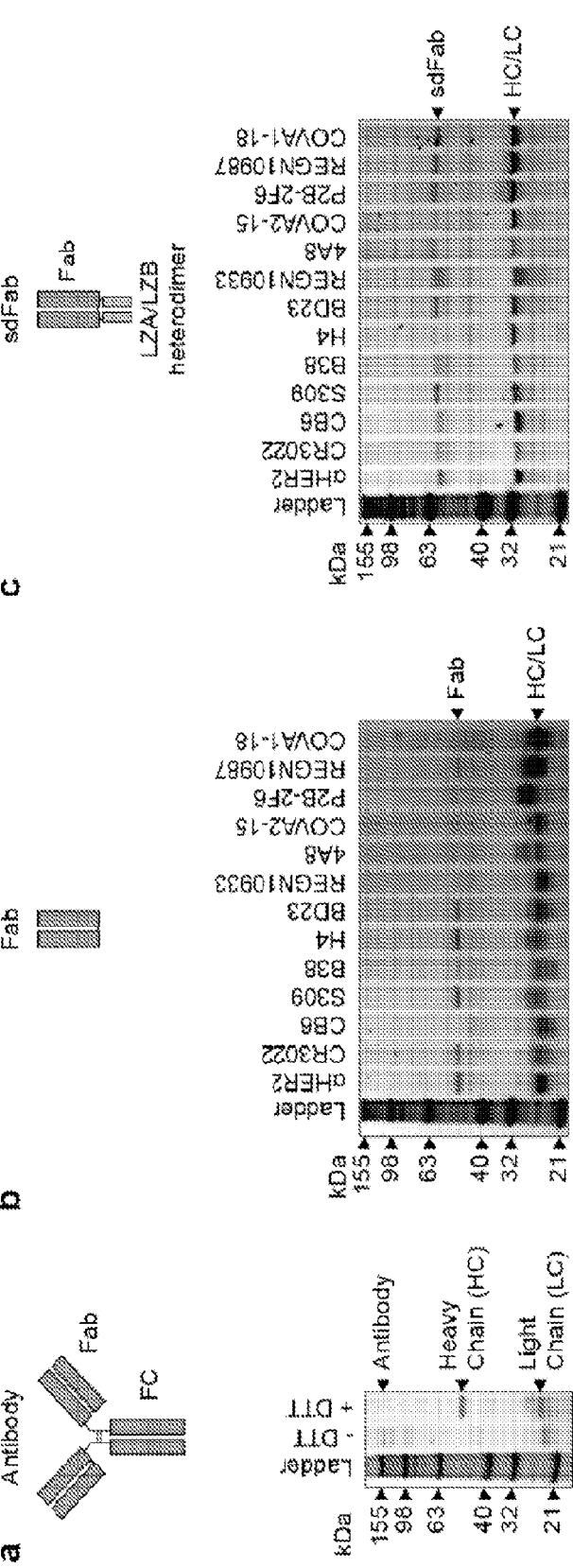

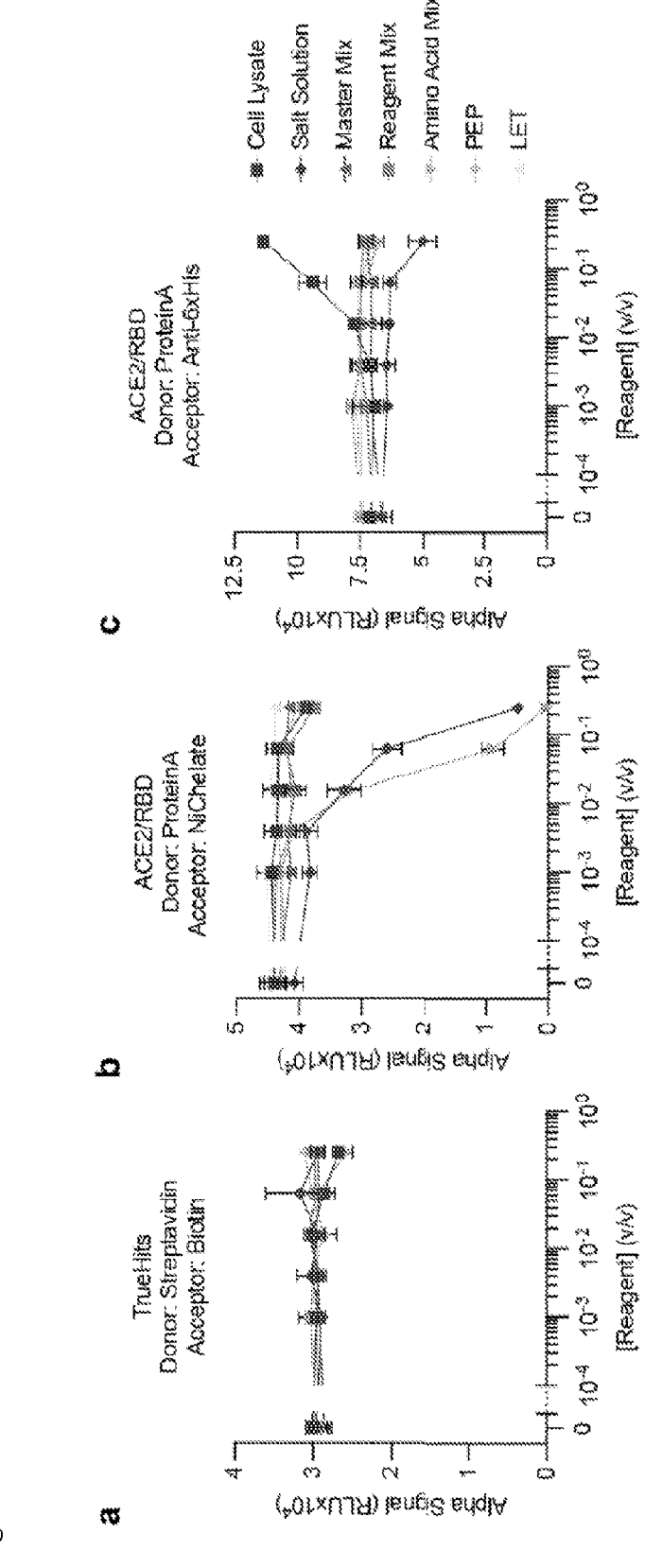
Figure 5a-c

Figure 5d-f
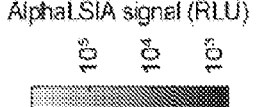
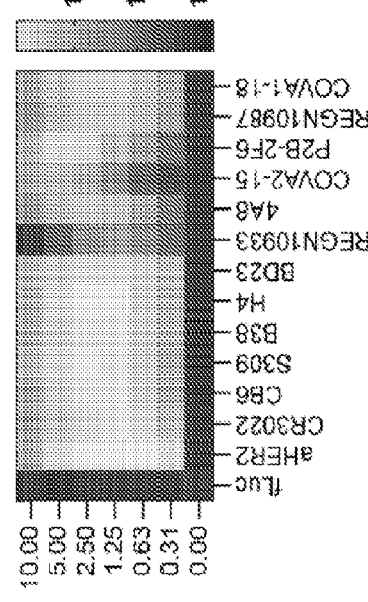
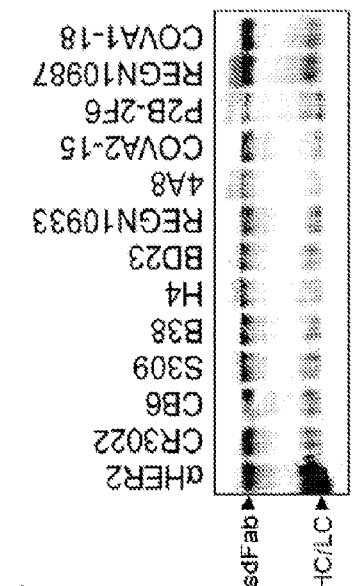

Figure 6a-d
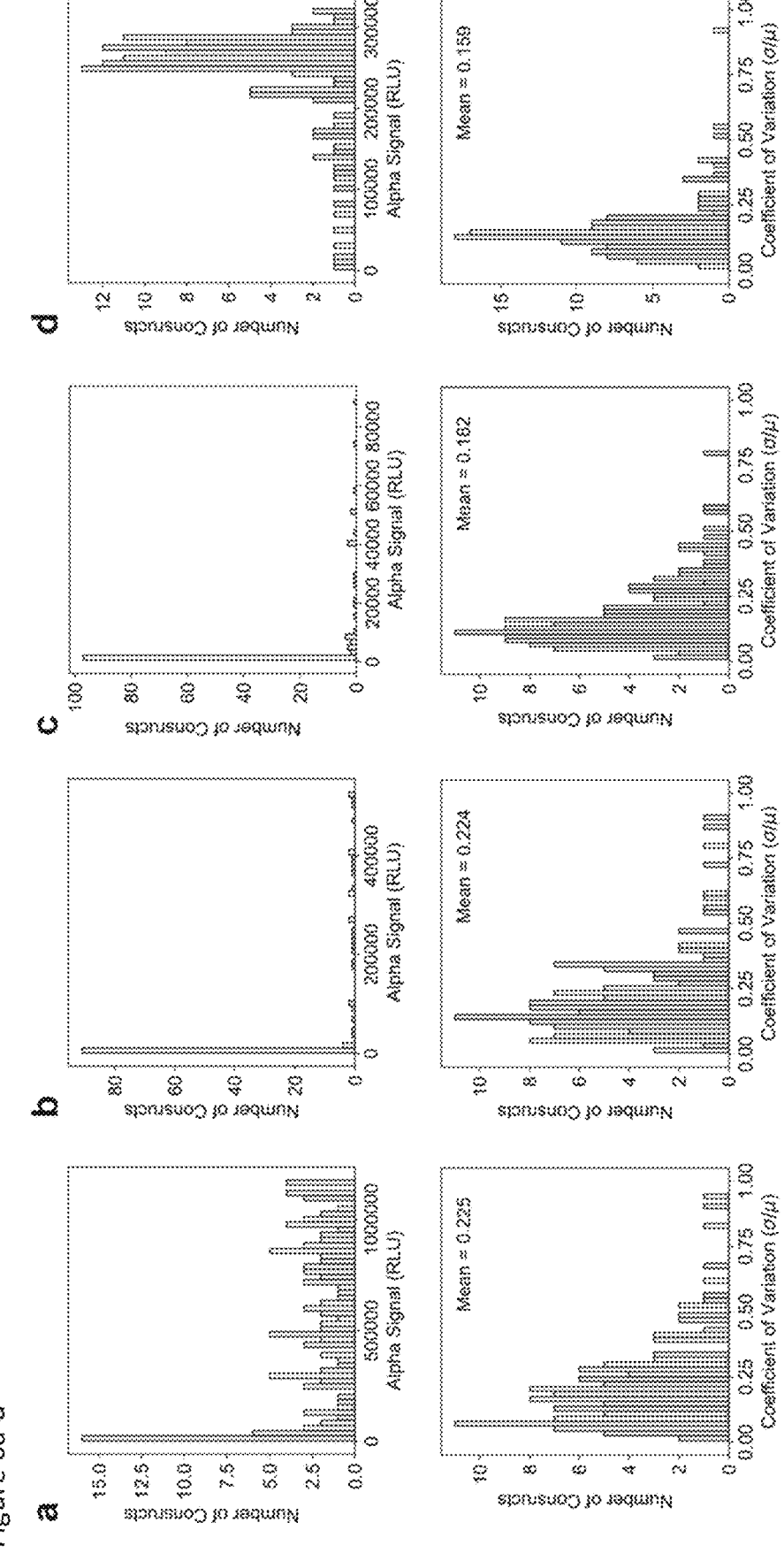

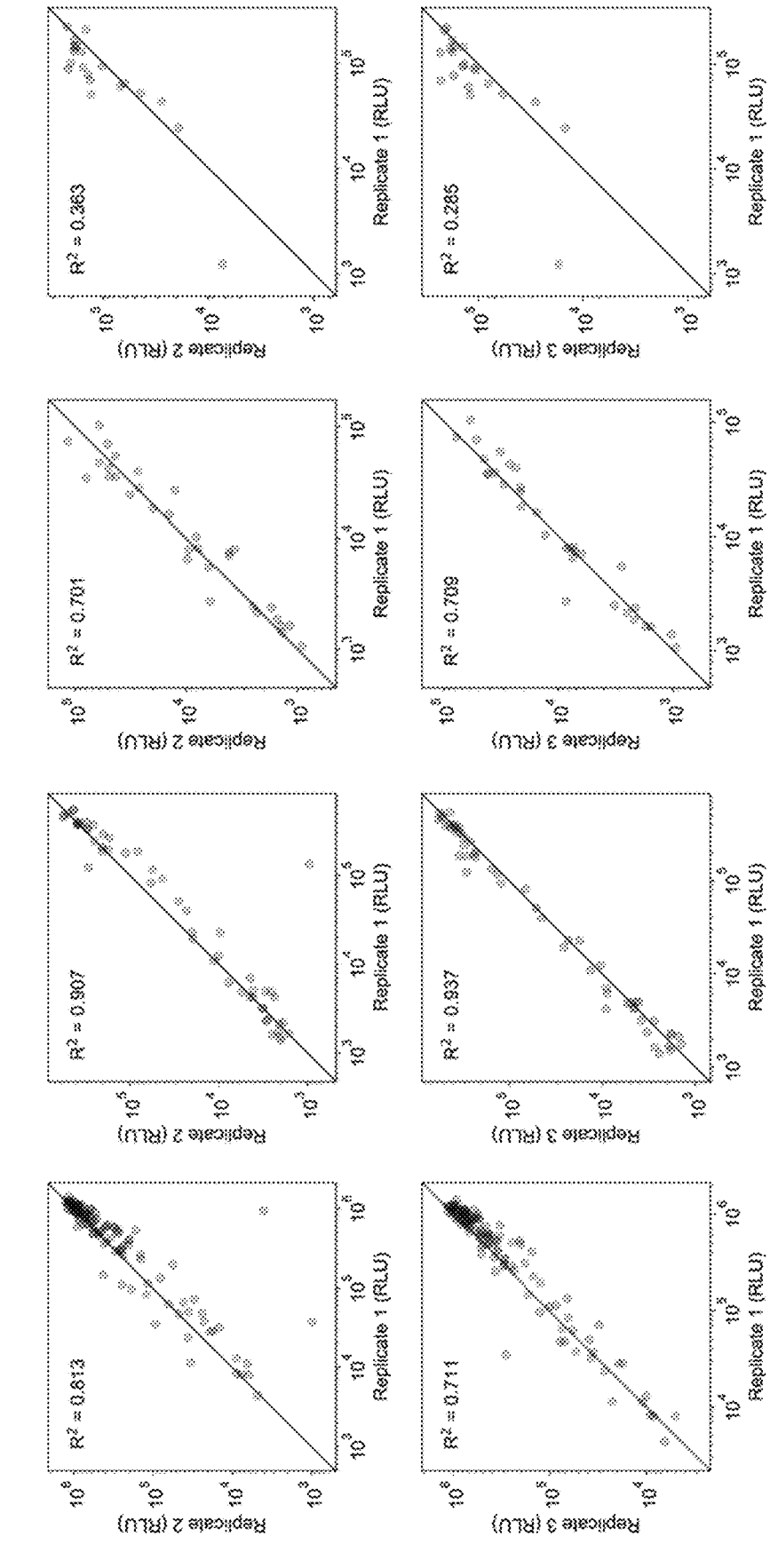
Figure 6a-d, continued

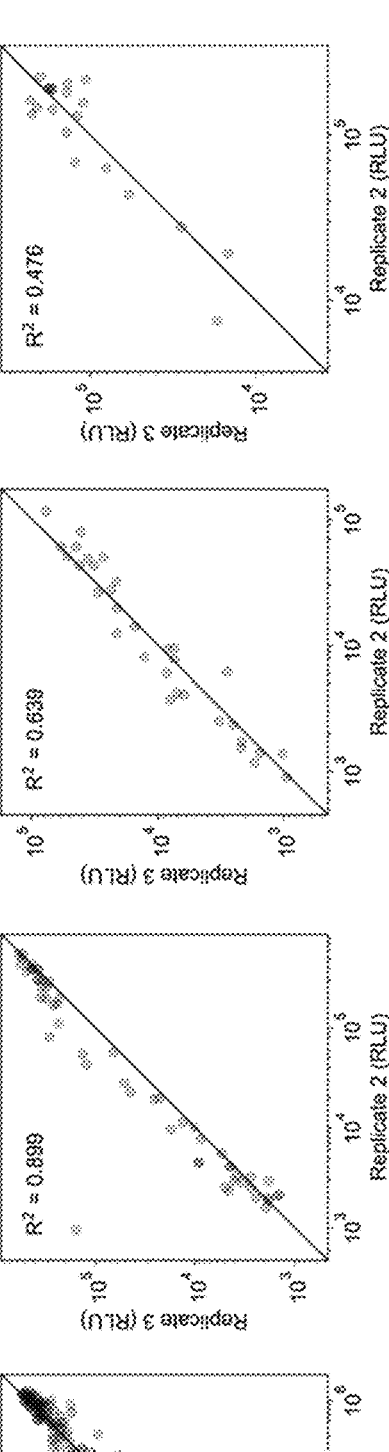
Figure 6a-d, continued

Figure 7a-b
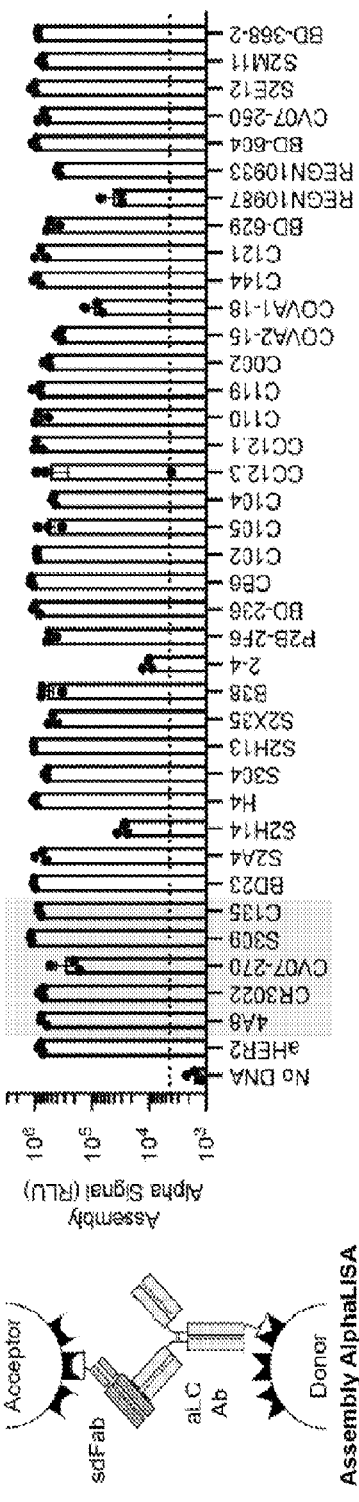

Figure 7c-d
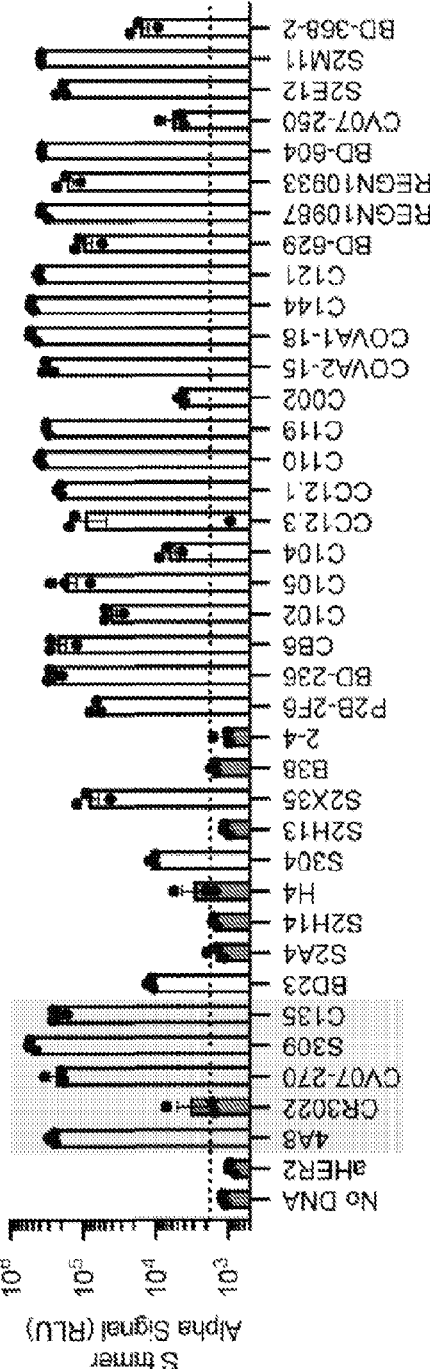
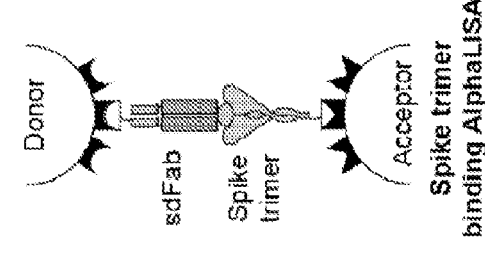

Figure 7e-f
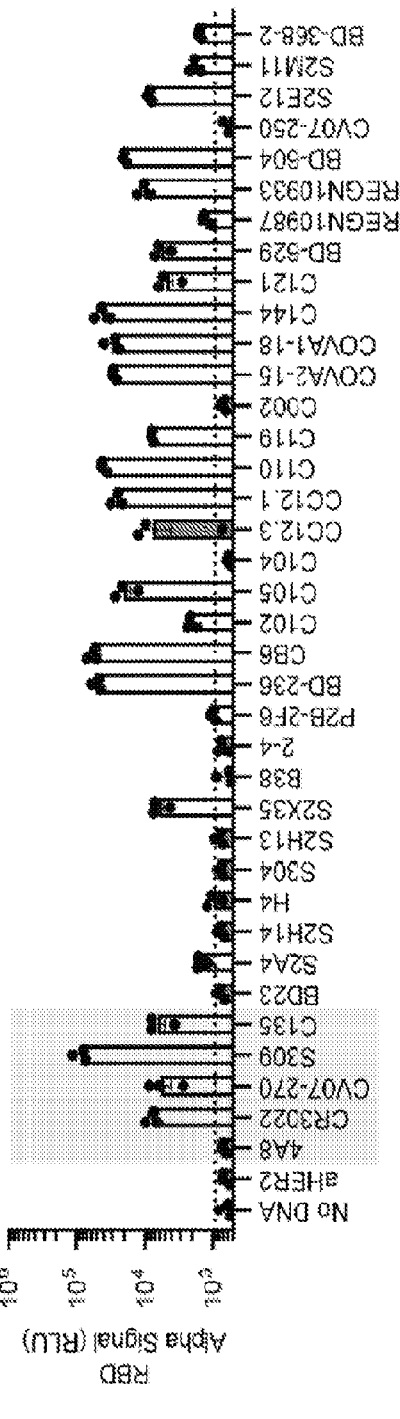
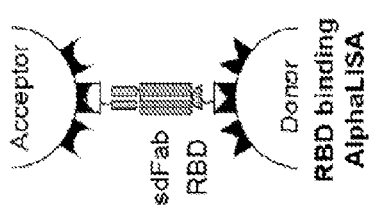

Figure 7g-h
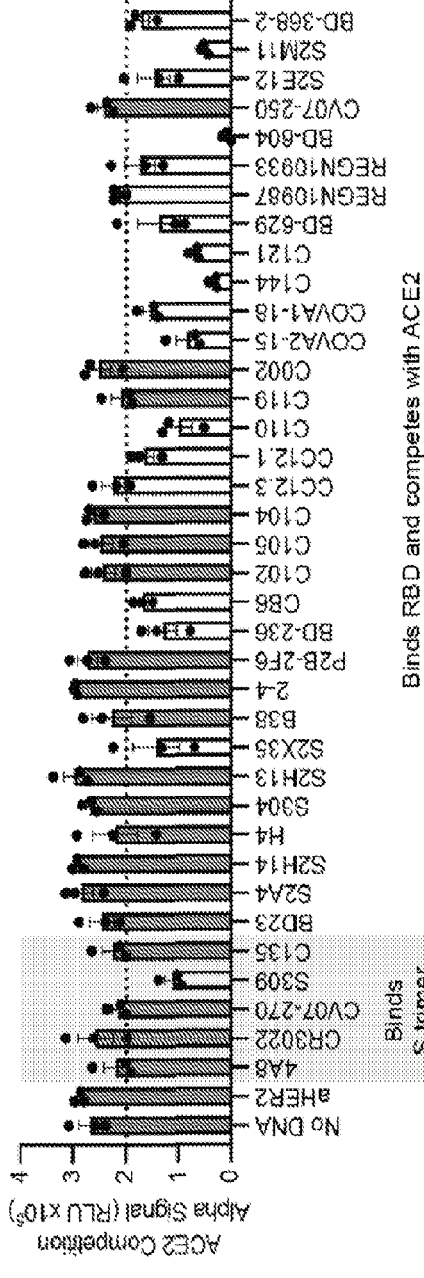
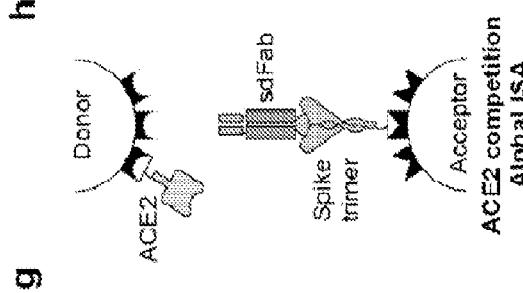

SEQUENCE LISTING

```
<160> NUMBER OF SEQ ID NOS: 29

<210> SEQ ID NO 1
<211> LENGTH: 12
<212> TYPE: PRT
<213> ORGANISM: Artificial Sequence
<220> FEATURE:
<223> OTHER INFORMATION: Synthetic- Tobacco Etch Virus (TEV) protease
      cleavage site

<400> SEQUENCE: 1

Met Glu Lys Lys Ile Glu Asn Leu Tyr Phe Gln Ser
1               5                   10

<210> SEQ ID NO 2
<211> LENGTH: 36
<212> TYPE: DNA
<213> ORGANISM: Artificial Sequence
<220> FEATURE:
<223> OTHER INFORMATION: Synthetic- Tobacco Etch Virus (TEV) protease
      cleavage site DNA sequence

<400> SEQUENCE: 2
atggagaaaa aaatcgaaaa cctgtacttc cagagc                                    36

<210> SEQ ID NO 3
<211> LENGTH: 31
<212> TYPE: PRT
<213> ORGANISM: Artificial Sequence
<220> FEATURE:
<223> OTHER INFORMATION: Synthetic- LZA heterodimer subunit

<400> SEQUENCE: 3

Ala Gln Leu Glu Lys Glu Leu Gln Ala Leu Glu Lys Glu Asn Ala Gln
1               5                   10                  15

Leu Glu Trp Glu Leu Gln Ala Leu Glu Lys Glu Leu Ala Gln Lys
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic- LZB heterodimer subunit

<400> SEQUENCE: 4

Ala Gln Leu Lys Lys Lys Leu Gln Ala Leu Lys Lys Lys Asn Ala Gln
1               5                   10                  15

Leu Lys Trp Lys Leu Gln Ala Leu Lys Lys Lys Leu Ala Gln Lys
            20                  25                  30
```

```
<210> SEQ ID NO 5
<211> LENGTH: 4
<212> TYPE: PRT
<213> ORGANISM: Artificial Sequence
<220> FEATURE:
<223> OTHER INFORMATION: Synthetic- SKIK tag

<400> SEQUENCE: 5

Ser Lys Ile Lys
1

<210> SEQ ID NO 6
<211> LENGTH: 163
<212> TYPE: PRT
<213> ORGANISM: Artificial Sequence
<220> FEATURE:
<223> OTHER INFORMATION: Synthetic- sdFab heavy chain constant strepII
      tagged

<400> SEQUENCE: 6

Met Glu Lys Lys Ile Glu Asn Leu Tyr Phe Gln Ser Ala Ser Thr Lys
1               5                   10                  15

Gly Pro Ser Val Phe Pro Leu Ala Pro Ser Ser Lys Ser Thr Ser Gly
            20                  25                  30

Gly Thr Ala Ala Leu Gly Cys Leu Val Lys Asp Tyr Phe Pro Glu Pro
        35                  40                  45

Val Thr Val Ser Trp Asn Ser Gly Ala Leu Thr Ser Gly Val His Thr
    50                  55                  60

Phe Pro Ala Val Leu Gln Ser Ser Gly Leu Tyr Ser Leu Ser Ser Val
65                  70                  75                  80

Val Thr Val Pro Ser Ser Ser Leu Gly Thr Gln Thr Tyr Ile Cys Asn
                85                  90                  95

Val Asn His Lys Pro Ser Asn Thr Lys Val Asp Lys Lys Val Glu Pro
                100                 105                 110

Lys Ser Cys Gly Gly Gly Gly Ser Ala Gln Leu Glu Lys Glu Leu Gln
        115                 120                 125

Ala Leu Glu Lys Glu Asn Ala Gln Leu Glu Trp Glu Leu Gln Ala Leu
    130                 135                 140

Glu Lys Glu Leu Ala Gln Lys Gly Ser Ser Ala Trp Ser His Pro Gln
145                 150                 155                 160

Phe Glu Lys

<210> SEQ ID NO 7
<211> LENGTH: 155
<212> TYPE: PRT
<213> ORGANISM: Artificial Sequence
<220> FEATURE:
<223> OTHER INFORMATION: Synthetic- sdFab light chain kappa

<400> SEQUENCE: 7

Met Glu Lys Lys Ile Glu Asn Leu Tyr Phe Gln Ser Arg Thr Val Ala
1               5                   10                  15

Ala Pro Ser Val Phe Ile Phe Pro Pro Ser Asp Glu Gln Leu Lys Ser
            20                  25                  30

Gly Thr Ala Ser Val Val Cys Leu Leu Asn Asn Phe Tyr Pro Arg Glu
        35                  40                  45

Ala Lys Val Gln Trp Lys Val Asp Asn Ala Leu Gln Ser Gly Asn Ser
    50                  55                  60

Gln Glu Ser Val Thr Glu Gln Asp Ser Lys Asp Ser Thr Tyr Ser Leu
65                  70                  75                  80
```

```
Ser Ser Thr Leu Thr Leu Ser Lys Ala Asp Tyr Glu Lys His Lys Val
                85              90              95

Tyr Ala Cys Glu Val Thr His Gln Gly Leu Ser Ser Pro Val Thr Lys
            100             105             110

Ser Phe Asn Arg Gly Glu Cys Gly Gly Gly Ser Ala Gln Leu Lys
        115             120             125

Lys Lys Leu Gln Ala Leu Lys Lys Lys Asn Ala Gln Leu Lys Trp Lys
    130             135             140

Leu Gln Ala Leu Lys Lys Lys Leu Ala Gln Lys
145             150             155

<210> SEQ ID NO 8
<211> LENGTH: 154
<212> TYPE: PRT
<213> ORGANISM: Artificial Sequence
<220> FEATURE:
<223> OTHER INFORMATION: Synthetic- sdFab light chain lambda 1

<400> SEQUENCE: 8

Met Glu Lys Lys Ile Glu Asn Leu Tyr Phe Gln Ser Gly Gln Pro Lys
1               5               10              15

Ala Asn Pro Thr Val Thr Leu Phe Pro Pro Ser Ser Glu Glu Leu Gln
            20              25              30

Ala Asn Lys Ala Thr Leu Val Cys Leu Ile Ser Asp Phe Tyr Pro Gly
        35              40              45

Ala Val Thr Val Ala Trp Lys Ala Asp Gly Ser Pro Val Lys Ala Gly
    50              55              60

Val Glu Thr Thr Lys Pro Ser Lys Gln Ser Asn Asn Lys Tyr Ala Ala
65              70              75              80

Ser Ser Tyr Leu Ser Leu Thr Pro Glu Gln Trp Lys Ser His Arg Ser
                85              90              95

Tyr Ser Cys Gln Val Thr His Glu Gly Ser Thr Val Glu Lys Thr Val
            100             105             110

Ala Pro Thr Glu Cys Ser Gly Gly Gly Ser Ala Gln Leu Lys Lys
        115             120             125

Lys Leu Gln Ala Leu Lys Lys Lys Asn Ala Gln Leu Lys Trp Lys Leu
    130             135             140

Gln Ala Leu Lys Lys Lys Leu Ala Gln Lys
145             150

<210> SEQ ID NO 9
<211> LENGTH: 30
<212> TYPE: DNA
<213> ORGANISM: Artificial Sequence
<220> FEATURE:
<223> OTHER INFORMATION: Synthetic- pJL1 5' Gibson

<400> SEQUENCE: 9
tttgtttaac tttaagaagg agatatacat                                  30

<210> SEQ ID NO 10
<211> LENGTH: 30
<212> TYPE: DNA
<213> ORGANISM: Artificial Sequence
<220> FEATURE:
<223> OTHER INFORMATION: Synthetic- pJL1 3' Gibson

<400> SEQUENCE: 10
gtcgaccggc tgctaacaaa gcccgaaagg                                  30
```

-continued

```
<210> SEQ ID NO 11
<211> LENGTH: 39
<212> TYPE: DNA
<213> ORGANISM: Artificial Sequence
<220> FEATURE:
<223> OTHER INFORMATION: Synthetic- Human IgG1 heavy chain constant 5'
      Gibson

<400> SEQUENCE: 11
gcgtcaacaa aaggtccttc agttttccca ttagccct                      39

<210> SEQ ID NO 12
<211> LENGTH: 39
<212> TYPE: DNA
<213> ORGANISM: Artificial Sequence
<220> FEATURE:
<223> OTHER INFORMATION: Synthetic- Human Ig light chain kappa 5' Gibson

<400> SEQUENCE: 12
cgcacggtcg cggcgccgtc tgtctttatt tttcctcct                     39

<210> SEQ ID NO 13
<211> LENGTH: 39
<212> TYPE: DNA
<213> ORGANISM: Artificial Sequence
<220> FEATURE:
<223> OTHER INFORMATION: Synthetic- Human Ig light chain lambda 5'
      Gibson

<400> SEQUENCE: 13
ggccaaccca aagcaaaccc aactgtcact ttgttcccg                     39

<210> SEQ ID NO 14
<211> LENGTH: 1763
<212> TYPE: DNA
<213> ORGANISM: Artificial Sequence
<220> FEATURE:
<223> OTHER INFORMATION: Synthetic- Linear pJL1 plasmid backbone
      (Addgene plasmid # 69496)

<400> SEQUENCE: 14
gtcgaccggc tgctaacaaa gcccgaaagg aagctgagtt ggctgctgcc accgctgagc      60
aataactagc ataacccctt ggggcctcta acgggtctt gaggggtttt ttgctgaaag       120
ccaattctga ttagaaaaac tcatcgagca tcaaatgaaa ctgcaattta ttcatatcag      180
gattatcaat accatatttt tgaaaaagcc gtttctgtaa tgaaggagaa aactcaccga      240
ggcagttcca taggatggca agatcctggt atcggtctgc gattccgact cgtccaacat      300
caatacaacc tattaatttc ccctcgtcaa aaataaggtt atcaagtgag aaatcaccat      360
gagtgacgac tgaatccggt gagaatggca aaagcttatg catttctttc cagacttgtt      420
caacaggcca gccattacgc tcgtcatcaa aatcactcgc atcaaccaaa ccgttattca      480
ttcgtgattg cgcctgagcg agacgaaata cgcgatcgct gttaaaagga caattacaaa      540
caggaatcga atgcaaccgg cgcaggaaca ctgccagcgc atcaacaata ttttcacctg      600
aatcaggata ttcttctaat acctggaatg ctgtttttcc ggggatcgca gtggtgagta      660
accatgcatc atcaggagta cggataaaat gcttgatggt cggaagaggc ataaattccg      720
tcagccagtt tagtctgacc atctcatctg taacatcatt ggcaacgcta cctttgccat      780
gtttcagaaa caactctggc gcatcgggct tcccatacaa tcgatagatt gtcgcacctg      840
attgcccgac attatcgcga gcccatttat acccatataa atcagcatcc atgttggaat      900
```

-continued

```
ttaatcgcgg cttcgagcaa gacgtttccc gttgaatatg gctcataaca ccccttgtat      960
tactgtttat gtaagcagac agtttttattg ttcatgatga tatatttttta tcttgtgcaa    1020 tgtaacatca gagattttga gacacaacgt gagatcaaag gatcttcttg agatcctttt     1080
tttctgcgcg taatctgctg cttgcaaaca aaaaaaccac cgctaccagc ggtggtttgt     1140
ttgccggatc aagagctacc aactcttttt ccgaaggtaa ctggcttcag cagagcgcag     1200
ataccaaata ctgttcttct agtgtagccg tagttaggcc accacttcaa gaactctgta     1260
gcaccgccta catacctcgc tctgctaatc ctgttaccag tggctgctgc cagtggcgat     1320
aagtcgtgtc ttaccgggtt ggactcaaga cgatagttac cggataaggc gcagcggtcg     1380
ggctgaacgg ggggttcgtg cacacagccc agcttggagc gaacgaccta caccgaactg     1440
agatacctac agcgtgagct atgagaaagc gccacgcttc ccgaagggag aaaggcggac     1500
aggtatccgg taagcggcag ggtcggaaca ggagagcgca cgagggagct tccaggggga     1560
aacgcctggt atctttatag tcctgtcggg tttcgccacc tctgacttga gcgtcgattt     1620
ttgtgatgct cgtcaggggg gcggagccta tggaaaaacg ccagcaacgc gatcccgcga     1680
aattaatacg actcactata gggagaccac aacggtttcc ctctagaaat aattttgttt     1740
aactttaaga aggagatata cat                                             1763
```

```
<210> SEQ ID NO 15
<211> LENGTH: 15
<212> TYPE: DNA
<213> ORGANISM: Artificial Sequence
<220> FEATURE:
<223> OTHER INFORMATION: Synthetic- pJL1_F

<400> SEQUENCE: 15
gtcgaccggc tgcta                                                         15
```

```
<210> SEQ ID NO 16
<211> LENGTH: 40
<212> TYPE: DNA
<213> ORGANISM: Artificial Sequence
<220> FEATURE:
<223> OTHER INFORMATION: Synthetic- pJL1_R

<400> SEQUENCE: 16
atgtatatct ccttcttaaa gttaaacaaa attatttcta                              40
```

```
<210> SEQ ID NO 17
<211> LENGTH: 486
<212> TYPE: DNA
<213> ORGANISM: Artificial Sequence
<220> FEATURE:
<223> OTHER INFORMATION: Synthetic- Linear sdFab heavy chain constant
      strepII tagged

<400> SEQUENCE: 17
gcgtcaacaa aaggtccttc agtttttccca ttagcccctt cttctaagtc aactagtggc      60
ggtactgccg ctcttgggtg tttggttaaa gattacttcc cagaaccggt tacggtctcg     120
tggaactctg gtgcactgac atcgggcgta catacatttc ccgcagtttt gcagtcttcg     180
ggactgtatt ctctttcatc ggtggttaca gtccctagct cttccctggg tacacagacc     240
tacatttgta atgttaatca taagccgagt aatactaagg tggataaaaa ggtggaaccg     300
aagtcttgtg gtggtggcgg gtcagctcaa ctggagaagg agttacaggc actggaaaaa     360
gagaatgctc aacttgagtg ggaattacag gcgttagaaa aagaactggc ccagaagggt     420
```

-continued

```
tctagcgcat ggtcacatcc ccagttcgaa aaataagtcg accggctgct aacaaagccc    480
gaaagg                                                               486

<210> SEQ ID NO 18
<211> LENGTH: 27
<212> TYPE: DNA
<213> ORGANISM: Artificial Sequence
<220> FEATURE:
<223> OTHER INFORMATION: Synthetic- IgGC_F

<400> SEQUENCE: 18
gcgtcaacaa aaggtccttc agttttc                                         27

<210> SEQ ID NO 19
<211> LENGTH: 22
<212> TYPE: DNA
<213> ORGANISM: Artificial Sequence
<220> FEATURE:
<223> OTHER INFORMATION: Synthetic- pJL1_3'Gib_R

<400> SEQUENCE: 19
cctttcgggc tttgttagca gc                                              22

<210> SEQ ID NO 20
<211> LENGTH: 462
<212> TYPE: DNA
<213> ORGANISM: Artificial Sequence
<220> FEATURE:
<223> OTHER INFORMATION: Synthetic- Linear sdFab light chain kappa
      constant

<400> SEQUENCE: 20
cgcacggtcg cggcgccgtc tgtctttatt tttcctcctt ctgatgaaca gcttaaatct    60
gggacagctt ctgttgtatg tttattaaac aacttttacc cgcgtgaggc aaaagttcaa    120
tggaaggtag acaacgcact gcaaagcgga aattcgcagg agtcagttac cgaacaggat    180
tccaaggata gtacctactc cttaagttca acattaaccc tgtcaaaggc ggactatgaa    240
aaacataagg tatatgcctg cgaagtaact catcagggct tatcatcccc agttacaaaa    300
tctttcaacc gtggagaatg cggcggcgga ggtagcgcgc agcttaagaa aaaattgcaa    360
gcccttaaaa aaaaaatgc ccaacttaaa tggaagctgc aagccttaaa aaagaaattg    420
gcgcagaagt aagtcgaccg gctgctaaca agcccgaaa gg                         462

<210> SEQ ID NO 21
<211> LENGTH: 15
<212> TYPE: DNA
<213> ORGANISM: Artificial Sequence
<220> FEATURE:
<223> OTHER INFORMATION: Synthetic- kLC_F

<400> SEQUENCE: 21
tcgcggcgcc gtctg                                                      15

<210> SEQ ID NO 22
<211> LENGTH: 22
<212> TYPE: DNA
<213> ORGANISM: Artificial Sequence
<220> FEATURE:
<223> OTHER INFORMATION: Synthetic- pJL1_3'Gib_R

<400> SEQUENCE: 22
cctttcgggc tttgttagca gc                                              22
```

<210> SEQ ID NO 23
<211> LENGTH: 459
<212> TYPE: DNA
<213> ORGANISM: Artificial Sequence
<220> FEATURE:
<223> OTHER INFORMATION: Synthetic- Linear sdFab light chain lambda 1
      constant

<400> SEQUENCE: 23
ggccaaccca aagcaaaccc aactgtcact ttgttcccgc cctcaagcga ggaacttcag        60
gctaataagg ccacgcttgt ttgcctgatc tcagactttt atcccggtgc cgtaacagtg       120
gcttggaagg cagatggttc gccggtcaaa gcgggcgtgg aaactacaaa gccatcgaaa       180
cagtcaaaca ataaatatgc ggcatcaagt tacttgagcc ttaccccaga acagtggaag       240
tcacaccgct cgtacagttg tcaagttaca cacgagggaa gtacagttga aaagaccgtt       300
gccccaactg aatgttcagg cggtggtggc tcagcgcagt aaagaaaaa actgcaggct        360 ttgaagaaaa agaatgctca attaaagtgg aaattgcagg cgttgaagaa gaaacttgcg       420
cagaagtaag tcgaccggct gctaacaaag cccgaaagg                              459

<210> SEQ ID NO 24
<211> LENGTH: 18
<212> TYPE: DNA
<213> ORGANISM: Artificial Sequence
<220> FEATURE:
<223> OTHER INFORMATION: Synthetic- 1LC_F

<400> SEQUENCE: 24
ggccaaccca aagcaaac                                                      18

<210> SEQ ID NO 25
<211> LENGTH: 22
<212> TYPE: DNA
<213> ORGANISM: Artificial Sequence
<220> FEATURE:
<223> OTHER INFORMATION: Synthetic- pJL1_3'Gib_R

<400> SEQUENCE: 25
cctttcgggc tttgttagca gc                                                 22

<210> SEQ ID NO 26
<211> LENGTH: 22
<212> TYPE: DNA
<213> ORGANISM: Artificial Sequence
<220> FEATURE:
<223> OTHER INFORMATION: Synthetic- pJL1_LET_F

<400> SEQUENCE: 26
ctgagatacc tacagcgtga gc                                                 22

<210> SEQ ID NO 27
<211> LENGTH: 26
<212> TYPE: DNA
<213> ORGANISM: Artificial Sequence
<220> FEATURE:
<223> OTHER INFORMATION: Synthetic- pJL1_LET_R

<400> SEQUENCE: 27
cgtcactcat ggtgatttct cacttg                                             26

<210> SEQ ID NO 28
<211> LENGTH: 1689

<212> TYPE: DNA
<213> ORGANISM: Artificial Sequence
<220> FEATURE:
<223> OTHER INFORMATION: Synthetic- P. pyralis luciferase containing a
      c-terminal strepII tag

<400> SEQUENCE: 28

```
atggaagacg ctaagaacat taagaaggga cctgctccat tctacccct cgaagacggc        60 actgcaggtg agcagcttca taaagcgatg aagcgttatg cgttagttcc tggcacgatc       120
gccttcactg acgcgcacat cgaagtcaat atcacctacg ctgaatactt tgagatgagt       180
gtgcgtctgg cggaagccat gaagcgttat ggccttaaca cgaaccaccg catcgttgtt       240
tgtagcgaga attccttaca attcttcatg cccgtccttg cgcgctgtt tattggtgtg        300 gccgttgcac cagccaatga catctataat gagcgcgagt tgttgaactc catgaacatt       360
tctcaaccaa cagtggtgtt cgtttcaaag aaaggcttac agaaaatctt aaacgttcaa       420
aagaaactgc cgattatcca gaagatcatc attatggata gtaagactga ctaccagggc       480
ttccagtcaa tgtatacatt cgtgacgagt cacctgcccc cgggttttaa cgagtacgac       540
tttgtcccag agagctttga tcgcgacaag accatcgccc tcattatgaa tagcagtggt       600
tcgacgggta gcccaaaggg agtggccctg ccccatcgta ccgcgtgcgt ccgtttctcc       660
catgcccgcg acccaatttt cggcaatcaa atcatccccg acacggcaat cttgtcggtc       720
gtcccgtttc accatggctt tggaatgttt acgacactcg gttacctcat ctgcggtttc       780
cgcgtcgttc tgatgtatcg cttcgaggaa gagttgttct tacgttcgct tcaggactac       840
aagattcaat ccgcccttct ggtccccact ttgttcagtt tctttgctaa gagcaccta      900 attgataagt atgacctctc caacttacac gagattgcga gcggtggtgc tccctcagc       960 aaagaggttg gagaggcggt tgctaagcgt tttcatctgc ccggtatccg tcaaggttac      1020
ggcctcaccg aaaccacttc tgccattctt atcactccgg aaggtgacga taagcctggg      1080
gcagtgggta agttgtacc cttcttcgag gctaaggttg tggatttaga tacggggaag      1140
accttaggtg tgaaccagcg cggtgaactg tgcgttcgcg gtccgatgat tatgtcgggt      1200
tatgttaatg accccgaggc tacgaacgcg cttatcgata aggacggttg gcttcattcc      1260
ggcgacatcg cttactggga tgaggatgag cacttcttca tcgttgaccg tctgaagagt      1320
ctcatcaagt ataagggatg tcaagtcgct ccggcagagt tagagagcat cttactccag      1380
caccctaata tcttcgatgc tggggttgcc gggctcccag cgacgatgc cggcgagctg      1440 ccggcggcgg tagttgtttt agagcatggc aagaccatga ccgaaaagga gattgtagac      1500
tacgtcgcga gtcaagtaac cacagcgaag aagctccgcg gtggagtggt ctttgttgac      1560
gaggtgccta aaggcctgac gggcaaactt gacgcgcgta gatccgtga gatcctcatc      1620 aaagcgaaga agggtgggaa gagtaagctg gggagttcag gttggtccca cccgcaattt      1680
gagaagtga                                                              1689
```

<210> SEQ ID NO 29
<211> LENGTH: 21
<212> TYPE: PRT
<213> ORGANISM: Artificial Sequence
<220> FEATURE:
<223> OTHER INFORMATION: Synthetic- TEV cleavable his tag

```
<400> SEQUENCE: 29

Gly Ser Glu Asn Leu Tyr Phe Gln Ser Gly Ser His His His His His
1               5                   10                  15

His His His His His
            20
```

CELL-FREE EXPRESSION OF ANTIBODIES, ANTIGEN-BINDING FRAGMENTS THEREOF, AND ANTIBODY DERIVATIVES

CROSS-REFERENCE TO RELATED APPLICATIONS

This application is the U.S. National Stage of PCT/US2021/072371 with international filing date of Nov. 12, 2021, which claims the benefit of U.S. Application No. 63/113,076 filed Nov. 12, 2020. The content of each of the above-referenced applications is incorporated herein by reference in its entirety.

SEQUENCE LISTING

A Sequence Listing accompanies this application and is submitted as an ASCII text file of the sequence listing named "702581_2065_ST25.txt" which is 16,880 bytes in size and was created on Nov. 10, 2021. The sequence listing is electronically submitted via EFS-Web with the application and is incorporated herein by reference in its entirety.

FIELD

The present technology relates to cell-free systems, methods, and kits for expressing proteins in vitro and evaluating the expressed proteins. In particular, the technology relates to cell-free systems, methods, and kits for expressing antibodies, antigen-binding fragment thereof, and antibody derivatives in vitro and evaluating the expressed antibodies, antigen-binding fragment thereof, and antibody derivatives.

BACKGROUND

Antibodies are widely used as protein-based drugs and diagnostics. They are the critical component in immunoassays enabling rapid diagnostics[1] and constitute one of the fastest growing classes of therapeutics with nearly 25% of new FDA approved drugs in 2020 being antibodies[2,3]. They have also recently garnered attention as potential countermeasures for emerging pathogens, and currently constitute the majority of emergency use authorized treatments for COVID-19 that inhibit the SARS-CoV-2 virus[4-6].

Modern workflows for antibody discovery utilize either directed evolution or the isolation of single B-cell clones from convalescent patients or animals to go from $>10^8$ possible sequences to a pool of $\sim10^3$ candidates targeting the desired antigen. However, once this pool of candidates has been generated, state-of-the-art workflows still rely on labor intensive and poorly scalable procedures (e.g., plasmid-based cloning, cell-based protein expression, protein purification, binding assessment through enzyme linked immunosorbent assays (ELISAs), etc.) to individually evaluate and identify the best antibody candidates[7,8]. These labor-intensive procedures represent a major bottleneck in antibody discovery because they are slow, taking weeks to months. Additionally, the effort to identify antibodies against emerging threats like the SARS-CoV-2 during the COVID-19 pandemic has highlighted (i) the importance of rapid and high-throughput antibody discovery platforms and (ii) the importance of identifying high-affinity antibodies targeting conserved epitopes[9,10] or non-overlapping epitopes[11,12] to resist viral escape and increase the ability to neutralize viral variants[13,14]; both of which have required intensive screening campaigns. A further challenge is that existing antibody discovery processes frequently have low efficiency, with very few of the screened candidates being potent neutralizers in the case of SARS-CoV-2 ($<0.01$ µg/mL neutralization $IC_{50}$). Taken together, these limitations in existing antibody discovery processes suggest the need for faster and higher throughput screens.

SUMMARY

The present technology relates to cell-free systems, methods, and kits for expressing proteins in vitro and evaluating the expressed proteins. In particular, the present technology relates to cell-free systems, methods, and kits for expressing antibodies, antigen-binding fragment thereof, and antibody derivatives in vitro and evaluating the expressed antibodies, antigen-binding fragment thereof, and antibody derivatives.

In one embodiment, a method is provided, the method comprising: a) assembling a linear expression template (LET) from nucleic acid sequences (e.g., restriction fragments, PCR products), wherein assembling does not include the use of cells or cell culture; and wherein assembling comprises Golden Gate Assembly or Gibson Assembly; b) amplifying the LET to generate amplification products; c) contacting the amplification products of (b) with a cell-free protein expression system (CFPS) to produce protein products; d) characterizing the protein products of (c), wherein characterization comprises Amplified Luminescent Proximity Homogeneous Linked Immunosorbent Assay (AlphaLISA).

In some embodiment, the CFPS comprises an *Escherichia coli* (*E. coli*) extract. In some embodiments, the *E. coli* comprises a mutation in the trxB and gor *E. coli* reductase genes. In some embodiments, the nucleic acid sequences of step (a) comprise one or more of: (i) double-stranded linear DNA encoding a variable heavy (VH) chain sequence of a target antibody; (ii) double-stranded linear DNA encoding a variable light (VL) chain sequence of a target antibody; (iii) double-stranded linear DNA encoding a heavy chain constant (CH), such as constant heavy 1 (CH1) domain of a target antibody; (iv) double-stranded linear DNA encoding a light chain constant (CL) domain of a target antibody; (v) double-stranded linear DNA comprising an expression vector backbone or fragments thereof.

In some embodiments, the expression vector of (v) comprises a prokaryotic expression vector. In some embodiments, the expression vector comprises a destination plasmid, such as for Golden Gate assembly, e.g., plasmids such as pJL1, pJLD1-3, or derivatives thereof. In some embodiments, the protein products of (c) comprise antigen-binding proteins. In some embodiments, the antigen binding proteins comprise one or more of a full-length antibody, a Fab, and a scFV. In some embodiments, the Fab comprises a sdFab. In some embodiments, amplification comprises the polymerase chain reaction.

In some embodiments, the AlphaLISA assay comprises donor and acceptor beads, wherein the donor beads comprise a first antigen, and wherein the acceptor beads comprise a second antigen, and wherein the protein products of (c) comprise antigen-binding proteins. In some embodiments, the first and second antigens comprise the same protein. In some embodiments, the first and second antigens comprise different proteins.

In some embodiments, the nucleic acid sequences of step (a) comprises: (i) double-stranded linear DNA coding for variable heavy (VH) chain domain of a target antibody and a double-stranded linear DNA coding for heavy chain constant (CH1) domain of the target antibody; or (ii) double-stranded linear DNA coding for variable light (VL) chain sequences of the target antibody and double-stranded linear DNA coding for light chain constant (CL) domain of the target antibody.

In some embodiments, the nucleic acid sequences of step (a) are from a B-cell isolated from an immunized animal; amplified via PCR from single cells after FACS sorting; identified via in vitro selection and individual sequences are recovered after cloning and transformation of the selected sequences; identified via in vitro selection and individual sequences are identified via DNA sequencing; identified via computational methods for predicting protein structure and function; or produced via DNA synthesis.

In some embodiments, the AlphaLISA assay comprises donor beads and acceptor beads, wherein the donor beads comprise a first protein product of step (c), wherein the first protein product of (c) comprises a VL domain and a CL domain of a target antibody; and wherein the acceptor beads comprises a second protein product of step (c), wherein the second protein product of (c) comprises a VH and a CH1 of the target antibody. In some embodiments, the AlphaLISA further comprises an antigen that binds the target antibody.

In some embodiments, the method is automated. In some embodiments, the method is performed on 384 well plates.

BRIEF DESCRIPTION OF THE DRAWINGS

FIG. 1a-d. A high-throughput, cell-free antibody screening workflow. a, Schematic of the steps involved in the cell-free antibody screening workflow. b, Diagram of the AlphaLISA screen for neutralizing antibodies via competition with ACE2 for the SARS-CoV-2 RBD. c, Evaluation of commercial neutralizing antibodies (nAbs) in the AlphaLISA ACE2 competition screen (n=3 independent replicates±standard error of the mean). d, Comparison of the reported and measured potencies of commercial neutralizing antibodies.

FIG. 2a-f. Performance of the cell-free antibody screening workflow evaluated on previously published SARS-CoV-2 neutralizing antibodies. a-f, AlphaLISA data are presented as the mean of 3 independent replicates. Dashed line indicates three standard deviations away from background. a-b, Heatmap of the binding of previously published antibodies measured using AlphaLISA to detect S trimer binding ($\log_{10}$ scaled), RBD binding ($\log_{10}$ scaled), and ACE2 competition (linearly scaled). AlphaLISA data are presented as the mean of 3 independent replicates. The lowest reported neutralization $IC_{50}$ value is also plotted for comparison ($\log_{10}$ scaled) and an X indicates a no relevant data available (Tables 1 and 2). a, Heatmap of the binding of 36 diverse antibodies. b, Heatmap of the binding of all 84 antibodies in the Brouwer et al. data set. c-d, Parity plots comparing the AlphaLISA the 84 antibodies in the Brouwer et al. data set vs the published ELISA data. Dashed line indicates three standard deviations away from background. c, S trimer binding. d, RBD binding. e, Comparison of the S trimer and RBD AlphaLISA binding data. f, Parity plot comparing the AlphaLISA ACE2 competition data for the 84 antibodies in the Brouwer et al. data set vs the published psuedovirus neutralization data. Antibodies that were reported to compete with ACE2 by Brouwer et al. are plotted in red.

FIG. 3a-f. The cell-free DNA assembly and amplification workflow. a, Schematic of the cell-free DNA assembly and amplification protocol for generating sfGFP linear expression template for CFPS. b, Agarose gel of amplified LET PCR products of Gibson assembly reactions. Backbone only and insert only conditions included as negative controls. Labeled band indicates assembly and amplification of the correct length PCR product. c, sfGFP yields in Origami™ B(DE3) CFPS from cell-free assembled linear expression templates and purified plasmid (n=3 independent replicates±standard error of the mean). d, Schematic of the cell-free DNA assembly and amplification protocol for generating sdFab linear expression template for CFPS. e, Agarose gel of amplified sdFab heavy chain (HC) LET PCR products. Labeled bands indicate assembly and amplification of the correct length PCR product. f, Agarose gel of amplified sdFab light chain (LC) LET PCR products. Labeled bands indicate assembly and amplification of the correct length PCR product.

FIG. 4a-c. Development of an Origami™ B(DE3) CFPS system for the expression of antibodies and antibody fragments. a-c, SDS PAGE of antibodies and antibody fragments manufactured in CFPS. Samples were fluorescently labeled with the FluoroTect™ reagent during protein synthesis. a, Expression and assembly of full length Trastuzumab (αHER2). The antigen binding fragment (Fab) and constant (FC) domains are labeled. b, Expression and assembly of a panel of 13 Fab s. c, Expression and assembly of a panel of 13 sdFabs. The leucine zipper heterodimer (LZA and LZB) assisting with Fab assembly are labeled.

FIG. 5a-f. AlphaLISA for profiling antibody protein-protein interactions in CFPS. a c, Evaluation of the effect of CFPS reagents on AlphaLISA. Concentrations are plotted as v/v fraction of the final concentration of the reagent in a CFPS reaction. Reagents were diluted in water at the concentration they normally reside at in CFPS. Reagents were tested in mixtures that were used to assemble CFPS reactions. Salt solution contains 8 mM magnesium glutamate, 10 mM ammonium glutamate, and 130 mM potassium glutamate. Master Mix contains 1.2 mM ATP, 0.85 mM GTP, 0.85 mMUTP, 0.85 mM CTP, 0.03 mg/mL folinic acid, and 0.17 E. coli tRNA. Reagent Mix contains 0.4 mM NAD, 0.27 mM CoA, 4 mM oxalic acid, 1 mM putrescine, 1.5 mM spermidine, and 57 mM HEPES. Amino Acid Mix contains 2 mM of all 20 amino acids. PEP is 30 µM phospho-enolpyruvate. LET is 0.066 v/v fraction unpurified PCR mix containing the LET for sfGFP. a, Evaluation of the effect of CFPS reagents on AlphaLISA detection chemistry using the TrueHits kit. Biotin and Streptavidin labeled beads associate directly with one anoter and serve as a control for reagents impacting the AlphaLISA measurement chemistry. b, Evaluation of the effect of CFPS reagents on AlphaLISA detection of the SARS-CoV-2 RBD and ACE2 interaction measured by the Protein A donor beand and Ni Chelate acceptor bead. The Salt Solution and Amino Acids Mix inhibit immobilization of his-tagged proteins on the NiChelate bead. c, Evaluation of the effect of CFPS reagents on AlphaLISA detection of the SARS-CoV-2 RBD and ACE2 interaction measured by the Protein A donor beand and anti-6×his acceptor bead. The Salt Solution and Amino Acids Mix inhibit immobilization of his-tagged proteins on the NiChelate bead. d, Schematic of AlphaLISA setup for measuring sdFab assembly. e, SDS PAGE of a panel of sdFabs produced in CFPS and labeled during translation with radioactive amino acids and imaged using a phosphors screen. f, Assembly AlphaLISA measurement of a panel of sdFabs. AlphaLISA signal is indicative of sdFab assembly, though the signal is subject to the hook effect[53] resulting in lower signal at higher concentrations.

FIG. 6a-d. Analysis of variability in AlphaLISA replicates. a-d, From top to bottom: Histogram of raw AlphaLISA values (mean of n=3 independent replicates) to visualize the spread of the data. Histogram of coefficient of variation (standard deviation divided by the mean) to visualize the typical error witin a sample; the mean coefficient of variation is displayed on the plot. Parity plots of the three replicates were fit to the line y=x to visualize the consistency of replicates; the corresponding $R^2$ value is displayed on the chart. Only values found to be significantly different from background are plotted ($p<0.05$, two-sided t-test adjusted for multiple comparisons using FDR with a family wise error rate of 5%) a, sdFab assembly AlphaLISA. b, SARS-CoV-2 S trimer binding AlpahLISA. c, SARS-CoV-2 RBD binding AlphaLISA. d, sdFab competition with ACE2 for the SARS-CoV-2 RBD AlphaLISA.

FIG. 7a-h. AlphaLISA profiling of 38 published antibodies. Data are a quantitative depiction of the data for 38 of the antibodies in the heatmaps in FIG. 2a-b. a, Schematic depicting AlphaLISA setup for measuring sdFab assembly. b, d, f, and h, All AlphaLISA data are the mean of three independent replicates±the standard error of the mean. The dashed line indicates three standard deviations away from background. Samples determined not to be significantly distinguished from background (p>0.05 two-sided t-test corrected using the FDR procedure) have bars that are filled dark grey. The samples are ranked within each category from worst (left) to best (right) neutralizers by their minimum neutralization $IC_{50}$ value. b, AlphaLISA measurement of sdFab assembly. c, Schematic depicting AlphaLISA setup for measuring S trimer binding. d, AlphaLISA measurement of sdFab binding to the SARS-CoV-2 S trimer. e, Schematic depicting AlphaLISA setup for measuring RBD binding. f, AlphaLISA measurement of sdFab binding to the SARS-CoV-2 RBD. g, Schematic depicting AlphaLISA setup for measuring sdFab competition with ACE2 for the RBD. h, AlphaLISA measurement of sdFab competition with ACE2 for the RBD.

DETAILED DESCRIPTION

Figure 1A:
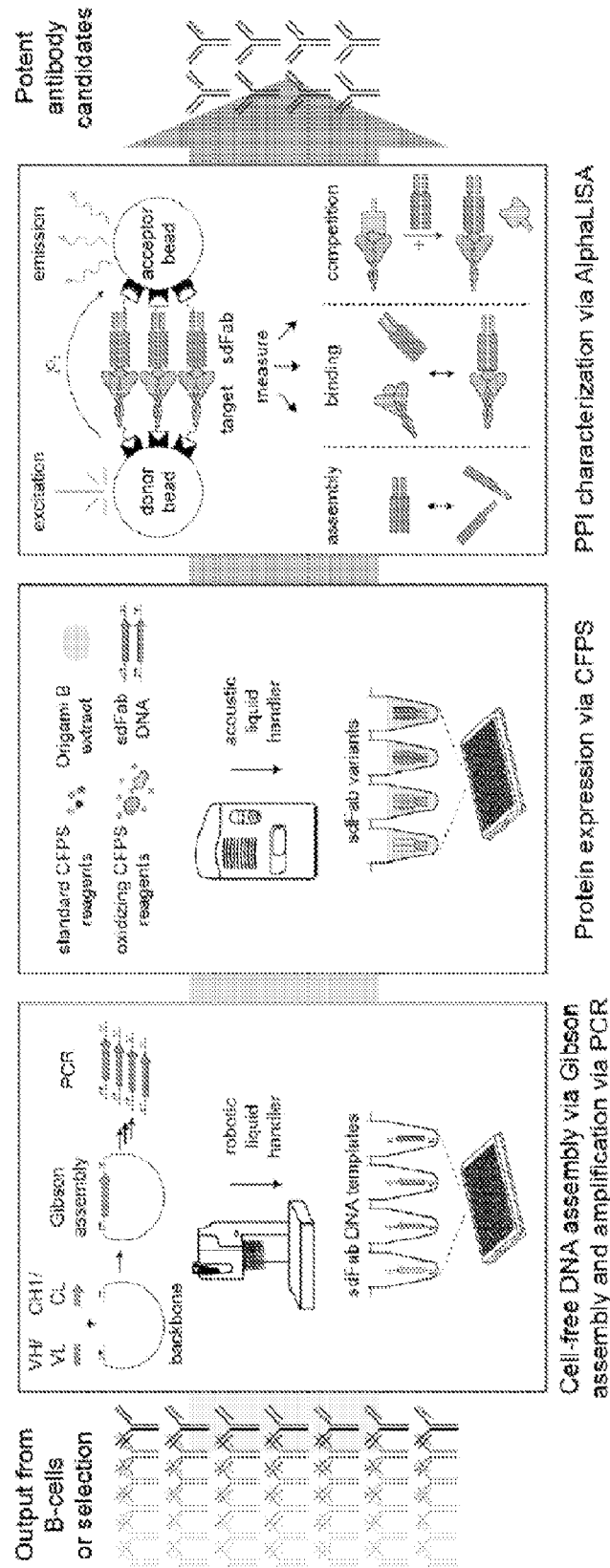

Disclosed herein are cell-free systems, methods, and kits for expressing antibodies, antigen-binding fragment thereof, and antibody derivatives in vitro. In some embodiments, the methods involve one or more cell-free protein synthesis (CFPS) reactions.

Cell-free protein synthesis (CFPS), the manufacture of proteins without living cells using crude extracts or purified components, is an attractive tool to overcome the limitations of modern workflow for antibody discovery. Towards this goal, a variety of CFPS systems for antibody expression have been developed[15-21] However, to our knowledge, no one has developed a bottleneck-free antibody screening workflow combining CFPS with a high-throughput protein-protein interaction screen. In this work we developed an integrated pipeline for antibody expression and evaluation to fully address the limitations in antibody discovery pipelines. The workflow leverages four key developments (FIG. 1a): (i) DNA assembly and amplification methods that do not require living cells, (ii) cell-free protein synthesis (CFPS) systems that can work directly from linear DNA templates and can generate disulfide-bonded antibody molecules, (iii) an Amplified Luminescent Proximity Homogeneous Linked Immunosorbent Assay (AlphaLISA) that enables rapid protein-protein interaction (PPI) or binding characterization without protein purification[22], and (iv) robotic and acoustic liquid handling that enables a highly parallel and miniaturized workflow. The integrated workflow disclosed herein is end-to-end automatable and enables a single researcher to express and profile the antigen-specific binding of hundreds of antibodies in 24 hours. As a model, we applied our workflow to profile a diverse set of 120 previously published antibodies, 119 of which are antibodies targeting the SARS-CoV-2 spike glycoprotein (S trimer). These antibodies were selected based on availability of sequence, structural, SARS-CoV-2 neutralization, and binding information, with 84 being drawn from Brouwer et al.[23] and the remainder from diverse sources[9,24-38] (Table 1 and 2). The antibodies span four orders of magnitude in neutralization potency and target a variety of domains and epitopes.

Definitions

To aid in understanding the invention, several terms are defined below.

Unless defined otherwise, all technical and scientific terms used herein have the same meaning as commonly understood by one of skill in the art. Although any methods and materials similar to or equivalent to those described herein can be used in the practice or testing of the claims, the exemplary methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

The term "about" means within a statistically meaningful range of a value or values such as a stated concentration, length, molecular weight, pH, time frame, temperature, pressure or volume. Such a value or range can be within an order of magnitude, typically within 20%, more typically within 10%, and even more typically within 5% of a given value or range. The allowable variation encompassed by "about" will depend upon the particular system under study.

The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, and includes the endpoint boundaries defining the range, unless otherwise indicated herein, and each separate value is incorporated into the specification as if it were individually recited herein.

The disclosed subject matter relates to antibodies, antigen-binding fragment thereof, and antibody derivatives which may include, but are not limited to, Fab's, scFv's, Ecobody's, and the like. In some embodiments, the antibodies, or antigen-binding fragments thereof are encoded on an expression template, for example a linear expression template, and expressed in cell-free protein synthesis reactions.

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, Meth, Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)n sequence, where n is in the range from about 20 to about 200). The region of the primer that is sufficiently complementary to the template to hybridize is referred to herein as the hybridizing region.

The term "promoter" refers to a cis-acting DNA sequence that directs RNA polymerase and other trans-acting transcription factors to initiate RNA transcription from the DNA template that includes the cis-acting DNA sequence.

The terms "target, "target sequence", "target region", and "target nucleic acid," as used herein, are synonymous and refer to a region or sequence of a nucleic acid which is to be amplified, sequenced or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning-A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, Biochemistry, 47: 5336-5353, which are incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, "expression template" refers to a nucleic acid that serves as substrate for transcribing at least one RNA that can be translated into a polypeptide or protein. Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably. In some embodiments, transcription templates are in vectors, such as an expression vector. In some embodiments, expression template comprise linear amplification products, e.g., linear expression templates.

As used herein, "translation template" refers to an RNA product of transcription from an expression template that can be used by ribosomes to synthesize polypeptide or protein.

The term "reaction mixture," as used herein, refers to a solution containing reagents necessary to carry out a given reaction. A reaction mixture is referred to as complete if it contains all reagents necessary to enable the reaction, and incomplete if it contains only a subset of the necessary reagents.

An "amplification reaction mixture", which refers to a solution containing reagents necessary to carry out an amplification reaction, typically contains oligonucleotide primers and a DNA polymerase in a suitable buffer.

A "PCR reaction mixture", which refers to a solution containing the reagents necessary to carry out a PCR reaction, typically contains DNA polymerase, dNTPs, and a divalent metal cation in a suitable buffer.

A "cell-free protein synthesis (CFPS) reaction mixture", which refers to a solution containing the reagents necessary to carry out CFPS, typically contains a crude or partially-purified bacterial or yeast extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture A "secondary reaction mixture," which refers to a solution containing the reagents necessary to carry out an enzyme-mediated biosynthetic steps, typically includes a feedstock that reacts in the presence of the enzyme to produce a final or intermediate product in the metabolic or biosynthetic pathway of interest. A secondary reaction mixture may optionally contain a cofactor, e.g. coenzyme-A, NAD, ATP, or a buffer.

The polynucleotide sequences contemplated herein may be present in expression vectors. For example, the vectors may comprise: (a) a polynucleotide encoding an ORF of a protein; (b) a polynucleotide that expresses an RNA that directs RNA-mediated binding, nicking, and/or cleaving of a target DNA sequence; and both (a) and (b). The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. Vectors as disclosed herein may include plasmid vectors. In some embodiments, the vector comprises a As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

In certain exemplary embodiments, vectors such as, for example, expression vectors, containing a nucleic acid encoding one or more rRNAs or reporter polypeptides and/or proteins described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more rRNAs or reporter polypeptides and/or proteins described herein) in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more rRNAs or reporter polypeptides and/or proteins described herein is linked to the regulatory sequence(s) in a manner which allows for expression of the nucleotide sequence (e.g., in an in vitro transcription and/or translation system). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990).

Oligonucleotides and polynucleotides may optionally include one or more non-standard nucleotide(s), nucleotide analog(s) and/or modified nucleotides. Examples of modified nucleotides include, but are not limited to diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

The terms "polynucleotide," "polynucleotide sequence," and "nucleic acid sequence" refer to oligonucleotides (which terms may be used interchangeably). These terms also refer to DNA or RNA of genomic, natural, or synthetic origin (which may be single-stranded or double-stranded and may represent the sense or the antisense strand). In some embodiments, a nucleic acid sequences may encode a gene or fragment of a gene, wherein the gene encodes an antibody or a region of an antibody. By way of example, but not by way of limitation, in some embodiments, nucleic acids comprise restriction fragments, generated by contacting a nucleic acid with a restriction enzyme such as a type II restriction enzyme, to generate the fragments. In some embodiments, the nucleic acid sequences are re-assembled, e.g., via the use of T4 DNA ligase in a Golden Gate assembly. In some embodiments, a nucleic acid sequence comprises a fragment of a variable heavy chain, a variable light chain, a constant heavy chain, or a constant light chain. In general, the fragments for LET assembly can encode or contain any additional functionality desired, e.g., to add to the target protein (antibody or fragment thereof). While a single fragment may make up a LET encoding a target protein, multiple fragments can also be used. For example, fragment A+fragment B=target protein. Three, four, five or more fragments are contemplated herein. For example, a library of variable light-chains could be tested in the context of different constant light-chains that are added during the LET assembly process. This allows for rational combinatorial screening of the variable light-chain fragments with the constant regions added during assembly. Other rational combinatorial schemes related to antibody binding fragments include, without limitation, screening a library of VH regions tested with various CH regions, such as CH1 regions; and screening the Fabs, or sdFabs of the library combinations. Additional functionalities, such as expression tags, or purification tags may be included. As is known in the art, the vector, or at least a subset of fragments, include the 5' and 3' untranslated regions necessary for cell free protein synthesis.

In some embodiments, the LETs encode a polypeptide such as a full-length antibody or an antibody fragment. By way of example, in some embodiments, a LET encodes one or more of a variable heavy (VH), variable light (VL), or more of a variable heavy (VH), variable light (VL), constant heavy (CH) (such as constant heavy 1 (CH1)), or a constant light (CL) antibody domain. In some embodiments, a LET encodes a VH and CH1. In some embodiments, a LET encodes a VL and a CL. In some embodiments, the antibody comprises an antibody directed to SarsCoV-2.

As used herein, the term "Golden Gate assembly" refers to a molecular method comprising assembly of multiple DNA fragments into a single template using Type IIS restriction enzymes and T4 DNA ligase. The assembly is performed in vitro, and common enzymes include BsaI, BsmBI, and BbsI. The methods, techniques, and optimizations involved with performing a Golden Gate assembly reaction are publicly available and are well known in the art. As is known in the art, destination vectors are used in the Golden Gate assembly processes. Such vectors are publicly available and known in the art, and the skilled artisan is well capable of identifying, making, or purchasing an appropriate destination vector. By way of example, the promoters and other 5' and 3' UTR elements are found on the CFPS vector pJL1 (see e.g., world wide web, at addgene.org/browse/article/15697). The necessary Golden Gate sites in context of the pJL1 elements can be found in https doi.org/10.10.1093/synbio/usaa019 (termed pJD1-3).

As used herein, the term "Gibson assembly" refers to a molecular cloning method which joins multiple DNA fragments into a single template in a single, isothermal reaction. In Gibson assembly, the DNA fragments include a ~20-40 base pair overlap with adjacent DNA fragments. These DNA fragments are mixed with a cocktail of three enzymes, along with other buffer components. The three required enzyme activities are exonuclease, DNA polymerase, and DNA ligase. Briefly, the exonuclease chews back DNA from the 5' end, thus not inhibiting polymerase activity and allowing the reaction to occur in one single process. The resulting single-stranded regions on adjacent DNA fragments can anneal. The DNA polymerase incorporates nucleotides to fill in any gaps. The DNA ligase covalently joins the DNA of adjacent segments, thereby removing any nicks in the DNA. The resulting product is different DNA fragments joined into one. Either linear or closed circular molecules can be assembled. As is known in the art, destination vectors are used in the Gibson assembly processes. Such vectors are publicly available and known in the art, and the skilled artisan is well capable of identifying, making, or purchasing an appropriate destination vector. By way of example, but not by way of limitation, pJL1 vectors can be used.

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, *E. coli*, plants, and other host cells.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

Peptides, Polypeptides, Proteins, and Synthesis Methods

As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard or unnatural amino acids. The term "amino acid residue" may include alpha-, beta-, gamma-, and delta-amino acids.

In some embodiments, the term "amino acid residue" may include nonstandard or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard or unnatural amino acids include, but are not limited, to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-G1cNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 20ufa20hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an a-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, 2nd edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length >100 amino acids (Garrett & Grisham, Biochemistry, 2nd edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

A modified amino acid sequence that is disclosed herein may include a deletion in one or more amino acids. As utilized herein, a "deletion" means the removal of one or more amino acids relative to the native amino acid sequence. The modified amino acid sequences that are disclosed herein may include an insertion of one or more amino acids. As utilized herein, an "insertion" means the addition of one or more amino acids to a native amino acid sequence. The modified amino acid sequences that are disclosed herein may include a substitution of one or more amino acids. As utilized herein, a "substitution" means replacement of an amino acid of a native amino acid sequence with an amino acid that is not native to the amino acid sequence.

A "variant," "mutant," or "derivative" of a reference polypeptide sequence may include a deletion relative to the reference polypeptide sequence. By way of example in some embodiment, the LETs encode a wild-type antibody or fragment thereof, or encode a variant antibody or fragment thereof.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, or variants, described herein may have one or more functional or biological activities exhibited by a reference polypeptide (e.g., one or more functional or biological activities exhibited by wild-type protein). In some embodiments, the activity of the variant or mutant protein (e.g., a modified antibody or antigen-binding fragment, for example encoded by an assembled LET as disclosed herein) may have an activity that is enhanced, as compared to a comparable wild-type or control antibody or antigen-binding fragment, or may have an alternative or a modified activity as compared to a comparable or wild-type or control antibody or antigen-binding fragment. Such activity may be characterized via an AlphaLISA assay as disclosed herein.

As used herein, a "target antibody" refers to an antibody, or a fragment of the target antibody, to be analyzed, evaluated, tested, synthesized, etc. by the methods disclosed herein. By way of example, in some embodiments, target antibodies are produced from PCR products amplified from a single B-cell from an immunized animal. The PCR products are processed according to Golden Gate assembly techniques or Gibson assembly techniques to generate LETs, which are then contacted with a CFPS to produce the target antibodies. The target antibodies are then analyzed via AlphaLISA, to identify desired characteristics, such as binding affinity, specific epitope recognition, etc.

Antibody fragments, or antigen binding proteins are also "targets" of the methods disclosed herein. Different forms of antibody fragments, and antigen binding proteins are well known in the art, and include without limitation, Fabs, sdFabs, scFvs, diabodies, nanobodies scFv-Fcs, scFv-CHs, scFabs, scFv-zippers, affibodies, DARPINS, single-chain antibodies (VH domain or nanobody), and minibinders, see e.g., Crook, et al., Trends in Biochem. Sci. 45:4:pp 332-346; (Apr. 1, 2020); Cao et al., Science 370:6515:pp 426-431 (Oct. 23, 2020).

As used herein the term AlphaLISA refers to a bead-based no-wash luminescent assay. When donor and acceptor beads are brought together, a signal (e.g., a luminescent signal) is created. In some embodiments, the donor and acceptor beads are linked to antibodies, and binding of a target such as an antigen, brings the beads into proximity creating a detectable signal. In some embodiments, the donor and acceptor molecules are linked to an antigen, and binding of an antibody to the antigens brings the beads into proximity, thereby creating a signal. In some embodiments, the antigens comprise the same protein. In some embodiments, the antigens comprise different proteins. In some embodiments, the donor or acceptor is linked to an antigen and the other of the donor or acceptor is linked to an antibody or an antibody fragment. In some embodiments, a control antibody or antibody fragment is provided in the assay, wherein the binding strength, specificity, and/or target epitopes of the control are known. If a signal is produced, this indicates that the bead-bound antibody or antibody fragment has outcompeted the competitive or control antibody or antibody fragment for binding the antigen. In some embodiments, each bead is bound by one or the other of the heavy chain or the light chain of a Fab. In some embodiments, each Fab chain comprises a one member of a leucine zipper heterodimer (LZA and LZB) or other assembly dimer. By way example, but not by way of limitation, additional structures include coiled heterodimers, computationally designed heterodimers, see e.g., Leber et al., Nature Chem Biol 16, 513-519 (2020); Nature, Chen, et al., 565, 106-111 (2019).

Cell-Free Protein Synthesis (CFPS)

The components, systems, and methods disclosed herein may be applied to, or adapted to cell-free protein synthesis methods as known in the art. See, for example, U.S. Pat. Nos. 5,478,730; 5,556,769; 5,665,563; 6,168,931; 6,548, 276; 6,869,774; 6,994,986; 7,118,883; 7,186,525; 7,189, 528; 7,235,382; 7,338,789; 7,387,884; 7,399,610; 7,776, 535; 7,817,794; 8,703,471; 8,298,759; 8,715,958; 8,734, 856; 8,999,668; and 9,005,920. See also U.S. Published Application Nos. 2018/0016614, 2018/0016612, 2016/ 0060301, 2015-0259757, 2014/0349353, 2014-0295492, 2014-0255987, 2014-0045267, 2012-0171720, 2008- 0138857, 2007-0154983, 2005-0054044, and 2004- 0209321. See also U.S Published Application Nos. 2005- 0170452; 2006-0211085; 2006-0234345; 2006-0252672; 2006-0257399; 2006-0286637; 2007-0026485; 2007-

0178551. See also Published PCT International Application Nos. 2003/056914; 2004/013151; 2004/035605; 2006/102652; 2006/119987; and 2007/120932. See also Jewett, M. C., Hong, S. H., Kwon, Y. C., Martin, R. W., and Des Soye, B. J. 2014, "Methods for improved in vitro protein synthesis with proteins containing non-standard amino acids," U.S. Patent Application Ser. No. 62/044,221; Jewett, M. C., Hodgman, C. E., and Gan, R. 2013, "Methods for yeast cell-free protein synthesis," U.S. Patent Application Ser. No. 61/792,290; Jewett, M. C., J. A. Schoborg, and C. E. Hodgman. 2014, "Substrate Replenishment and Byproduct Removal Improve Yeast Cell-Free Protein Synthesis," U.S. Patent Application Ser. No. 61/953,275; and Jewett, M. C., Anderson, M. J., Stark, J. C., Hodgman, C. E. 2015, "Methods for activating natural energy metabolism for improved yeast cell-free protein synthesis," U.S. Patent Application Ser. No. 62/098,578. See also Guarino, C., & DeLisa, M. P. (2012). A prokaryote-based cell-free translation system that efficiently synthesizes glycoproteins. Glycobiology, 22(5), 596-601. The contents of all of these references are incorporated in the present application by reference in their entireties.

As described above, in some embodiments, a "CFPS reaction mixture" typically may contain a crude or partially-purified cell extract (e.g., a yeast or bacterial extract), an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture. A reaction mixture is referred to as complete if it contains all reagents necessary to enable the reaction, and incomplete if it contains only a subset of the necessary reagents. It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

The disclosed cell-free protein synthesis systems may utilize components that are crude and/or that are at least partially isolated and/or purified. As used herein, the term "crude" may mean components obtained by disrupting and lysing cells and, at best, minimally purifying the crude components from the disrupted and lysed cells, for example by centrifuging the disrupted and lysed cells and collecting the crude components from the supernatant and/or pellet after centrifugation. The term "isolated or purified" refers to components that are removed from their natural environment, and are at least 60% free, preferably at least 75% free, and more preferably at least 90% free, even more preferably at least 95% free from other components with which they are naturally associated.

In some embodiments, CFPS reactions include a crude or partially-purified cell extract. In some embodiments, the cells used to derive the crude or partially purified extract may be selected based on the presence or absence of specific endogenous biochemical pathways, and/or engineered biochemical pathways. For example, cells that direct carbon flux, prevent or minimize side product formation, and prevent or minimize promiscuous background activity may be advantageous as compared to other cells. In some embodiments, the cell is a prokaryotic cell (e.g., bacterial cell) or a eukaryotic cell (e.g., a yeast cell). In some embodiments, the cell is a prokaryotic cell and comprises and E. coli cell. In some embodiments, the E. coli cell comprises a modified E. coli cell, such as BL21, JST07, MB263, MP263sucD, and JC01. In some embodiments, the E. coli cell comprises JST07.

As used herein, "translation template" for a polypeptide refers to an RNA product of transcription from an expression template that can be used by ribosomes to synthesize polypeptides or proteins.

The term "reaction mixture," as used herein, refers to a solution containing reagents necessary to carry out a given reaction. A reaction mixture is referred to as complete if it contains all reagents necessary to perform the reaction. Components for a reaction mixture may be stored separately in separate container, each containing one or more of the total components. Components may be packaged separately for commercialization and useful commercial kits may contain one or more of the reaction components for a reaction mixture.

For example, a CFPS reaction mixture may include an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the reaction mixture may comprise a coupled transcription/translation ("Tx/Tl") system where synthesis of translation template and a sequence defined biopolymer from the same cellular extract.

The CFPS reaction mixture may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract.

Altering the physicochemical environment of the CFPS reaction to better mimic the cytoplasm can improve protein synthesis activity. The following parameters can be considered alone or in combination with one or more other components to improve robust CFPS reaction platforms based upon crude cellular extracts.

The temperature may be any temperature suitable for CFPS. Temperature may be in the general range from about 10° C. to about 40° C., including intermediate specific ranges within this general range, include from about 15° C. to about 35° C., from about 15° C. to about 30° C., from about 15° C. to about 25° C. In certain aspects, the reaction temperature can be about 15° C., about 16° C., about 17° C., about 18° C., about 19° C., about 20° C., about 21° C., about 22° C., about 23° C., about 24° C., about 25° C.

The reaction mixture may include any organic anion suitable for CFPS. In certain aspects, the organic anions can be glutamate, acetate, among others. In certain aspects, the concentration for the organic anions is independently in the general range from about 0 mM to about 200 mM, including intermediate specific values within this general range, such as about 0 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM and about 200 mM, among others.

The reaction mixture may include any halide anion suitable for CFPS. In certain aspects the halide anion can be chloride, bromide, iodide, among others. A preferred halide anion is chloride. Generally, the concentration of halide anions, if present in the reaction, is within the general range from about 0 mM to about 200 mM, including intermediate specific values within this general range, such as those disclosed for organic anions generally herein.

The reaction mixture may include any organic cation suitable for CFPS. In certain aspects, the organic cation can be a polyamine, such as spermidine or putrescine, among others. Preferably polyamines are present in the CFPS reaction. In certain aspects, the concentration of organic cations in the reaction can be in the general about 0 mM to about 3 mM, about 0.5 mM to about 2.5 mM, about 1 mM to about 2 mM. In certain aspects, more than one organic cation can be present.

The reaction mixture may include any inorganic cation suitable for CFPS. For example, suitable inorganic cations can include monovalent cations, such as sodium, potassium, lithium, among others; and divalent cations, such as magnesium, calcium, manganese, among others. In certain aspects, the inorganic cation is magnesium. In such aspects, the magnesium concentration can be within the general range from about 1 mM to about 50 mM, including intermediate specific values within this general range, such as about 1 mM, about 2 mM, about 3 mM, about 5 mM, about 6 mM, about 7 mM, about 8 mM, about 9 mM, about 10 mM, among others. In preferred aspects, the concentration of inorganic cations can be within the specific range from about 4 mM to about 9 mM and more preferably, within the range from about 5 mM to about 7 mM.

The reaction mixture may include endogenous NTPs (i.e., NTPs that are present in the cell extract) and or exogenous NTPs (i.e., NTPs that are added to the reaction mixture). In certain aspects, the reaction use ATP, GTP, CTP, and UTP. In certain aspects, the concentration of individual NTPs is within the range from about 0.1 mM to about 2 mM.

The reaction mixture may include any alcohol suitable for CFPS. In certain aspects, the alcohol may be a polyol, and more specifically glycerol. In certain aspects the alcohol is between the general range from about 0% (v/v) to about 25% (v/v), including specific intermediate values of about 5% (v/v), about 10% (v/v) and about 15% (v/v), and about 20% (v/v), among others.

EXEMPLARY EMBODIMENT

Presented below are several, non-limiting exemplary embodiments of the systems, methods, and compositions disclosed herein.

Embodiment 1. A method, system, or kit for the high throughput expression of antibodies, antigen-binding fragments thereof of antigen derivatives (Fab, ScFv, Ecobody, etc.) using cell-free protein synthesis aided by liquid handling robotics followed by functional evaluation without purification. The method or system may comprise one or more of the following steps, or the kit may comprise one or more components for performing one or more of the following steps:

a) Assembly of linear DNA expression templates without cells via PCR, Golden Gate Assembly, or Gibson Assembly.

b) Expression of antibodies using genetically modified *E. coli* extracts to facilitate proper disulfide bond formation.

c) Evaluation of antibody heavy and light chain assembly utilizing the AlphaLISA or AlphaScreen assay.

d) Evaluation of antibody binding strength, specificity, and target epitope in CFPS without purification using the AlphaLISA or AlphaScreen assay.

e) Automation of the process using liquid handling robotics.

Embodiment 2. The method or system of embodiment 1 where a non-antibody binding scaffold is expressed and evaluated, or wherein the kit comprises one or more components of the system, or one or more components for performing the method.

Embodiment 3. The method or system of embodiment 1 where 100's to 1000's of antibodies are evaluated in days rather than 10's to 100's of days.

Embodiment 4. The method or system of embodiment 1 where DNA sequences are amplified via PCR from single cells after FACS sorting, or wherein the kit comprises one or more components of the system, or one or more components for performing the method.

Embodiment 5. The method or system of embodiment 1 where DNA sequences are identified via in vitro selection and individual sequences are recovered after cloning and transformation of the selected sequences, or wherein the kit comprises one or more components of the system, or one or more components for performing the method.

Embodiment 6. The method or system of embodiment 1 where DNA sequences are identified via in vitro selection and individual sequences are identified via DNA sequencing, or wherein the kit comprises one or more components of the system, or one or more components for performing the method.

Embodiment 7. The method or system of embodiment 1 where DNA sequences are identified via computational methods for predicting protein structure and function, or wherein the kit comprises one or more components of the system, or one or more components for performing the method.

Embodiment 8. The method, system, or kit of embodiment 1 where DNA sequences are produced vis DNA synthesis, or wherein the kit comprises one or more components of the system, or one or more components for performing the method.

EXAMPLES

The following Examples are illustrative and are not intended to limit the scope of the claimed subject matter.

Example 1—A Workflow for the Cell-Free Expression and Evaluation of Antibodies Technical Field The technical field relates to Synthetic biology, biochemical engineering, antibody discovery, cell-free systems.

Abstract

Therapeutic monoclonal antibodies represent a more than 100-billion-dollar market and have been the predominant class of therapeutic drugs developed in recent years. However, despite enormous time and monetary investment in this space, antibody screening and development pipelines are still slow and of limited throughput. This is predominantly due to low throughput and labor-intensive methods required to express and evaluate antibodies. To address these limitations, we developed a workflow centered around Cell-Free Protein Synthesis (CFPS) that is capable of expressing and evaluating more than ten times the antibodies in less than one-third of the time. Our workflow consists of three different components that enable this goal: 1) cell-free DNA assembly, 2) cell-free antibody synthesis, and 3) high throughput antibody protein-protein interaction profiling using the AlphaLISA assay. Each of these steps can be completed in a 384 or 1536 well plate format without purifications between steps, enabling the process to be completed quickly and without experimental bottlenecks. Additionally, each step can be completed with the assistance of liquid handling robotics making the process highly automatable, requiring little human intervention. We anticipate that this work will have transformative impacts on the antibody discovery industry, not only accelerating the discovery process but also enabling the optimization of antibodies towards improved binding and stability due to the increased process throughput.

Applications

Applications of the disclose technology may include, but are not limited to: (i) Antibody screening and discovery; (ii) Protein-based binder (non-antibody) screening and discovery; and (iii) High-throughput protein expression.

Advantages

Advantages of the disclosed technology may include, but are not limited to: (i) Greatly improved process throughput (>10×); (ii) Greatly improved process speed (>3×); (iii) Does not require living cells during the workflow; (iv) End-to-end automatable process, requiring little to no human intervention; and (v) Sub microgram quantities of antibodies can be expressed and functionally evaluated.

There is a significant bottleneck in current methods for antibody discovery, most processes use cell-based expression which isn't amenable to high throughput screening and is labor intensive. There are many more possible antibody sequences identified via selection or sorting methods than what can be reasonably expressed and evaluated.

The disclosed technology enables greater than tenfold more antibodies to be evaluated in less than half the time, leading to the identification of a greater number of candidate antibodies for diagnostic, therapeutic, and research purposes. The invention will significantly reduce the cost per antibody evaluated and greatly accelerate the discovery process, enabling the identification of antibodies with the desired properties more quickly.

REFERENCES

EP3312278A1

JP2016002009A

WO2018025826A

WO2014172631A2

US20190032047A1

Ryabova, L. A., Desplancq, D., Spirin, A. S., & Pluckthun, A. (1997). Functional antibody production using cell-free translation: Effects of protein disulfide isomerase and chaperones. Nature Biotechnology, 15(1), 79-84. https://doi.org/10.1038/nbt0197-79

Oh, I.-S., Lee, J.-C., Lee, M., Chung, J., & Kim, D.-M. (2010). Cell-free production of functional antibody fragments. Bioprocess and Biosystems Engineering, 33(1), 127-132. https://doi.org/10.1007/s00449-009-0372-3

Murakami, S., Matsumoto, R., & Kanamori, T. (2019). Constructive approach for synthesis of a functional IgG using a reconstituted cell-free protein synthesis system. Scientific Reports, 9(1), 671. https:i/doi. org/10.1038/s41598-018-36691-8

Martin, R. W., Majewska, N. I., Chen, C. X., Albanetti, T. E., Jimenez, R. B. C., Schmelzer, A. E., . . . Roy, V. (2017). Development of a CHO-Based Cell-Free Platform for Synthesis of Active Monoclonal Antibodies. ACS Synthetic Biology, 6(7), 1370-1379. https:i/doi. org/10.1021/acssybio.7b00001

Ojima-Kato, T., Nagai, S., & Nakano, H. (2017). Ecobody technology: rapid monoclonal antibody screening method from single B cells using cell-free protein synthesis for antigen-binding fragment formation. Scientific Reports, 7(1), 13979. https://doi.org/10.1038/s41598-017-14277-0

Ojima-Kato, T., Morishita, S., Uchida, Y., Nagai, S., Kojima, T., & Nakano, H. (2018). Rapid Generation of Monoclonal Antibodies from Single B Cells by Ecobody Technology. Antibodies, 7(4), 38. https://doi.org/10.3390/antib7040038

Cai, Q., Hanson, J. A., Steiner, A. R., Tran, C., Masikat, M. R., Chen, R., . . . Yin, G. (2015). A simplified and robust protocol for immunoglobulin expression in Escherichia coli cell-free protein synthesis systems. Biotechnology Progress, 31(3), 823-831. https://doi.org/10.1002/btpr.2082

Thoring, L., Dondapati, S. K., Stech, M., Wustenhagen, D. A., & Kubick, S. (2017). High-yield production of "difficult-to-express" proteins in a continuous exchange cell-free system based on CHO cell lysates. Scientific Reports, 7(1), 11710. https://doi.org/10.3038/s41598-017-12188-8

Sun, Z. Z., Yeung, E., Hayes, C. A., Noireaux, V., & Murray, R. M. (2014). Linear DNA for rapid prototyping of synthetic biological circuits in an Escherichia coli based TX-TL cellfree system. ACS Synthetic Biology, 3(6), 387-397. https://doi.org/10.1021/sb400131a Sierecki, E., Giles, N., Polinkovsky, M., Moustaqil, M., Alexandrov, K., & Gambin, Y. (2013). A cell-free approach to accelerate the study of protein-protein interactions in vitro. Interface Focus, Vol. 3. https://doi.org/10.1098/rsfs.2013.0018

Sierecki, E., Stevers, L. M., Giles, N., Polinkovsky, M. E., Moustaqil, M., Mureev, S., Gambin, Y. (2014). Rapid Mapping of Interactions between Human SNX-BAR Proteins Measured In Vitro by AlphaScreen and Single-molecule Spectroscopy. Molecular & Cellular Proteomics, 13(9), 2233-2245. https://doi.org/10.1074/mcp.M113.037275

Example 2—Accelerating Antibody Discovery With Cell-Free Systems

Cell-free protein synthesis (CFPS), the manufacture of proteins without living cells using crude extracts or purified components, is an attractive tool to overcome current limitations in antibody production workflow. Towards this goal, a variety of CFPS systems for antibody expression have been developed[15-21]. However, to our knowledge, no one has developed a bottleneck-free antibody screening workflow combining CFPS with a high-throughput protein-protein interaction screen. In this work we developed an integrated pipeline for antibody expression and evaluation to fully address the limitations in antibody discovery pipelines. The workflow leverages four key developments (FIG. 1a): (i) DNA assembly and amplification methods that do not require living cells, (ii) cell-free protein synthesis (CFPS) systems that can work directly from linear DNA templates and can generate disulfide-bonded antibody molecules, (iii) an Amplified Luminescent Proximity Homogeneous Linked Immunosorbent Assay (AlphaLISA) that enables rapid protein-protein interaction (PPI) or binding characterization without protein purification[22], and (iv) robotic and acoustic liquid handling that enables a highly parallel and miniaturized workflow. Our integrated workflow is end-to-end automatable and enables a single researcher to express and profile the antigen-specific binding of hundreds of antibodies in 24 hours. As a model, we applied our workflow to profile a diverse set of 120 previously published antibodies, 119 of which are antibodies targeting the SARS-CoV-2 spike glycoprotein (S trimer). These antibodies were selected based on availability of sequence, structural, SARS-CoV-2 neutralization, and binding information, with 84 being drawn from Brouwer et al.[23] and the remainder from diverse sources[9,24-38] (Table 1 and Table 2, provided at the end of the Examples section). The antibodies span four orders of magnitude in neutralization potency and target a variety of domains and epitopes.

Figure 3A:
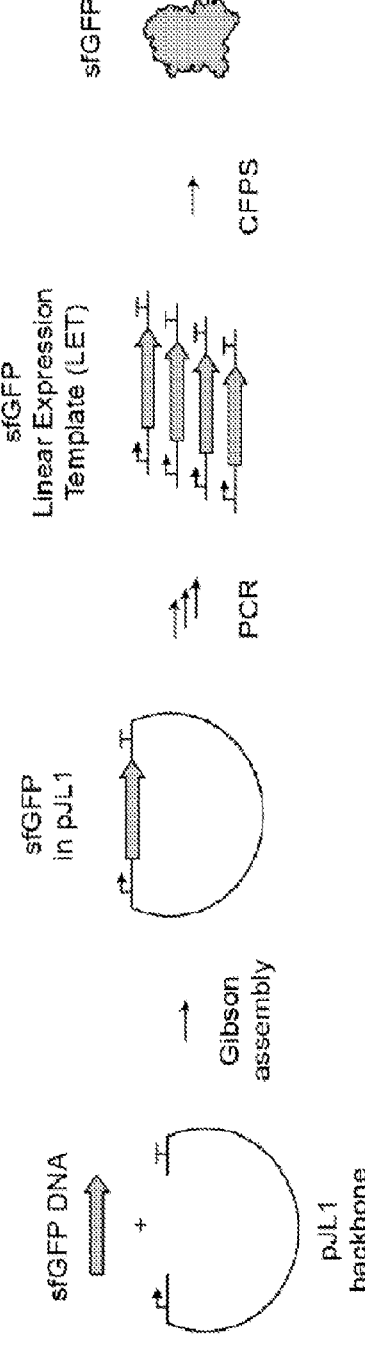
Figure 3D:
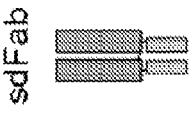
Figure 3D:
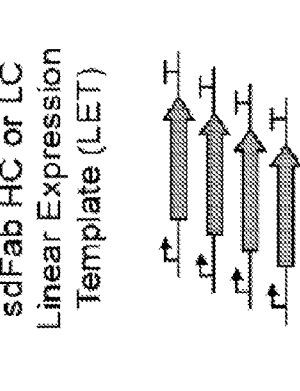
Figure 3D:
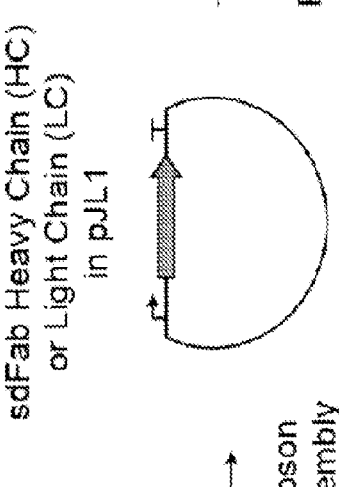
Figure 3D:
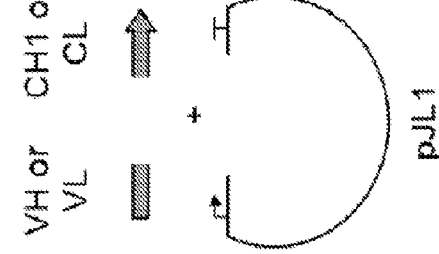

We first implemented a cell-free method for DNA assembly and amplification by adapting and optimizing recently reported protocols for high-throughput construction of DNA templates for CFPS[15,17,39,40]. The method consists of a Gibson assembly step, followed by PCR amplification of the linear expression template (LET) using the unpurified Gibson assembly product as a template. The key idea was to create a versatile approach for rapid construction of DNA templates without the requirement of cell-culture, allowing DNA assembly and amplification in less than 3 hours entirely in 384 well plates. To validate the method, we applied it to the assembly and amplification of an LET for sfGFP expression and only observed sfGFP expression in the presence of properly assembled DNA template (FIG. 3a-c). To assemble antibody DNA templates, we purchased synthetic, double-stranded linear DNA coding for the desired variable heavy (VH) and variable light (VL) chain sequences. These DNAs were assembled with DNA coding for the appropriate heavy chain constant (CH1) or light chain constant (CL) domains in addition to a separate piece of DNA coding for the backbone of the p7L1 vector. These sequences were subsequently amplified by PCR to generate amplified LETs (FIG. 3d-f). Previous works suggest that this workflow is compatible with PCR product amplified from single B-cells from an immunized animal[15,17,39] In addition to being fast, this workflow also affords flexibility, allowing assembly of different antibody formats (e.g., full-length, Fab, sdFab) containing different purification or immobilization tags by using different antibody constant regions in the assembly reaction.

We next demonstrated rapid antibody expression in a crude E. coli based CFPS system. We developed a high-yielding (1,390±32 μg/mL sfGFP, FIG. 3c) crude E. coli lysate-based CFPS system from the Origami™ B(DE3) strain (FIG. 4), which contains mutations in the trxB and gor E. coli reductase genes to enable the formation of disulfide bonds in the cytoplasm[41]. By pretreating the extract with the reductase-inhibitor iodoacetamide (IAM) to further stabilize the redox environment[42-44] and supplementing the reaction with purified E. coli disulfide bond isomerase DsbC and prolyl isomerase FkpA[18,45,46], we successfully expressed and assembled full-length trastuzumab, a model anti-HER2 antibody[47], from linear DNA templates (FIG. 4a). However, like others[15-19] we found that the efficient assembly of full-length antibodies in CFPS can require further optimization (e.g., temperature, DNA template ratio, DNA template expression timing) which is not optimal for high-throughput screening. Like reports by Ojima-Kato et al.[15-17] we found that the assembly of synthetically dimerized antigen binding fragments (sdFab, also called ecobodies[15,17] or zipbodies[16]) were more consistent that their corresponding antigen binding fragments (Fabs) in CFPS for a small panel of antibodies and opted to utilize the sdFab format for expression (FIG. 4b-c). Using acoustic liquid handling we can assemble CFPS reactions to express each sdFab variant from cell-free assembled and amplified DNA in 384-well plates (FIG. 1a).

Following DNA assembly and CFPS, antigen-specific binding was evaluated. To characterize the PPIs [protein protein interactions] of the expressed sdFabs, we developed an AlphaLISA method to characterize PPIs directly from CFPS reactions. AlphaLISA is an in-solution and wash-free assay that is designed for high-throughput screening and is compatible with crude cell-lysates[22]. In AlphaLISA, non-covalent capture chemistries are used to immobilize the proteins of interest on donor and acceptor beads, which generate a chemiluminescent signal when in proximity of one another and excited by a 680 nm laser. AlphaLISA is also flexible, enabling the measurement of both direct binding to an antigen as well as competition for specific epitopes. We first sought to validate that AlphaLISA is tolerant of crude CFPS reactions. We observed that CFPS does not interfere with the measurement chemistry (FIG. 4a), but that certain reaction components can interfere with protein immobilization to the bead which can be circumvented with the appropriate choice of immobilization chemistry (FIG. 5b-c). To validate the ability of AlphaLISA to profile neutralizing antibodies, we tested the ability of five different commercial antibodies to compete with the SARS-CoV-2 target human receptor Angiotensin-Converting Enzyme 2 (ACE2) for binding of the SARS-CoV-2 Receptor Binding Domain (RBD) and found that our determined rank order of $IC_{50}$ values aligns with the reported ELISA $IC_{50}$'s (FIG. 1b-d). A similar AlphaLISA method was also recently used to screen for small molecule inhibitors of the ACE2 and RBD interaction[48], highlighting its potential as a high-throughput screening assay. Further, we utilized AlphaLISA to develop a sdFab assembly screen to monitor antibody expression and assembly in CFPS, a laborious step that traditionally requires SDS-PAGE. The measurement immobilizes the heavy and light chains of the sdFab to the AlphaLISA beads, resulting in signal when the two chains are assembled (FIG. 5d). The AlphaLISA assembly assay shows consistent prediction of antibody assembly with SDS-PAGE on a panel of sdFabs (FIG. 5e-f).

Figure 2A:
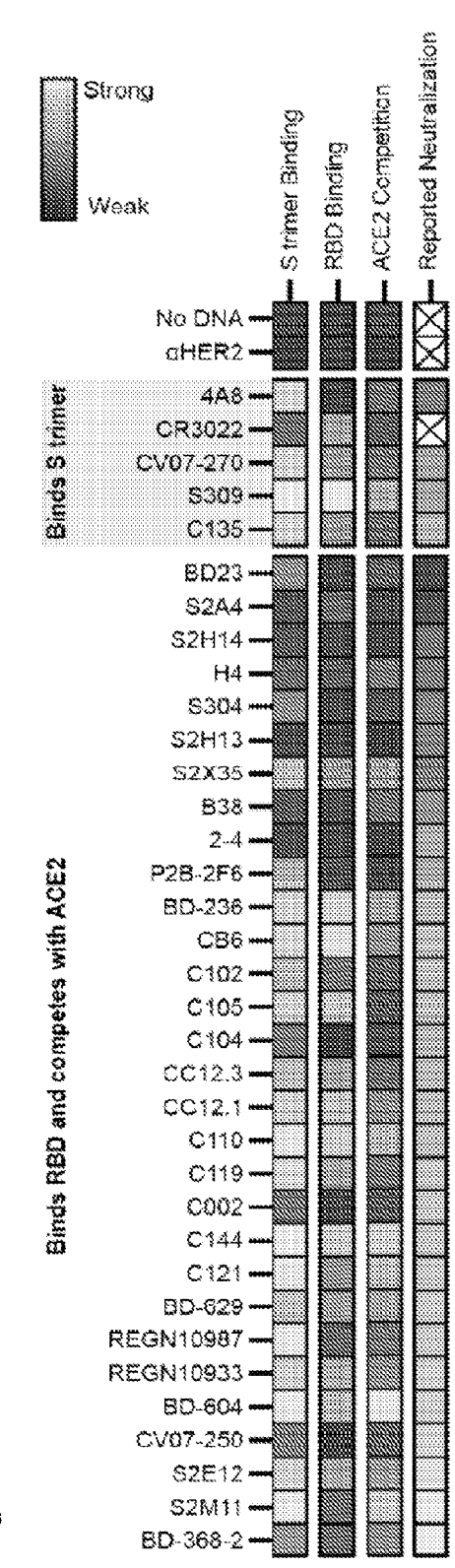
Figure 2B:
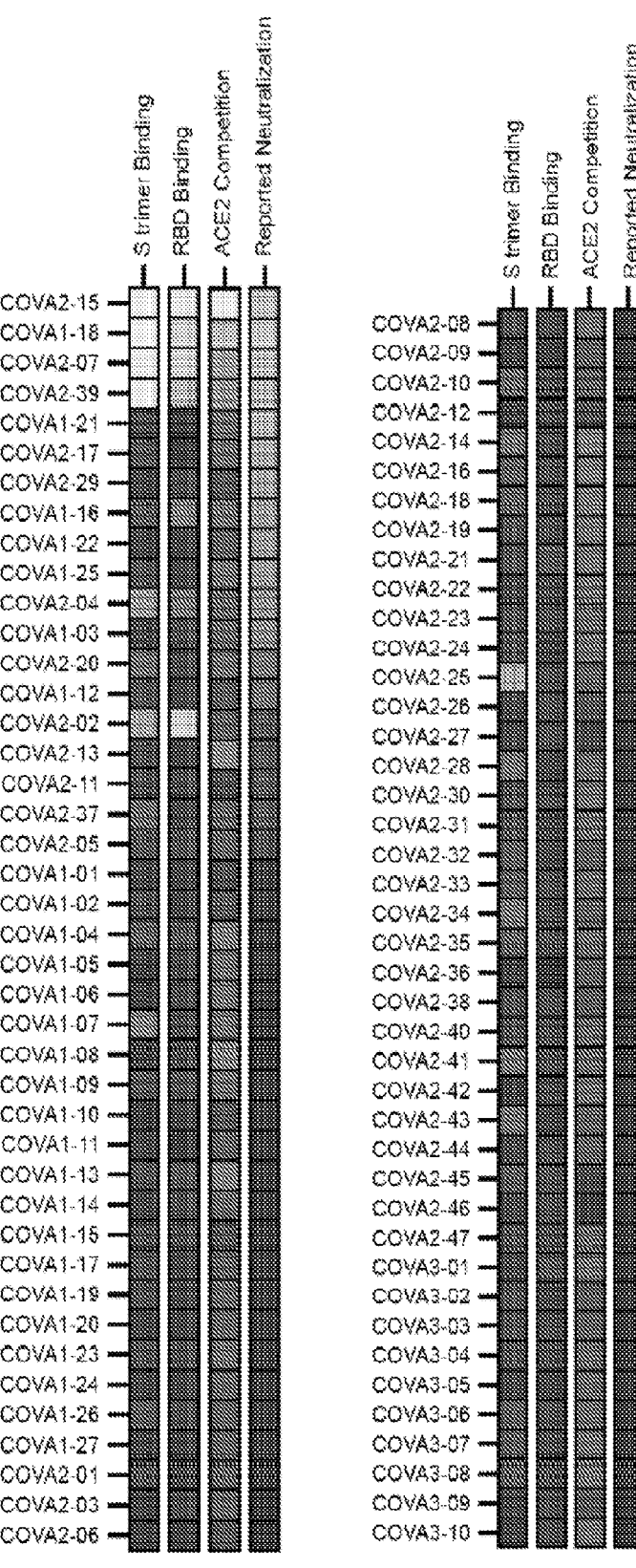

Using the developed workflow, we next evaluated a set of 120 unique antibodies using AlphaLISA to measure antibody binding the SARS-CoV-2 S trimer, binding the SARS-CoV-2 RBD, competition with ACE2 for RBD binding, and assembly of their heavy and light chains in CFPS (FIG. 1a and FIG. 2). Antibodies were expressed and evaluated in triplicate. When comparing each AlphaLISA replicate to another, replicates were found to be consistent with one another, validating that the acoustic liquid handling workflow is robust (FIG. 6). Samples were evaluated for significant assembly, binding to, or competition with a given target using a two-sided student's t-test corrected for multiple testing using the Benjamini and Hochberg False Discovery Rate procedure (FDR)[49]. Within the diverse set of 36 antibodies, we observed assembly for 36 out of 36 tested antibodies, S trimer binding for 28 out of 35 antibodies reported to bind the S trimer, RBD binding for 23 out of the 34 antibodies reported to bind the RBD, and ACE2 competition for 16 out of 31 antibodies reported to compete with ACE2 (FIG. 2a, FIG. 7). For the set of 84 antibodies from Brouwer et al. we observed assembly of 80 out 84 antibodies and binding to the S trimer and RBD for many of antibodies that showed strong binding via ELISA (FIG. 2b-d). We compared ACE2 competition against neutralization since it has been reported that more than 90% of neutralizing antibodies block the RBD and ACE2 interaction[26,50] and similar competition assays have been reported to correlate with neutralization potency[26,51] (FIG. 2e). We observed ACE2 competition, as well as strong S trimer and RBD binding, for 4 out of 5 antibodies reported to compete with ACE2, which also represent the four most potent neutralizers in the Brouwer et al. data set.

Notably, we observed ACE2 competition for 10 out of 13 antibodies in the overall data set whose neutralization $IC_{50}$ values are less than 0.01 µg/mL. While this workflow does not exhaustively characterize each antibody, our screen allows for consistent identification of potent neutralizing antibodies whose mechanism is ACE2 competition. We additionally observed that 4A8, an n-terminal domain targeted antibody[35], only showed strong interaction with the S trimer and that CR3022, whose target epitope is occluded in the S trimer[32,52], showed binding to the RBD, but weak binding to the S trimer. The 5309 antibody in the sdFab format exhibited competition with ACE2 although it has been previously reported not to compete with ACE2[9]. The data generated by our workflow are self-consistent and largely align with literature (Table 3, provided at the end of the Examples section). Further improvements to the dynamic range of the PPI measurements could broaden the utility for performing antigenic mapping of the immune response to antigens. Inclusion of other binding targets could allow researchers to easily evaluate targeting to different domains (e.g., SARS-CoV-2 n-terminal domain) or look for antibodies targeting conserved epitopes by evaluating cross reactivity with other related viruses (e.g., SARS-CoV, etc.).

In summary, we developed an integrated and automated workflow for antibody screening by combining methods for cell-free DNA assembly and amplification, cell-free protein expression, and highly parallel binding characterization via AlphaLISA. This workflow has two key features. First, it is fast. The entire workflow for all 120 antibodies evaluated in this study was completed in triplicate in less than 24 hours in two consecutive working days by a single researcher, highlighting the workflow's speed and throughput. Second, integration of the AlphaLISA assay in cell-free extracts without the need for protein purification, facilitates direct evaluation of synthesized antibodies in high-throughput. This is important because this is frequently the limiting step in previously published methods. Looking forward, we anticipate that the increased speed and throughput afforded by our workflow will enable researchers to easily and rapidly screen thousands of antibodies, facilitating down selection of a few highly potent candidates that can be expressed at larger scales in cells or using CFPS and subjected to deeper developability testing. We hope that our method will aid in the development of medical countermeasures in future next pandemics and broadly in the development of antibodies for therapeutic, diagnostic, and research applications.

Materials and Methods

Antibody sdFab Sequence Design sdFabs were assembled based on a modified version of previously published protocols[15-17]. Antibody sequences were collected from literature and their light chains were classified as either kappa or lambda via the terminal residue of the J-segment in the VL domain. The VH and VL domains were subsequently fused to their corresponding human constant heavy (Uniprot PODOX5) or human constant light (kappa CL Uniprot P01834 or lambda 1 CL Uniprot POCG04) chains. At the n-terminus of the VH and VL domains, we chose to include a modified expression tag based on the first 5-residues of the E. coli chloramphenicol acetyl transferase gene followed by a Tobacco Etch Virus (TEV) protease cleavage site (protein sequence: MEK-KIENLYFQS (SEQ ID NO: 1), DNA sequence: atg-gagaaaaaaatcgaaaacctgtacttccagagc, (SEQ ID NO: 2))[54] as opposed to the previously published SKIK (SEQ ID NO: 3) tag[55]. The heavy chain was fused to the LZA heterodimer subunit (AQLEKELQALEKE-NAQLEWELQALEKELAQK (SEQ ID NO: 4)) and a strep II tag. The light chain was fused to the LZB heterodimer subunit (AQLKKKLQALKK-KNAQLKWKLQALKKKLAQK (SEQ ID NO: 5)). Examples of the three types of antibody sequences are detailed below, with the important sequence features highlighted in square brackets[ ].

sdFab Heavy Chain Constant StrepII Tagged (SEQ ID NO: 6)
[MEKKIENLYFQS][VH_Sequence][ASTKGPSVFPLAPSSKSTSGG

TAALGCLVKDYFPEPVTVSWNSGALTSGVHTFPAVLQSSGLYSLSSVVT

VPSSSLGTQTYICNVNHKPSNTKVDKKVEPKSCIGGGGS[AQLEKELQA

LEKENAQLEWELQALEKELAQK]GSSA[WSHPQFEK]

sdFab Light Chain Kappa (SEQ ID NO: 7)
[MEKKIENLYFQS][VL_Sequence][RTVAAPSVFIFPPSDEQLKSG

TASVVCLLNNFYPREAKVQWKVDNALQSGNSQESVTEQDSKDSTYSLSS

TLTLSKADYEKHKVYACEVTHQGLSSPVTKSFNRGEC]GGGGS[AQLKK

KLQALKKKNAQLKWKLQALKKKLAQK]

sdFab Light Chain Lambda 1

(SEQ ID NO: 8)
[MEKKIENLYFQST|VL_Sequence]GQPKANPTVTLFPPSSEELQAN

KATLVCLISDFYPGAVTVAWKADGSPVKAGVETTKPSKQSNNKYAASSY

LSLTPEQWKSHRSYSCQVTHEGSTVEKTVAPTECS]GGGGS[AQLKKKL

QALKKKNAQLKWKLQALKKKLAQK]

DNA Assembly and Linear Expression Template (LET) Generation

Proteins to be manufactured via CFPS were codon optimized using the IDT codon optimization tool and ordered as double-stranded linear DNA containing the desired Gibson assembly overhangs from IDT or GenScript. sfGFP was ordered containing the two pJL1 Gibson assembly overhangs. Antibody VH DNA was ordered with the pJL1 5' and the human IgG1 heavy chain constant 5' Gibson overhangs. Antibody VL DNA was ordered with the pJL1 5' and the human Ig light chain kappa or lambda 1 Gibson assembly overhangs. DNA was resuspended at a concentration of 50 ng/μL and used without amplification.

Additional linear DNA components for Gibson assembly (pJL1 backbone, sdFab heavy chain constant strepII tagged, sdFab light chain kappa constant, sdFab light chain lambda 1 constant) were ordered as gblocks from IDT. These components were amplified using PCR using Q5 Hot Start DNA polymerase (NEB, M0493L) following manufacturer instructions. Amplified DNA was purified using the DNA Clean and Concentrate Kit (Zymo Research, D4006) and diluted to a concentration of 50 ng/μL. Sequences of the utilized components are listed below, with Gibson assembly sequences being denoted by underlined lowercase text and primers for a given amplicon being listed below the DNA sequence.

```
Gibson assembly overhangs:
pJL1 5' Gibson:
                                                    (SEQ ID NO: 9)
tttgtttaacttttaagaaggagatatacat pJL1 3' Gibson:
                                                    (SEQ ID NO: 10)
gtcgaccggctgctaacaaagcccgaaagg Human IgG1 heavy chain constant 5' Gibson:
                                                    (SEQ ID NO: 11)
gcgtcaacaaaaggtccttcagttttcccattagcccct Human Ig light chain kappa 5' Gibson:
                                                    (SEQ ID NO: 12)
cgcacggtcgcggcgccgtctgtctttattttttcctcct Human Ig light chain lambda 5' Gibson:
                                                    (SEQ ID NO: 13)
ggccaacccaaagcaaacccaactgtcactttgttcccg Linear pJL1 plasmid backbone (Addgene plasmid #69496):
                                                    (SEQ ID NO: 14)
gtcgaccggctgctaacaaagcccgaaaggAAGCTGAGTTGGCTGCTGCCACCGCTGAGC

AATAACTAGCATAACCCCTTGGGGCCTCTAAACGGGTCTTGAGGGGTTTTTTGCTGA

AAGCCAATTCTGATTAGAAAAACTCATCGAGCATCAAATGAAACTGCAATTTATTCA

TATCAGGATTATCAATACCATATTTTTGAAAAAGCCGTTTCTGTAATGAAGGAGAAA

ACTCACCGAGGCAGTTCCATAGGATGGCAAGATCCTGGTATCGGTCTGCGATTCCGA

CTCGTCCAACATCAATACAACCTATTAATTTCCCCTCGTCAAAAATAAGGTTATCAA

GTGAGAAATCACCATGAGTGACGACTGAATCCGGTGAGAATGGCAAAAGCTTATGC

ATTTCTTTCCAGACTTGTTCAACAGGCCAGCCATTACGCTCGTCATCAAAATCACTCG

CATCAACCAAACCGTTATTCATTCGTGATTGCGCCTGAGCGAGACGAAATACGCGAT

CGCTGTTAAAAGGACAATTACAAACAGGAATCGAATGCAACCGGCGCAGGAACACT

GCCAGCGCATCAACAATATTTTCACCTGAATCAGGATATTCTTCTAATACCTGGAAT

GCTGTTTTCCCGGGGATCGCAGTGGTGAGTAACCATGCATCATCAGGAGTACGGATA

AAATGCTTGATGGTCGGAAGAGGCATAAATTCCGTCAGCCAGTTTAGTCTGACCATC

TCATCTGTAACATCATTGGCAACGCTACCTTTGCCATGTTTCAGAAACAACTCTGGC

GCATCGGGCTTCCCATACAATCGATAGATTGTCGCACCTGATTGCCCGACATTATCG

CGAGCCCATTTATACCCATATAAATCAGCATCCATGTTGGAATTTAATCGCGGCTTC

GAGCAAGACGTTTCCCGTTGAATATGGCTCATAACACCCCTTGTATTACTGTTTATGT

AAGCAGACAGTTTTATTGTTCATGATGATATATTTTTATCTTGTGCAATGTAACATCA

GAGATTTTGAGACACAACGTGAGATCAAAGGATCTTCTTGAGATCCTTTTTTTCTGC

GCGTAATCTGCTGCTTGCAAACAAAAAAACCACCGCTACCAGCGGTGGTTTGTTTGC

CGGATCAAGAGCTACCAACTCTTTTTCCGAAGGTAACTGGCTTCAGCAGAGCGCAGA

TACCAAATACTGTTCTTCTAGTGTAGCCGTAGTTAGGCCACCACTTCAAGAACTCTG

TAGCACCGCCTACATACCTCGCTCTGCTAATCCTGTTACCAGTGGCTGCTGCCAGTG

GCGATAAGTCGTGTCTTACCGGGTTGGACTCAAGACGATAGTTACCGGATAAGGCG
```

-continued

CAGCGGTCGGGCTGAACGGGGGGTTCGTGCACACAGCCCAGCTTGGAGCGAACGAC

CTACACCGAACTGAGATACCTACAGCGTGAGCTATGAGAAAGCGCCACGCTTCCCG

AAGGGAGAAAGGCGGACAGGTATCCGGTAAGCGGCAGGGTCGGAACAGGAGAGCG

CACGAGGGAGCTTCCAGGGGGAAACGCCTGGTATCTTTATAGTCCTGTCGGGTTTCG

CCACCTCTGACTTGAGCGTCGATTTTTGTGATGCTCGTCAGGGGGCGGAGCCTATG

GAAAAACGCCAGCAACGCGATCCCGCGAAATTAATACGACTCACTATAGGGAGACC

ACAACGGTTTCCCTCTAGAAATAAT<u>tttgtttaactttaagaaggagatatacat</u> pJL1_F
                                                        (SEQ ID NO: 15)
<u>gtcgaccggctgcta</u> pJL1_R
                                                        (SEQ ID NO: 16)
atgtatatctccttcttaaagttaaacaaaattatttcta Linear sdFab heavy chain constant strepII tagged:
                                                        (SEQ ID NO: 17)
<u>gcgtcaacaaaaggtccttcagttttcccattagcccct</u>TCTTCTAAGTCAACTAGTGGCGGTACT

GCCGCTCTTGGGTGTTTGGTTAAAGATTACTTCCCAGAACCGGTTACGGTCTCGTGG

AACTCTGGTGCACTGACATCGGGCGTACATACATTTCCCGCAGTTTTGCAGTCTTCG

GGACTGTATTCTCTTTCATCGGTGGTTACAGTCCCTAGCTCTTCCCTGGGTACACAGA

CCTACATTTGTAATGTTAATCATAAGCCGAGTAATACTAAGGTGGATAAAAAGGTGG

AACCGAAGTCTTGTGGTGGTGGCGGGTCAGCTCAACTGGAGAAGGAGTTACAGGCA

CTGGAAAAAGAGAATGCTCAACTTGAGTGGGAATTACAGGCGTTAGAAAAAGAACT

GGCCCAGAAGGGTTCTAGCGCATGGTCACATCCCCAGTTCGAAAAATAA<u>gtcgaccggctg</u>

<u>ctaacaaagcccgaaagg</u>

IgGC_F:
                                                        (SEQ ID NO: 18)
GCGTCAACAAAAGGTCCTTCAGTTTTC pJL1_3'Gib_R:
                                                        (SEQ ID NO: 19)
CCTTTCGGGCTTTGTTAGCAGC

Linear sdFab light chain kappa constant
                                                        (SEQ ID NO: 20)
<u>cgcacggtcgcggcgccgtctgtctttattttttcctcct</u>TCTGATGAACAGCTTAAATCTGGGACA

GCTTCTGTTGTATGTTTATTAAACAACTTTTACCCGCGTGAGGCAAAAGTTCAATGG

AAGGTAGACAACGCACTGCAAAGCGGAAATTCGCAGGAGTCAGTTACCGAACAGGA

TTCCAAGGATAGTACCTACTCCTTAAGTTCAACATTAACCCTGTCAAAGGCGGACTA

TGAAAAACATAAGGTATATGCCTGCGAAGTAACTCATCAGGGCTTATCATCCCCAGT

TACAAAATCTTTCAACCGTGGAGAATGCGGCGGCGGAGGTAGCGCGCAGCTTAAGA

AAAAATTGCAAGCCCTTAAAAAAAAAAATGCCCAACTTAAATGGAAGCTGCAAGCC

TTAAAAAAGAAATTGGCGCAGAAGTAA<u>gtcgaccggctgctaacaaagcccgaaagg</u> kLC_F:
                                                        (SEQ ID NO: 21)
TCGCGGCGCCGTCTG pJL1_3'Gib_R:
                                                        (SEQ ID NO: 22)
CCTTTCGGGCTTTGTTAGCAGC

-continued

Linear sdFab light chain lambda 1 constant (SEQ ID NO: 23)

ggccaacccaaagcaaacccaactgtcactttgttcccgCCCTCAAGCGAGGAACTTCAGGCTAA

TAAGGCCACGCTTGTTTGCCTGATCTCAGACTTTTATCCCGGTGCCGTAACAGTGGCT

TGGAAGGCAGATGGTTCGCCGGTCAAAGCGGGCGTGGAAACTACAAAGCCATCGAA

ACAGTCAAACAATAAATATGCGGCATCAAGTTACTTGAGCCTTACCCCAGAACAGT

GGAAGTCACACCGCTCGTACAGTTGTCAAGTTACACACGAGGGAAGTACAGTTGAA

AAGACCGTTGCCCCAACTGAATGTTCAGGCGGTGGTGGCTCAGCGCAGTTAAAGAA

AAAACTGCAGGCTTTGAAGAAAAAGAATGCTCAATTAAAGTGGAAATTGCAGGCGT

TGAAGAAGAAACTTGCGCAGAAGTAAgtcgaccggctgctaacaaagcccgaaagg

1LC_F:

(SEQ ID NO: 24)

GGCCAACCCAAAGCAAAC pJL1_3'Gib_R:

(SEQ ID NO: 25)

CCTTTCGGGCTTTGTTAGCAGC

Gibson assembly was used to assemble protein open reading frame DNA with the pJL1 backbone following the published protocol with the addition 3.125 µg/mL of ET SSB (NEB, product no. M2401 S)[56,57]. 20 ng of purified, linear pJL1 backbone, 20 ng of purified, linear sdFab VH or VL constant DNA, and 20 ng of the protein open reading frame insert were combined in 2 µL Gibson assembly reactions and incubated at 50° C. for 30 minutes. The unpurified assembly reactions were diluted in 40 µL of nuclease free water (Fisher Scientific, AM9937) and 1 µL of the diluted reaction were used as the template for a PCR to generate linear expression templates (LETs) for CFPS. Linear expression templates were amplified via PCR using the pJL1_LET_F (ctgagatacctacagcgtgagc, (SEQ ID NO: 26)) and pJL1_LET_R (cgtcactcatggtgatttctcacttg, (SEQ ID NO: 27)) primers and the Q5 Hot Start DNA polymerase (NEB, M0493L) following manufacturer instructions.

Additional Protein DNA Sequence

The DNA sequence of the *P. pyralis* luciferase containing a c-terminal strepII tag (fLuc, Uniprot Q27758) used as a negative control is below and was cloned into the pJL1 vector.

(SEQ ID NO: 28)

atggaagacgctaagaacattaagaagggacctgctccattctacccc tcgaagacggcactgcaggtgagcagcttcataaagcgatgaagcgtta tgcgttagttcctggcacgatcgccttcactgacgcgcacatcgaagtc aatatcacctacgctgaatactttgagatgagtgtgcgtctggcggaag ccatgaagcgttatggccttaacacgaaccaccgcatcgttgtttgtag cgagaattccttacaattcttcatgcccgtccttggcgcgctgtttatt ggtgtggccgttgcaccagccaatgacatctataatgagcgcgagttgt tgaactccatgaacatttctcaaccaacagtggtgttcgtttcaaagaa aggcttacagaaaatcttaaacgttcaaaagaaactgccgattatccag aagatcatcattatggatagtaagactgactaccagggcttccagtcaa tgtatacattcgtgacgagtcacctgcccccgggttttaacgagtacga -continued ctttgtcccagagagctttgatcgcgacaagaccatcgccctcattatg aatagcagtggttcgacgggtagcccaaagggagtggccctgccccatc gtaccgcgtgcgtccgtttctcccatgcccgcgacccaattttcggcaa tcaaatcatccccgacacggcaatcttgtcggtcgtcccgtttcaccat ggctttggaatgtttacgacactcggttacctcatctgcggtttccgcg tcgttctgatgtatcgcttcgaggaagagttgttcttacgttcgcttca ggactacaagattcaatccgcccttctggtccccactttgttcagtttc tttgctaagagcaccttaattgataagtatgacctctccaacttacacg agattgcgagcggtggtgctcccctcagcaaagaggttggagaggcggt tgctaagcgttttcatctgcccggtatccgtcaaggttacggcctcacc gaaaccacttctgccattcttatcactccggaaggtgacgataagcctg gggcagtgggtaaagttgtacccttcttcgaggctaaggttgtggattt agatacggggaagaccttaggtgtgaaccagcgcggtgaactgtgcgtt cgcggtccgatgattatgtcggggttatgttaatgaccccgaggctacga acgcgcttatcgataaggacggttggcttcattccggcgacatcgctta ctgggatgaggatgagcacttcttcatcgttgaccgtctgaagagtctc atcaagtataaaggatgtcaagtcgctccggcagagttagagagcatct tactccagcaccctaatatcttcgatgctggggttgccgggctcccagg cgacgatgccggcgagctgccggcggcggtagttgttttagagcatggc aagaccatgaccgaaaggagattgtagactacgtcgcgagtcaagtaa ccacagcgaagaagctccgcggtggagtggtctttgttgacgaggtgcc taaaggcctgacgggcaaacttgacgcgcgtaagatccgtgagatcctc atcaaagcgaagaagggtgggaagagtaagctggggagttcaggttggt cccacccgcaatttgagaagtga Cell Extract Preparation for Cell-Free Protein Synthesis

*E. coli* Origami™ B(DE3) (Novagen, 70837) extracts were prepared using a modified version of established protocols[58,59]. Briefly, one 150 mL Origami™ B(DE3)

starter cultures were inoculated in LB from a glycerol stock and cultured in a 250 mL baffled flask at 37° C. for 16 hours. The 2×YTP was prepared lacking glucose in 75% of the final volume and sterilized using an autoclave. A 4× glucose solution was prepared and autoclaved separately, then added to the medium immediately prior to use. The starter cultures were used to inoculate 1 L of 2×YTPG media (16 g/L tryptone, 10 g/L yeast extract, 5 g/L sodium chloride, 7 g/L potassium phosphate dibasic, 3 g/L potassium phosphate monobasic, 18 g/L glucose) in a 2.5 L Full-Baffle Tunair shake flask at an initial OD600 of 0.08. Cells were cultured at 37° C. with at 220 RPM in a shaking incubator. Cultures were grown until OD600 0.4-0.6, at which point the expression of T7 RNA polymerase was induced by the addition of IPTG to a final concentration of 0.5 mM. Cells were harvested at an OD600 of 2.5 via centrifugation at 12,000 g for 1 minute at 4° C. Cell pellets were washed three times with 25 mL S30 buffer per 50 mL culture (10 mM Tris Acetate pH 8.2, 14 mM Magnesium Acetate, and 60 mM Potassium Acetate). Pellets were resuspended in 1 mL S30 buffer per gram of cell mass. Cell suspensions were lysed using a single pass on an Avestin EmulsiFlex-B15 Homogenizer at a lysis pressure of 24,000 PSI. Cell debris was separated via centrifugation at 18,000 g for 20 minutes, and the clarified lysate was collected, flash frozen in liquid nitrogen, and stored at −80° C.

DsbC and FkpA Expression and Purification

Protein expression, purification, and his tag removal was performed in a similar manner to previously reported[60]. DsbC (Uniprot POAEG6, residues 21-236) and FkpA (Uniprot P45523, residues 26-270) were ordered as gBlocks from IDT containing a c-terminal, TEV cleavable his tag (GSENLYFQSGSHHHHHHHHHH, (SEQ ID NO: 29)) and cloned into pET28a. Plasmids were transformed into BL21 Star DE3, plated on LB agar, and cultured overnight at 37° C. 1 L of Overnight Express TB (Fisher Scientific, 71491-4) was inoculated by scraping all colonies on a transformation plate and cultured at 37° C. in 2.5 L tunair flasks (IBI Scientific, SS-8003) at 220 rpm overnight. Cells were harvested, resuspended at a ratio of 1 g cell mass to 4 mL resuspension buffer (50 mM HEPES pH 7.5, 500 mM NaCl, 1×HALT protease inhibitor without EDTA (Fisher Scientific, 78429), 1 mg/mL lysozyme, 62.5 U/mL cell suspension of benzonase (Sigma Aldrich, E1014-25KU)) and lysed using an Avestin B15 homogenizer at 24,000 PSI. Lysate was spun down 14,000×g for 10 min and the clarified supernatant was incubated with Ni-NTA Agarose (Qiagen, 30230) for 60 min on an end-over-end shaker. Resin was spun down 2,500×g for 2 min, supernatant removed, resuspended in wash buffer (50 mM HEPES pH 7.5, 500 mM NaCl, 50 mM Imidazole), loaded on a gravity flow column, and subsequently washed with 20× resin volumes of wash buffer. Protein was eluted using elution buffer (50 mM HEPES pH 7.5, 500 mM NaCl, 500 mM Imidazole) and exchanged into 50 mM HEPES pH 7.4, 150 mM NaCl using PD-10 desalting columns (Cytvia, 17-0851-01) according to manufacturer instructions.

His tags were removed via cleavage by ProTEV Plus (Promega, V6102). Prior to cleavage, 10% v/v glycerol was added to the protein. ProTEV Plus was added to a concentration of 0.5 U/μg purified protein and DTT was added to a concentration of 1 mM. Cleavage reactions were carried out at 30° C. for 4 h. Free His tag and ProTEV Plus were removed by incubating with Ni-NTA Agarose for 1 hour at 4° C. and collecting the supernatant. Proteins were subsequently concentrated to >1 mg/mL (Millipore, UFC800396).

His tag removal was validated via SDS-PAGE and the AlphaScreen Histidine (Nickel Chelate) Detection Kit (Perkin Elmer, 6760619C).

Cell-Free Protein Synthesis

CFPS reactions were composed of the following reagents: 8 mM magnesium glutamate, 10 mM ammonium glutamate, 130 mM potassium glutamate, 1.2 mM ATP, 0.5 mM of each CTP, GTP, and UTP. 0.03 mg/mL folinic acid, 0.17 mg/mL E. coli MRE600 tRNA (Roche 10109541001), 100 mM NAD, 50 mM CoA, 4 mM oxalic acid, 1 mM putrescine, 1 mM spermidine, 57 mM HEPES pH 7.2, 2 mM of each amino acid, 33.3 mM PEP, 20% v/v E. coli extract, varying concentrations of DNA template, and the remainder water. The preparation of these reagents has been described in detail elsewhere[61]. For DNA templates, plasmids were used at a concentration of 8 nM and unpurified linear PCR product were used at 6.66% v/v. For the expression of antibodies, each template was added to a final concentration of 6.66% v/v. For antibody and sdFab expression 4 mM oxidized glutathione, 1 mM reduced glutathione, 14 μM of purified DsbC, and 50 μM FkpA were also supplemented to the reactions. Additionally, for cell-extracts were treated with 50 mM iodoacetamide (IAM) at room temperature for 30 minutes prior to use in CFPS[62]. All reaction components were assembled on ice and were either run as 12 μL reactions in 1.5 mL microtubes or 2 μL reactions in 384 well plates (BioRad, HSP3801). For 2 μL reactions, components were transferred to the plate using an Echo 525 acoustic liquid handler. A mix containing all the CFPS components except for the DNA was dispensed from 384PP Plus plates (Labcyte, PPL-0200) using the BP setting. The DNA (unpurified PCR products) was dispensed from a 384LDV Plus plate (Labcyte, LPL-0200) using the GP setting. Reactions were allowed to proceed at 30° C. for 20 hours.

To quantify sfGFP fluorescence, a standard curve was prepared using previously reported methods[59]. Radioactive leucine was added to CFPS at a final concentration of 10 μM of L-[14C(U)]-leucine (Perkin Elmer NEC279E250UC, 11.1GBq/mMole), followed by precipitation of the expressed proteins and scintillation counting[63]. To quantify sfGFP fluorescence, 2 μL of a CFPS reaction was diluted in 48 μL of water in a Black Costar 96 Well Half Area Plate. Fluorescence was measured using a BioTek Synergy™ H1 plate reader with excitation and emission wavelengths of 485 and 528 respectively. Scintillation counts and fluorescence were fit to determine a standard curve for use with non-radioactive samples.

To visualize antibody assembly, proteins were labeled during CFPS with the FluoroTect™ (Promega, L5001). FluoroTect™ was included in the CFPS reaction at 3.33% v/v. After protein synthesis, RNAseA (Omega Bio-Tek, AC118) was added to 0.1 mg/mL and the sample was incubated at 37° C. for 10 minutes. Samples were subsequently denatured at 70° C. for 3 minutes, then separated via SDS-PAGE and imaged using a LI-COR Odyssey Fc imager on the 600 channel.

AlphaLISA Reaction

AlphaLISA reactions were carried out in 50 mM HEPES pH 7.4, 150 mM NaCl, 1 mg/mL BSA, and 0.015% v/v TritonX-100 (hereafter referred to as Alpha buffer). All components were dispensed using an Echo 525 liquid handler from a 384-Well Polypropylene 2.0 Plus microplate (Labcyte, PPL-0200) using the 384PP_Plus_GPSA fluid type. All components of the AlphaLISA reactions were prepared as 4× stocks and added as 0.5 μL to the final 2 μL reaction to achieve the desired concentration. All AlphaLISA reactions were performed with CFPS reactions diluted to a final concentration of 2.5% v/v. AlphaLISA beads were combined to prepare a 4× stock in Alpha buffer immediately prior to use and added to the proteins to yield a concentration of 0.08 mg/mL donor beads and 0.02 mg/mL acceptor beads in the final reaction. All reactions were incubated with AlphaLISA beads for 1 hour prior to measurement. AlphaLISA measurements were taken on a Tecan Infinite M1000 Pro plate reader using the AlphaLISA filter with an excitation time of 100 ms, an integration time of 300 ms and a settle time 20 ms. Prior to measurement, plates were allowed to equilibrate inside the instrument for 10 min. For measurements involving sdFabs, protein A AlphaLISA beads were avoided due to the ability of protein A to bind human subgroup VH3 Fabs[64].

The impact of CFPS reagents on AlphaLISA was determined by serially diluting the specified reagents in Alpha buffer and combining them with the specified AlphaLISA conditions. The TrueHits kit (Perkin Elmer, AL900) was used to assess the impact of the CFPS reagents on the Alpha detection chemistry. CFPS reagents were mixed with the donor and acceptor beads and incubated for 2 hours prior to measurement. His tagged RBD (Sino Biological, 40592-V08H) and human FC tagged human ACE2 (GenScript, Z03484) were used to evaluate the impact of CFPS reagents on capture chemistries. RBD and ACE2 were diluted in Alpha buffer and mixed at a final reaction concentration of 10 nM each and combined with the CFPS reagents and allowed to incubate for 1 hour, Donor and acceptor beads were subsequently added and allowed to incubate for a further hour prior to measurement. Protein A Alpha donor beads (Perkin Elmer, AS 102), NiChelate AlphaLISA acceptor beads (Perkin Elmer, AL108), and anti-6×his AlphaLISA acceptor beads (Perkin Elmer, AL178) were utilized for detection.

The commercial neutralizing antibody ACE2 competition experiment was performed with the following antibodies: nAb 1(Acro Biosystems, SAD-535), nAb2 (Sino Biological, 40592-MM57), nAb3 (Sino Biological, 40591-MM43), nAb4 (Sino Biological, 40592-R001). ELISA IC$_{50}$ values were recorded from the product page at the time of purchase and converted to µg/mL assuming a MW of 150,000 Da if reported in M. Antibodies were serially diluted in Alpha buffer and mixed with SARS-CoV-2 RBD (Sino Biological, 40592-V02H) at a concentration of 10 nM in the final reaction and incubated for 1 hour. Mouse FC tagged human ACE2 (Sino Biological, 10108-H05H) was subsequently added and incubated for 1 hour, followed by simultaneous addition of the acceptor and donor beads. AlphaLISA detection was performed using Anti-Mouse IgG Alpha Donor beads (PerkinElmer, AS104) and Strep-Tactin AlphaLISA Acceptor beads (PerkinElmer, AL136). IC$_{50}$ values were calculated using Prism 9 by fitting the normalized data to [Inhibitor] vs. response—Variable slope (four parameters) fit with the max constrained to a value of 1.

Assembly AlphaLISA reactions were composed of a final concentration of 10 nM of either Rabbit Anti-Human kappa light chain antibody (abcam, ab125919) or Rabbit Anti-Human lambda light chain (abcam, ab124719). AlphaLISA detection was performed using Anti-Rabbit IgG Alpha Donor beads (PerkinElmer, AS105) and Strep-Tactin AlphaLISA Acceptor beads (PerkinElmer, AL136). CFPS reaction containing the expressed sdFab of interest was mixed with the appropriate anti-light chain antibody and allowed to equilibrate for two hours prior to the simultaneous addition of the acceptor and donor beads.

SARS-CoV-2 S trimer binding AlphaLISA reactions were composed of a final concentration of 5 nM His-tagged SARS-CoV-2 S trimer (Acro Biosystems, SPN-052H9). AlphaLISA detection was performed using Strep-Tactin Alpha Donor beads (PerkinElmer, AS106) and Anti-6×His AlphaLISA Acceptor beads (PerkinElmer, AL178). CFPS reaction containing the expressed sdFab of interest was mixed with the S trimer and allowed to equilibrate for two hours prior to the simultaneous addition of the acceptor and donor beads.

SARS-CoV-2 RBD binding AlphaLISA reactions were composed of a final concentration of 5 nM Human Fe-tagged SARS-CoV-2 RBD (Sino Biological, 40592-V02H). AlphaLISA detection was performed using Anti-Human IgG Alpha Donor beads (PerkinElmer, AS114) and Strep-Tactin AlphaLISA Acceptor beads (PerkinElmer, AL136). CFPS reaction containing the expressed sdFab of interest was mixed with the RBD and allowed to equilibrate for two hours prior to the simultaneous addition of the acceptor and donor beads.

ACE2 and RBD competition AlphaLISA reactions were composed of a final concentration of 2 nM Biotinylated SARS-CoV-2 S trimer (Acro Biosystems, SPN-C82E9) and 2 nM Human FC-tagged human ACE2 (GenScript, Z03484). AlphaLISA detection was performed using Anti-Human IgG Alpha Donor beads (PerkinElmer, AS 114) and Anti-6×His AlphaLISA Acceptor beads (PerkinElmer, AL178). CFPS reaction containing the expressed sdFab of interest was first mixed with S trimer and allowed to incubate for 1 hour. Subsequently, ACE2 was added and allowed to equilibrate for a further 1 hour prior to the simultaneous addition of the acceptor and donor beads.

Data Analysis

Statistical analyses were performed in python. Two-sided t-tests were performed using the scipy package and the Benjamini and Hochberg False Discovery Rate procedure[49] was performed using the statsmodels package with a family wise error rate of 5%. For t-tests, the following samples were considered to be background and the combined data were used in the t-test. Assembly: No DNA and Buffer controls. S trimer binding: No DNA and Buffer controls. RBD binding: No DNA and Buffer controls. ACE2 competition: No DNA and αHER2.

TABLE 1

| # | ID | Brand Name | LC Class | DOI | PDB | Reported RBD Binding | Reported ACE2 Competition | Reported Pseudo-virus Neutralization IC50 (µg/mL) | Reported Authentic Virus Neutralization IC50 (µg/mL) | Lowest Neutralization IC50 (µg/mL) | Reported KD(M) | Notes |
|---|---|---|---|---|---|---|---|---|---|---|---|---|
| 1 | αHER2 | Trastuzumab | Kappa | 10.1038/nprot.2017,126 | NA | No | No | NA | NA | NA | NR | |

TABLE 1-continued

| # | ID | Brand Name | LC Class | DOI | PDB | Reported RBD Binding | Reported ACE2 Competition | Reported Pseudovirus Neutralization IC50 (μg/mL) | Reported Authentic Virus Neutralization IC50 (μg/mL) | Lowest Neutralization IC50 (μg/mL) | Reported KD(M) | Notes |
|---|---|---|---|---|---|---|---|---|---|---|---|---|
| 2 | 4A8 | NA | Kappa | 10.1126/science.abc6952 | 7C2L | No | No | 4.90E+01 | 6.10E-01 | 6.10E-01 | 1.00E-09 | Targets the SARS-CoV-2 n-terminal domian |
| 3 | CR3022 | NA | Kappoa | 10.1126/science.abb7269 | 6W41 | Yes | No | NA | NA | NA | <1E-10 | Binding to S trimer sterically hindered |
| 4 | CV07-270 | NA | Lambda | 10.1016/j.cell.2020.09.040 | 6XKP | Yes | No | NR | 8.23E-02 | 8.23E-02 | NR | |
| 5 | S309 | Sotrovimab | Kappa | 10.1038/s41586-020-2349-y | 6WPS | Yes | No | 5.25E-01 | 7.90E-02 | 7.90E-02 | <1E-12 | |
| 7 | C135 | NA | Kappa | 10.1038/s41586-020.2852-1 | 7K8R | Yes | No | 1.66E-02 | NR | 1.66E-02 | NR | |
| 8 | BD23 | NA | Kappa | 10.1016/j.cell.2020.05.025 | 7BYR | Yes | Yes | 4.80E+00 | 8.50E+00 | 4.80E+00 | 4.30E-09 | |
| 9 | S2A4 | NA | Lambda | 10.1016/j.cell.2020.09.037 | 7JVA | Yes | Yes | 3.50E+00 | NR | 3.50E+00 | NR | |
| 10 | S2H14 | NA | Lambda | 10.1016/j.cell.2020.09.037 | 7JXC | Yes | Yes | 9.00E-01 | NR | 9.00E-01 | NR | |
| 11 | H4 | NA | Kappa | 10.1126/science.abc2241 | NR | Yes | Yes | NR | 8.96E-01 | 8.96E-01 | 4.5E-09 | |
| 12 | S304 | NA | Kappa | 10.1016/j.cell.2020.09.037 | 73W0 | Yes | Yes | 5.00E-01 | NR | 5.00E-01 | NR | |
| 13 | S2H13 | NA | Lambda | 10.1016/j.cell.2020.09.037 | 7JV2 | Yes | Yes | 5.00E-01 | NR | 5.00E-01 | NR | |
| 14 | S2X35 | NA | Lambda | 10.1016/j.cell.2020.09.037 | 7JXE | Yes | Yes | 5.00E-01 | NR | 5.00E-01 | NR | |
| 15 | B38 | NA | Kappa | 10.1126/science.abc2241 | 7BZ5 | Yes | Yes | NR | 1.77E-01 | 1.77E-01 | 7E-08 | |
| 16 | 2-4 | NA | Lambda | 10.1038/s41586-020-2571-7 | 6XEY | Yes | Yes | 3.94E-01 | 5.70E-02 | 5.70E-02 | NR | |
| 17 | P2B-2F6 | NA | Lambda | 10.1038/s41586-020-2380-z | 7BWJ | Yes | Yes | 5.00E-02 | 4.10E-01 | 5.00E-02 | 5.1E-09 | |
| 18 | BD-236 | NA | Kappa | 10.1016/j.cell.2020.05.025 | 7CHB | Yes | Yes | 3.70E-02 | 3.20E-01 | 3.70E-02 | 2.80E-09 | |
| 19 | C86 | Eresevimab | Kappa | 10.1038/s41386-020-2381-y | 7C01 | Yes | Yes | 4.10E-02 | 3.60E-02 | 3.60E-02 | 2.49E-09 | |

TABLE 1-continued

| # | ID | Brand Name | LC Class | DOI | PDB | Reported RBD Binding | Reported ACE2 Competition | Reported Pseudo-virus Neutral-ization IC50 (µg/mL) | Reported Authentic Virus Neutral-ization IC50 (µg/mL) | Lowest Neutral-ization IC50 (µg/mL) | Reported KD(M) | Notes |
|---|---|---|---|---|---|---|---|---|---|---|---|---|
| 20 | C102 | NA | Kappa | 10.1038/ s41586-020-2852-1 | 7K8N | Yes | Yes | 3.40E−02 | NR | 3.40E−02 | NR | |
| 21 | C105 | NA | Lambda | 10.1016/ j.cell. 2020. 06.025 | 6XCA | Yes | Yes | 2.60E−02 | NR | 2.60E−03 | NR | |
| 22 | C104 | NA | Kappa | 10.1038/ s41586-020-2852-1 | 7K8U | Yes | Yes | 2.33E−02 | NR | 2.33E−02 | NR | |
| 23 | CC123 | NA | Kappa | 10.1126/ science. abd2321 | 6XC4 | Yes | Yes | 2.20E−02 | NR | 2.20E−02 | NR | |
| 24 | CC12.1 | NA | Kappa | 10.1126/ science. abd2321 | 6XC2 | Yes | Yes | 1.90E−02 | NR | 1.90E−02 | NR | |
| 6 | C110 | NA | Kappa | 10.1038/ s41586-020-2852-1 | 7K8P | Yes | Yes | 1.84E−02 | NR | 1.84E−02 | NR | Not direct binding overlap w/ ACE2, but likely stearic clash |
| 25 | C119 | NA | Lambda | 10.1038/ s41586-020-2852-1 | 7K8W | Yes | Yes | 9.10E−03 | NR | 9.10E−03 | NR | |
| 26 | C002 | NA | Kappa | 10.1038/ s415866-020-2852-1 | 7K8O | Yes | Yes | 8.90E−03 | NR | 8.90E−03 | NR | |
| 27 | COVA2-15 | NA | Kappa | 10.1126/ science. abc5902 | NR | Yes | Yes | 5.00E−03 | 9.00E−03 | 6.00E−03 | 3.10E−09 | |
| 28 | COVA1-18 | NA | Lambda | 10.1126/ science. abc5902 | NR | Yes | Yes | 8.00E−03 | 7.00E−03 | 7.00E−03 | 9.00E−10 | |
| 29 | C144 | NA | Lambda | 10.1038/ s41586-020-2852-1 | 7K90 | Yes | Yes | 6.90E−03 | NR | 6.90E−03 | NR | |
| 30 | C121 | NA | Lambda | 10.1038/ s41586-020-2852-1 | 7KBO | Yes | Yes | 6.20E−03 | NR | 6.30E−03 | NR | |
| 31 | BD-629 | NA | Kappa | 10.1016/ j.cell. 2020. 09.035 | 7CHS | Yes | Yes | 6.10E−03 | 5.80E−02 | 6.10E−03 | NR | |
| 32 | REGN10987 | Casirivimab | Lambda | 10.1126/ science. abd0827 | 6XDG | Yes | Yes | 6.00E−03 | 6.30E−03 | 6.00E−03 | 3E−11 | Not direct binding overlap w/ ACE2, but likely stearic clash |
| 33 | REGN10933 | Imdevimab | Kappa | 10.1126/ science. abd0827 | 6XDG | Yes | Yes | 6.40E−03 | 5.60E−03 | 5.60E−03 | 1.40E−11 | |
| 34 | BD-604 | NA | Kappa | 10.1016/ j.cell. 2020. 09.035 | 7CH4 | Yes | Yes | 4.80E−03 | 4.30E−02 | 4.80E−03 | NR | |

TABLE 1-continued

| # | ID | Brand Name | LC Class | DOI | PDB | Reported RBD Binding | Reported ACE2 Competition | Reported Pseudo-virus Neutral-ization IC50 (µg/mL) | Reported Authentic Virus Neutral-ization IC50 (µg/mL) | Lowest Neutral-ization IC50 (µg/mL) | Reported KD(M) | Notes |
|---|---|---|---|---|---|---|---|---|---|---|---|---|
| 35 | CV07-250 | NA | Lambda | 10.1016/ j.cell. 2020. 09.049 | 6XKQ | Yes | Yes | NR | 3.50E−03 | 3.50E−03 | 5.64E−11 | |
| 36 | S2B12 | NA | Kappa | 10.1126/ science. abc3354 | 7K3O | Yes | Yes | 2.50E−03 | 6.00E−03 | 2.50E−03 | NR | |
| 37 | S2M11 | NA | Kappa | 10.1126/ science. abc3354 | 7K43 | Yes | Yes | 195E−03 | 3.00E−03 | 1.95E−03 | NR | |
| 38 | BD.368-2 | NA | Kappa | 10.1016/ j.cell .2020. 05.025 | 7CHF | Yes | Yes | 1.50E−02 | 1.20E−03 | 1.20E−03 | 8.20E−10 | |

Notes:
NR indicates not reported
NA indicates applicable

TABLE 2

| # | ID | LC Class | DOI | Reported ELISA S trimer (AUC) | Reported ELISA RBD (AUC) | Reported Pseudovirus Neutralization (µg/mL) | Reported ACE2 Competition? | Notes |
|---|---|---|---|---|---|---|---|---|
| 1 | COVA1-01 | Kappa | 10.1126/ science. abc5902 | 5.62 | 0.52 | >10 | NR | |
| 2 | COVA1-02 | Lambda | 10.1126/ science. abc5902 | 4.02 | 0.54 | >10 | NR | |
| 3 | COVA1-03 | Kappa | 10.1126/ science. abc5902 | 0.76 | 0.53 | 0.42 | No | |
| 4 | COVA1-04 | Kappa | 10.1126/ science. abc5902 | 0.69 | 0.46 | >10 | NR | |
| 5 | COVA1-05 | Lambda | 10.1126/ science. abc5902 | 0.58 | 0.49 | >10 | NR | |
| 6 | COVA1-06 | Lambda | 10.1126/ science. abc5902 | 2.49 | 0.46 | >10 | NR | |
| 7 | COVA1-07 | Kappa | 10.1126/ science. abc5902 | 9.54 | 1.30 | >10 | NR | |
| 8 | COVA1-08 | Lambda | 10.1126/ science. abc5902 | 3.22 | 11.31 | >10 | NR | |
| 9 | COVA1-09 | Kappa | 10.1126/ science. abc5902 | 6.53 | 0.47 | >10 | NR | |
| 10 | COVA1-10 | Lambda | 10.1126/ science. abc5902 | 0.72 | 5.22 | >10 | NR | |
| 11 | COVA1-11 | Lambda | 10.1126/ science. abc5902 | 0.54 | 0.56 | >10 | NR | |
| 12 | COVA1-12 | Lambda | 10.1126/ science. abc5902 | 4.14 | 12.99 | 1.3 | NR | |
| 13 | COVA1-13 | Kappa | 10.1126/ science. abc5902 | 0.48 | 0.44 | >10 | NR | |
| 14 | COVA1-14 | Kappa | 10.1126/ science. abc5902 | 0.54 | 0.47 | >10 | NR | |

TABLE 2-continued

| # | ID | LC Class | DOI | Reported ELISA S trimer (AUC) | Reported ELISA RBD (AUC) | Reported Pseudovirus Neutralization (μg/mL) | Reported ACE2 Competition? | Notes |
|---|-----|----------|-----|---------|---------|-----------|---------|-------|
| 15 | COVA1-15 | Lambda | 10.1126/ science. abc5902 | 0.47 | 0.47 | >10 | NR | |
| 16 | COVA1-16 | Kappa | 10.1126/ science. abc5902 | 7.64 | 12.68 | 0.13 | Yes | |
| 17 | COVA1-17 | Lambda | 10.1126/ science. abc5902 | 0.53 | 0.56 | >10 | NR | |
| 18 | COVA1-18 | Lambda | 10.1126/ science. abc5902 | 10.22 | 15.74 | 0.008 | Yes | |
| 19 | COVA1-19 | Kappa | 10.1126/ science. abc5902 | 11.09 | 0.45 | >10 | NR | |
| 20 | COVA1-20 | Lambda | 10.1126/ science. abc5902 | 4.91 | 0.47 | >10 | NR | |
| 21 | COVA1-21 | Kappa | 10.1126/ science. abc5902 | 1.29 | 0.47 | 0.040 | No | |
| 22 | COVA1-22 | Lambda | 10.1126/ science. abc5902 | 7.32 | 0.46 | 0.18 | No | |
| 23 | COVA1-23 | Lambda | 10.1126/ science. abc5902 | 0.93 | 0.53 | >10 | NR | |
| 24 | COVA1-24 | Lambda | 10.1126/ science. abc5902 | 0.58 | 0.51 | >10 | NR | |
| 25 | COVA1-25 | Kappa | 10.1126/ science. abc5902 | 3.09 | 0.48 | 0.18 | NR | |
| 26 | COVA1-26 | Kappa | 10.1126/ science. abc5902 | 1.85 | 0.43 | >10 | NR | |
| 27 | COVA1-27 | Kappa | 10.1126/ science. abc5902 | 5.89 | 0.46 | >10 | NR | |
| 28 | COVA2-01 | Kappa | 10.1126/ science. abc5902 | 0.95 | 9.65 | >10 | NR | |
| 29 | COVA2-02 | Kappa | 10.1126/ science. abc5902 | 8.45 | 13.63 | 3.1 | NR | |
| 30 | COVA2-03 | Kappa | 10.1126/ science. abc5902 | 6.53 | 0.57 | >10 | NR | |
| 31 | COVA2-04 | Kappa | 10.1126/ science. abc5902 | 8.52 | 13.54 | 0.22 | NR | |
| 32 | COVA2-05 | Kappa | 10.1126/ science. abc5902 | 7.42 | 12.86 | 5.7 | NR | |
| 33 | COVA2-06 | Kappa | 10.1126/ science. abc5902 | 0.67 | 0.49 | >10 | NR | |
| 34 | COVA2-07 | Kappa | 10.1126/ science. abc5902 | 8.56 | 13.58 | 0.029 | Yes | |
| 35 | COVA2-08 | Kappa | 10.1126/ science. abc5902 | 0.70 | 0.71 | >10 | NR | |
| 36 | COVA2-09 | Kappa | 10.1126/ science. abc5902 | 0.78 | 0.52 | >10 | NR | |
| 37 | COVA2-10 | Kappa | 10.1126/ science. abc5902 | 6.27 | 0.47 | >10 | NR | |
| 38 | COVA2-11 | Kappa | 10.1126/ science. abc5902 | 3.94 | 12.35 | 3.7 | NR | |
| 39 | COVA2-12 | Kappa | 10.1126/ science. abc5902 | 6.42 | 0.49 | >10 | NR | |

TABLE 2-continued

| # | ID | LC Class | DOI | Reported ELISA S trimer (AUC) | Reported ELISA RBD (AUC) | Reported Pseudovirus Neutralization (μg/mL) | Reported ACE2 Competition? | Notes |
|---|---|---|---|---|---|---|---|---|
| 40 | COVA2-13 | Kappa | 10.1126/ science. abc5902 | 1.94 | 10.03 | 3.2 | NR | |
| 41 | COVA2-14 | Kappa | 10.1126/ science. abc5902 | 3.05 | 0.57 | >10 | NR | |
| 42 | COVA2-15 | Kappa | 10.1126/ science. abc5902 | 9.43 | 14.74 | 0.008 | Yes | |
| 43 | COVA2-16 | Kappa | 10.1126/ science. abc5902 | 1.46 | 4.08 | >10 | NR | |
| 44 | COVA2-17 | Kappa | 10.1126/ science. abc5902 | 11.61 | 12.54 | 0.053 | No | |
| 45 | COVA2-18 | Kappa | 10.1126/ science. abc5902 | 2.36 | 0.44 | >10 | NR | |
| 46 | COVA2-19 | Kappa | 10.1126/ science. abc5902 | 0.46 | 0.6: | >10 | NR | |
| 47 | COVA2-20 | Kappa | 10.1126/ science. abc5902 | 8.27 | 13.14 | 0.73 | NR | |
| 48 | COVA2-21 | Kappa | 10.1126/ science. abc5902 | 0.55 | 0.54 | >10 | NR | |
| 49 | COVA2-22 | Kappa | 10.1126/ science. abc5902 | 1.51 | 0.49 | >10 | NR | |
| 50 | COVA2-23 | Kappa | 10.1126/ science. abc5902 | 5.27 | 14.99 | >10 | NR | |
| 51 | COVA2-24 | Kappa | 10.1126/ science. abc5902 | 4.19 | 16.21 | >10 | NR | |
| 52 | COVA2-25 | Lambda | 10.1126/ science. abc5902 | 7.75 | 0.40 | >10 | NR | |
| 53 | COVA2-26 | Lambda | 10.1126/ science. abc5902 | 5.94 | 0.64 | >10 | NR | |
| 54 | COVA2-27 | Lambda | 10.1126/ science. abc5902 | 1.16 | 1.28 | >10 | NR | |
| 55 | COVA2-28 | Kappa | 10.1126/ science. abc5902 | 10.34 | 0.43 | >10 | NR | |
| 56 | COVA2-29 | Kappa | 10.1126/ science. abc5902 | 10.91 | 13.49 | 0.092 | NR* | ** |
| 57 | COVA2-30 | Lambda | 10.1126/ science. abc5902 | 3.74 | 0.47 | >10 | NR | |
| 58 | COVA2-31 | Kappa | 10.1126/ science. abc5902 | 9.62 | 16.89 | >10 | NR | |
| 59 | COVA2-32 | Kappa | 10.1126/ science. abc5902 | 2.32 | 1.01 | >10 | NR | |
| 60 | COVA2-33 | Lambda | 10.1126/ science. abc5902 | 8.16 | 0.52 | >10 | NR | |
| 61 | COVA2-34 | Lambda | 10.1126/ science. abc5902 | 2.60 | 0.35 | >10 | NR | |
| 62 | COVA2-35 | Lambda | 10.1126/ science. abc5902 | 0.59 | 0.46 | >10 | NR | |
| 63 | COVA2-36 | Kappa | 10.1126/ science. abc5902 | 0.53 | 5.56 | >10 | NR | |
| 64 | COVA2-37 | Lambda | 10.1126/ science. abc5902 | 10.42 | 0.90 | 4.0 | NR | |

TABLE 2-continued

| # | ID | LC Class | DOI | Reported ELISA S trimer (AUC) | Reported ELISA RBD (AUC) | Reported Pseudovirus Neutralization (µg/mL) | Reported ACE2 Competition? | Notes |
|---|---|---|---|---|---|---|---|---|
| 65 | COVA2-38 | Kappa | 10.1126/ science. abc5902 | 10.22 | 0.63 | >10 | NR | |
| 66 | COVA2-39 | Lambda | 10.1126/ science. abc5902 | 11.57 | 15.52 | 0.036 | Yes | |
| 67 | COVA2-40 | Lambda | 10.1126/ science. abc5902 | 6.79 | 0.36 | >10 | NR | |
| 68 | COVA2-41 | Kappa | 10.1126/ science. abc5902 | 9.72 | 0.51 | >10 | NR | |
| 69 | COVA2-42 | Kappa | 10.1126/ science. abc5902 | 0.98 | 0.50 | >10 | NR | |
| 70 | COVA2-43 | Kappa | 10.1126/ science. abc5902 | 10.20 | 0.46 | >10 | NR | |
| 71 | COVA2-44 | Kappa | 10.1126/ science. abc5902 | 6.58 | 12.07 | >10 | NR | |
| 72 | COVA2-45 | Kappa | 10.1126/ science. abc5902 | 1.81 | 11.82 | >10 | NR | |
| 73 | COVA2-46 | Kappa | 10.1126/ science. abc5902 | 5.92 | 11.90 | >10 | NR | |
| 74 | COVA2-47 | Kappa | 10.1126/ science. abc5902 | 1.53 | 0.50 | >10 | NR | |
| 75 | COVA3-01 | Kappa | 10.1126/ science. abc5902 | 1.12 | 0.54 | >10 | NR | |
| 76 | COVA3-02 | Lambda | 10.1126/ science. abc5902 | 0.65 | 0.50 | >10 | NR | |
| 77 | COVA3-03 | Lambda | 10.1126/ science. abc5902 | 3.06 | 0.88 | >10 | NR | |
| 78 | COVA3-04 | Lambda | 10.1126/ science. abc5902 | 1.51 | 0.57 | >10 | NR | |
| 79 | COVA3-05 | Lambda | 10.1126/ science. abc5902 | 2.98 | 2.04 | >10 | NR | |
| 80 | COVA3-06 | Kappa | 10.1126/ science. abc5902 | 2.74 | 12.18 | >10 | NR | |
| 81 | COVA3-07 | Kappa | 10.1126/ science. abc5902 | 10.50 | 0.83 | >10 | NR | |
| 82 | COVA3-08 | Kappa | 10.1126/ science. abc5902 | 0.93 | 0.72 | >10 | NR | |
| 83 | COVA3-09 | Kappa | 10.1126/ science. abc5902 | 6.72 | 12.57 | >10 | NR | |
| 84 | COVA3-10 | Kappa | 10.1126/ science. abc5902 | 2.43 | 1.68 | >10 | NR | |

Notes:
NR indicates not reported
**= Not tested for competition with ACE2, but competes with Abs that compete with ACE2

TABLE 3

| ID | Reported Neutralization IC50 (µg/mL) | This Study Assembly Corrected p-value | This Study S trimer Binding Corrected p-value | Reported trimer Binding? | This Study Matches Literature? | This Study RBD Binding Corrected p-value | Reported RBD Binding? | This Study Matches Literature? | This Study ACE2 Competition Corrected p-value | Reported ACE2 Competition? | This Study Matches Literature? | Comments |
|---|---|---|---|---|---|---|---|---|---|---|---|---|
| COVA2-15 | 0.007584 | 0.00028100 | 9.9681E-06 | Yes | Yes | 0.0087938 | Yes | Yes | 2.648E-05 | Yes | Yes | |
| COVA1-18 | 0.00836667 | 3.16776E-05 | 2.0573E-09 | Yes | Yes | 3.835E-05 | Yes | Yes | 0.0001383 | Yes | Yes | |
| COVA2-07 | 0.029105 | 2.49482E-06 | 1.1935E-07 | Yes | Yes | 0.0003124 | Yes | Yes | 0.0051384 | Yes | Yes | |
| COVA2-39 | 0.036485 | 3.17346E-05 | 2.0958E-06 | Yes | Yes | 1.18E-07 | Yes | Yes | 0.0264003 | Yes | Yes | |
| COVA1-21 | 0.040085 | 0.000130605 | 0.70019587 | Yes | No | 0.1305754 | No | No | 0.7013239 | No | Yes | Note = 1 |
| COVA2-17 | 0.06255 | 2.82712E-07 | 0.04112962 | Yes | Yes | 0.5038236 | Yes | Yes | 0.7013239 | No | Yes | Note = 1 |
| COVA2-29 | 0.09225 | 1.5318E-08 | 0.57988764 | Yes | Yes | 0.7025922 | Yes | Yes | 0.8421427 | NR* | No | Note = 1 |
| COVA1-16 | 0.1305 | 4.54672E-07 | 0.00373049 | Yes | Yes | 7.205E-05 | Yes | Yes | 0.6785054 | Yes | No | Note = 2 |
| COVA1-22 | 0.17817 | 0.00426483 | 0.156391 | Yes | No | 0.7135031 | No | Yes | 0.9419785 | No | Yes | Note = 1 |
| COVA1-25 | 0.1797 | 1.00898E-08 | 0.98262611 | Yes | No | 0.6709869 | No | Yes | 0.5973437 | NR | NA | Note = 1 |
| COVA2-04 | 0.2164 | 9.20721E-05 | 1.1296E-05 | Yes | Yes | 7.495E-06 | Yes | No | 0.8198569 | NR | NA | Note = 3 |
| COVA1-03 | 0.42033333 | 2.04897E-08 | 0.70128698 | No | Yes | 0.5038236 | No | Yes | 0.7601306 | NR | Yes | Note = 3 |
| COVA2-20 | 0.728 | 0.000440231 | 0.00322935 | Yes | Yes | 0.49341 | Yes | No | 0.6603918 | NR | NA | |
| COVA1-12 | 1.257 | 4.81594E-06 | 0.10666569 | Yes | No | 0.9277872 | Yes | No | 0.791056 | NR | NA | Note = 3 |
| COVA2-02 | 3.1315 | 5.4370E-08 | 1.5244E-07 | Yes | Yes | 0.0039908 | Yes | Yes | 0.9795199 | NR | NA | Note = 3 |
| COVA2-13 | 3.16 | 1.01901E-05 | 0.49654254 | Yes | No | 0.7352781 | Yes | No | 0.0530739 | NR | NA | Note = 3 |
| COVA2-11 | 3.716 | 6.04069E-09 | 0.70039587 | Yes | Yes | 0.883416 | Yes | No | 0.641894 | NR | NA | Note = 3 |
| COVA2-37 | 3.986 | 3.6221E-05 | 3.2118E-05 | Yes | Yes | 0.4226117 | No | No | 0.9419785 | NR | NA | |
| COVA2-05 | 5.665 | 2.25579E-05 | 0.73322665 | Yes | No | 0.1575016 | No | No | 0.9795199 | NR | NA | Note = 3 |
| COVA1-01 | >10 | 0.023751117 | 0.67270205 | Yes | No | 0.6502224 | No | No | 0.4744563 | NR | NA | |
| COVA1-02 | >10 | 0.030295725 | 0.61661801 | Yes | No | 0.8883416 | No | No | 0.8023787 | NR | NA | |
| COVA1-04 | >10 | 4.65572E-06 | 0.35489958 | No | Yes | 0.4157211 | No | Yes | 0.2291667 | NR | NA | |
| COVA1-05 | >10 | 2.80696E-06 | 0.40955051 | No | Yes | 0.733907 | No | Yes | 0.641894 | NR | NA | |
| COVA1-06 | >10 | 9.49691E-08 | 0.66888494 | Yes | Yes | 0.9634157 | No | Yes | 0.6007699 | NR | NA | |
| COVA1-07 | >10 | 1.6274E-06 | 3.0005E-05 | Yes | Yes | 0.3601637 | Yes | No | 0.6603918 | NR | NA | |
| COVA1-08 | >10 | 0.0018942 | 0.66888494 | Yes | No | 0.7226069 | Yes | No | 0.2214738 | NR | NA | |
| COVA1-09 | >10 | 8.03287E-06 | 0.44206446 | Yes | No | 0.1347757 | No | No | 0.4506506 | NR | NA | |
| COVA1-10 | >10 | 3.26669E-06 | 0.09430764 | No | Yes | 0.3272524 | No | Yes | 0.8023787 | NR | NA | |
| COVA1-11 | >10 | 0.001796489 | 0.3189924 | No | Yes | 0.1424921 | No | Yes | 0.9824448 | NR | NA | |
| COVA1-13 | >10 | 1.49047E-07 | 0.50242069 | No | Yes | 0.1959743 | No | Yes | 0.4127182 | NR | NA | |
| COVA1-14 | >10 | 9.46278E-07 | 0.59554006 | No | Yes | 0.4601873 | No | Yes | 0.7634759 | NR | NA | |
| COVA1-15 | >10 | 0.000130505 | 0.78036474 | No | Yes | 0.9042547 | No | Yes | 0.8023787 | NR | NA | |
| COVA1-17 | >10 | 6.2215E-05 | 0.92204142 | No | Yes | 0.7541237 | No | Yes | 0.9823787 | NR | NA | |
| COVA1-19 | >10 | 5.02058E-06 | 0.93232201 | Yes | No | 0.4601873 | No | No | 0.742581 | NR | NA | |
| COVA1-20 | >10 | 0.001895968 | 0.40955051 | No | Yes | 0.3367792 | No | Yes | 0.8889737 | NR | NA | |
| COVA1-23 | >10 | 0.001427775 | 0.40955051 | No | Yes | 0.7025922 | No | Yes | 0.4506506 | NR | NA | |
| COVA1-24 | >10 | 0.82627416 | 0.67270205 | No | Yes | 0.9042547 | No | Yes | 0.8023787 | NR | NA | |
| COVA1-26 | >10 | 1.01373E-06 | 0.01925544 | Yes | Yes | 0.9567104 | No | Yes | 0.9824448 | NR | NA | |
| COVA1-27 | >10 | 5.23384E-05 | 0.74779504 | No | Yes | 0.1959743 | No | Yes | 0.9824448 | NR | NA | |
| COVA2-01 | >10 | 0.398216863 | 0.21544834 | No | Yes | 0.4601873 | No | No | 0.9795199 | NR | NA | |
| COVA2-03 | >10 | 6.64015E-07 | 0.18930499 | Yes | Yes | 0.7541237 | Yes | Yes | 0.7807363 | NR | NA | |
| COVA2-06 | >10 | 4.59534E-07 | 0.70019587 | No | Yes | 0.3308965 | No | Yes | 0.8465108 | NR | NA | |
| COVA2-08 | >10 | 1.47312E-07 | 0.30019587 | No | Yes | 0.9669323 | No | Yes | 0.5683376 | NR | NA | |
| COVA2-09 | >10 | 1.97303E-06 | 0.70019587 | No | Yes | 0.4781464 | No | Yes | 0.9419785 | NR | NA | |

TABLE 3-continued

| ID | Reported Neutralization IC50 (µg/mL) | This Study Assembly Corrected p-value | This Study S trimer Binding Corrected p-value | Reported trimer Binding? | This Study Matches Literature? | This Study RBD Binding Corrected p-value | Reported RBD Binding? | This Study Matches Literature? | This Study ACE2 Competition Corrected p-value | Reported ACE2 Competition? | This Study Matches Literature? | Comments |
|---|---|---|---|---|---|---|---|---|---|---|---|---|
| COVA2-10 | >10 | 8.64366E-06 | 0.0005217 | Yes | Yes | 0.9694728 | No | Yes | 0.934493 | NR | NA | |
| COVA2-12 | >10 | 4.69081E-08 | 0.17721693 | Yes | No | 0.85571 | No | Yes | 0.4506506 | NR | NA | |
| COVA2-14 | >10 | 9.02992E-11 | 0.00069711 | Yes | Yes | 0.9634157 | No | Yes | 0.0740219 | NR | NA | |
| COVA2-16 | >10 | 3.62085E-08 | 0.50342369 | Yes | Yes | 0.5308736 | Yes | No | 0.641894 | NR | NA | |
| COVA2-18 | >10 | 2.94367E-06 | 0.00609515 | Yes | Yes | 0.8883416 | No | Yes | 0.3282748 | NR | NA | |
| COVA2-19 | >10 | 8.5966E-05 | 0.93492874 | No | Yes | 0.5038236 | No | Yes | 0.742581 | NR | NA | |
| COVA2-21 | >10 | 6.6917E-05 | 0.70128698 | No | Yes | 0.5127105 | No | Yes | 0.742581 | NR | NA | |
| COVA2-22 | >10 | 0.000777572 | 0.52698032 | Yes | Yes | 0.6502224 | No | Yes | 0.7476862 | NR | NA | |
| COVA2-23 | >10 | 0.000581001 | 0.93111584 | Yes | No | 0.924694 | Yes | No | 0.7057069 | NR | NA | |
| COVA2-24 | >10 | 7.75659E-06 | 0.61480237 | Yes | No | 0.3703461 | Yes | No | 0.7013239 | NR | NA | |
| COVA2-25 | >10 | 5.02068E-06 | 0.00036725 | Yes | Yes | 0.9378977 | No | Yes | 0.9419785 | NR | NA | |
| COVA2-26 | >10 | 3.634E-06 | 0.1019982 | Yes | No | 0.6510618 | No | Yes | 0.51508061 | NR | NA | |
| COVA2-27 | >10 | 9.16728E-11 | 0.57988764 | No | Yes | 0.9518633 | Yes | No | 0.3362294 | NR | NA | |
| COVA2-28 | >10 | 2.89793E-06 | 3.0005E-05 | Yes | Yes | 0.4485305 | No | Yes | 0.8023787 | NR | NA | |
| COVA2-30 | >10 | 0.00085834 | 0.94182212 | Yes | No | 0.8883416 | Yes | No | 0.6295521 | NR | NA | |
| COVA2-31 | >10 | 0.001537683 | 0.54346823 | Yes | No | 0.4462176 | No | Yes | 0.83299924 | NR | NA | |
| COVA2-32 | >10 | 2.56213E-08 | 0.01934961 | Yes | No | 0.3343642 | No | Yes | 0.8023787 | NR | NA | |
| COVA2-33 | >10 | 0.000636819 | 0.07442085 | Yes | No | 0.995755 | No | Yes | 0.8402629 | NR | NA | |
| COVA2-34 | >10 | 9.46278E-07 | 1.0795E-06 | No | No | 0.995755 | No | Yes | 0.9592809 | NR | NA | |
| COVA2-35 | >10 | 9.65401E-06 | 0.07442085 | No | Yes | 0.7996307 | No | Yes | 0.8198569 | NR | NA | |
| COVA2-36 | >10 | 3.16776E-05 | 0.47440293 | No | Yes | 0.1424921 | Yes | No | 0.8889739 | NR | NA | |
| COVA2-38 | >10 | 4.220E-05 | 0.97972825 | Yes | No | 0.7316567 | No | Yes | 0.7476862 | NR | NA | |
| COVA2-40 | >10 | 5.23384E-05 | 0.54346823 | Yes | No | 0.9634157 | No | Yes | 0.8198569 | NR | NA | |
| COVA2-41 | >10 | 0.000154373 | 1.4239E-06 | No | Yes | 0.8883416 | No | Yes | 0.8012118 | NR | NA | |
| COVA2-42 | >10 | 0.002477681 | 0.07442085 | No | Yes | 0.4781464 | No | Yes | 0.5158061 | NR | NA | |
| COVA2-43 | >10 | 1.01967E-05 | 0.00277297 | Yes | Yes | 0.3703461 | No | Yes | 0.9090091 | NR | NA | |
| COVA2-44 | >10 | 0.00028819 | 0.43586181 | Yes | No | 0.5424126 | Yes | No | 0.9419785 | NR | NA | |
| COVA2-45 | >10 | 9.6446E-09 | 0.04816721 | No | No | 0.733907 | Yes | No | 0.1722297 | NR | NA | |
| COVA2-46 | >10 | 1.78904E-05 | 0.54346823 | Yes | No | 0.8562196 | No | Yes | 0.150915 | NR | NA | |
| COVA2-47 | >10 | 5.14795E-08 | 0.52706889 | Yes | No | 0.6510618 | Yes | Yes | 0.8421427 | NR | NA | |
| COVA3-01 | >10 | 7.97041E-06 | 0.67270205 | No | Yes | 0.4462176 | No | Yes | 0.5973437 | NR | NA | |
| COVA3-02 | >10 | 3.94985E-05 | 0.57988764 | No | Yes | 0.466945 | No | Yes | 0.8421427 | NR | NA | |
| COVA3-03 | >10 | 5.7884E-05 | 0.67270205 | Yes | No | 0.5038236 | No | Yes | 0.9824448 | NR | NA | |
| COVA3-04 | >10 | 0.000116546 | 0.67270205 | Yes | No | 0.941522 | No | Yes | 0.7601306 | NR | NA | |
| COVA3-05 | >10 | 1.94994E-06 | 0.44206446 | Yes | No | 0.3703461 | No | Yes | 0.9228251 | NR | NA | |
| COVA3-06 | >10 | 2.64334E-08 | 0.07307222 | Yes | No | 0.5038236 | Yes | No | 0.8023787 | NR | NA | |
| COVA3-07 | >10 | 2.62058E-10 | 0.07442085 | Yes | No | 0.7025922 | No | Yes | 0.7013239 | NR | NA | |
| COVA3-08 | >10 | 0.848445286 | 0.01569225 | No | Yes | 0.9166084 | No | Yes | 0.7013239 | NR | NA | |

TABLE 3-continued

| ID | Reported Neutralization IC50 (μg/mL) | This Study Assembly Corrected p-value | This Study S trimer Binding Corrected p-value | Reported trimer Binding? | This Study Matches Literature? | This Study RBD Binding Corrected p-value | Reported RBD Binding? | This Study Matches Literature? | This Study ACE2 Competition Corrected p-value | Reported ACE2 Competition? | This Study Matches Literature? | Comments |
|---|---|---|---|---|---|---|---|---|---|---|---|---|
| COVA3-09 | >10 | 0.828400924 | 0.67270205 | Yes | No | 0.8784197 | Yes | No | 0.8263912 | NR | NA | |
| COVA3-10 | >10 | 1.58686E−08 | 0.35489958 | Yes | No | 0.8883416 | Yes | No | 0.5973437 | NR | NA | |

Notes:
NR indicates not reported;
NA indicates not applicable
*See Table 1 for additional information
Data generated in this study are labeled with "this study"
Data or information from literature are labeled with "reported"
Note 1:
Insufficient affinity/concentration of sdFab to detect S trimer binding in screened conditions
Note 2:
Insufficient affinity/concentration of sdFab to outcompete ACE2 in screened conditions
Note 3:
Insufficient affinity/concentration of sdFab to detect RBD binding in screened conditions

REFERENCES

1. Koczula, K. M. & Gallotta, A. Lateral flow assays. *Essays in Biochemistry* 60, 111-120 (2016).
2. Lu, R.-M. et al. Development of therapeutic antibodies for the treatment of diseases. *Journal of Biomedical Science* 27, 1 (2020).
3. Mullard, A. 2020 FDA drug approvals. *Nature Reviews Drug Discovery* 20, 85-90 (2021).
4. FDA. Emergency Use Authorization for REGEN-COV (Casirivimab and Imdevimab). https://www.fda.gov/media/145610/download (2020).
5. FDA. Emergency Use Authorization for Bamlanivimab and Etesevimab. https://www.fda.gov/media/145801/download (2020).
6. FDA. Emergency Use Authorization for Sotrovimab. (2021).
7. Vazquez-Lombardi, R. et al. Transient expression of human antibodies in mammalian cells. *Nature Protocols* 13, 99-117 (2018).
8. Gieselmann, L. et al. Effective high-throughput isolation of fully human antibodies targeting infectious pathogens. *Nature Protocols* 16, 3639-3671 (2021).
9. Pinto, D. et al. Cross-neutralization of SARS-CoV-2 by a human monoclonal SARS-CoV antibody. *Nature* 583, 290-295 (2020).
10. Starr, T. N. et al. SARS-CoV-2 RBD antibodies that maximize breadth and resistance to escape. *Nature* 597, 97-102 (2021).
11. Copin, R. et al. The monoclonal antibody combination REGEN-COV protects against SARS-CoV-2 mutational escape in preclinical and human studies. *Cell* 184, 3949-3961.e11 (2021).
12. Baum, A. et al. Antibody cocktail to SARS-CoV-2 spike protein prevents rapid mutational escape seen with individual antibodies. *Science* 369, 1014-1018 (2020).
13. Liu, Z. et al. Identification of SARS-CoV-2 spike mutations that attenuate monoclonal and serum antibody neutralization. *Cell Host & Microbe* 29, 477-488.e4 (2021).
14. Corti, D., Purcell, L. A., Snell, G. & Veesler, D. Tackling COVID-19 with neutralizing monoclonal antibodies. *Cell* 184, 3086-3108 (2021).
15. Ojima-Kato, T., Nagai, S. & Nakano, H. Ecobody technology: rapid monoclonal antibody screening method from single B cells using cell-free protein synthesis for antigen-binding fragment formation. *Scientific Reports* 7, 13979 (2017).
16. Ojima-Kato, T. et al. 'Zipbody' leucine zipper-fused Fab in *E. coli* in vitro and in vivo expression systems. *Protein Engineering Design and Selection* 29, 149-157 (2016).
17. Ojima-Kato, T. et al. Rapid Generation of Monoclonal Antibodies from Single B Cells by Ecobody Technology. *Antibodies* 7, 38 (2018).
18. Murakami, S., Matsumoto, R. & Kanamori, T. Constructive approach for synthesis of a functional IgG using a reconstituted cell-free protein synthesis system. *Scientific Reports* 9, 671 (2019).
19. Martin, R. W. et al. Development of a CHO-Based Cell-Free Platform for Synthesis of Active Monoclonal Antibodies. *ACS Synthetic Biology* 6, 1370-1379 (2017).
20. Stech, M. & Kubick, S. Cell-Free Synthesis Meets Antibody Production: A Review. *Antibodies* 4, 12-33 (2015).
21. Cai, Q. et al. A simplified and robust protocol for immunoglobulin expression in *Escherichia coli* cell-free protein synthesis systems. *Biotechnology Progress* 31, 823-831 (2015).
22. Yasgar, A., Jadhav, A., Simeonov, A. & Coussens, N. P. AlphaScreen-Based Assays: Ultra-High-Throughput Screening for Small-Molecule Inhibitors of Challenging Enzymes and Protein-Protein Interactions. in *Methods in Molecular Biology* vol. 1439 77-98 (2016).
23. Brouwer, P. J. M. et al. Potent neutralizing antibodies from COVID-19 patients define multiple targets of vulnerability. *Science* 369, 643-650 (2020).
24. Barnes, C. O. et al. Structures of human antibodies bound to SARS-CoV-2 spike reveal common epitopes and recurrent features of antibodies. *Cell* 2020.05.28.121533 (2020) doi:10.1016/j.cell.2020.06.025.
25. Du, S. et al. Structurally Resolved SARS-CoV-2 Antibody Shows High Efficacy in Severely Infected Hamsters and Provides a Potent Cocktail Pairing Strategy. *Cell* 1-11 (2020) doi:10.1016/j.cell.2020.09.035.
26. Piccoli, L. et al. Mapping Neutralizing and Immunodominant Sites on the SARS-CoV-2 Spike Receptor-Binding Domain by Structure-Guided High-Resolution Serology. Cell 183, 1024-1042.e21 (2020).
27. Kreye, J. et al. A Therapeutic Non-self-reactive SARS-CoV-2 Antibody Protects from Lung Pathology in a COVID-19 Hamster Model. *Cell* 183, 1058-1069.e19 (2020).
28. Ju, B. et al. Human neutralizing antibodies elicited by SARS-CoV-2 infection. *Nature* 584, 115-119 (2020).
29. Shi, R. et al. A human neutralizing antibody targets the receptor-binding site of SARS-CoV-2. *Nature* 584, 120-124 (2020).
30. Liu, L. et al. Potent neutralizing antibodies against multiple epitopes on SARS-CoV-2 spike. *Nature* 584, 450-456 (2020).
31. Barnes, C. O. et al. SARS-CoV-2 neutralizing antibody structures inform therapeutic strategies. *Nature* 588, 682-687 (2020).
32. Yuan, M. et al. A highly conserved cryptic epitope in the receptor binding domains of SARS-CoV-2 and SARS-CoV. *Science* 368, 630-633 (2020).
33. Wu, Y. et al. A noncompeting pair of human neutralizing antibodies block COVID-19 virus binding to its receptor ACE2. *Science* 1278, eabc2241 (2020).
34. Cao, Y. et al. Potent Neutralizing Antibodies against SARS-CoV-2 Identified by High-Throughput Single-Cell Sequencing of Convalescent Patients' B Cells. *Cell* 182, 73-84.e16 (2020).
35. Chi, X. et al. A neutralizing human antibody binds to the N-terminal domain of the Spike protein of SARS-CoV-2. *Science* 369, 650-655 (2020).
36. Hansen, J. et al. Studies in humanized mice and convalescent humans yield a SARS-CoV-2 antibody cocktail. *Science* 0827, eabd0827 (2020).
37. Yuan, M. et al. Structural basis of a shared antibody response to SARS-CoV-2. *Science* 369, 1119-1123 (2020).
38. Tortorici, M. A. et al. Ultrapotent human antibodies protect against SARS-CoV-2 challenge via multiple mechanisms. *Science* 370, 950-957 (2020).
39. Ding, R. et al. Rapid isolation of antigen-specific B-cells using droplet microfluidics. *RSC Advances* 10, 27006-27013 (2020).
40. Sun, Z. Z., Yeung, E., Hayes, C. A., Noireaux, V. & Murray, R. M. Linear DNA for rapid prototyping of synthetic biological circuits in an *Escherichia coli* based TX-TL cell-free system. *ACS Synthetic Biology* 3, 387-397 (2014).

41. Ritz, D. et al. Conversion of a Peroxiredoxin into a Disulfide Reductase by a Triplet Repeat Expansion. *Science* 294, 158-160 (2001).

42. Kim, D.-M. & Swartz, J. R. Efficient production of a bioactive, multiple disulfide-bonded protein using modified extracts of *Escherichia coli*. *Biotechnology and Bioengineering* 85, 122-129 (2004).

43. Yin, G. & Swartz, J. R. Enhancing Multiple Disulfide Bonded Protein Folding in a Cell-Free System. *Biotechnology and Bioengineering* 86, 188-195 (2004).

44. Dopp, J. L. & Reuel, N. F. Simple, functional, inexpensive cell extract for in vitro prototyping of proteins with disulfide bonds. *Biochemical Engineering Journal* 164, 107790 (2020).

45. Groff, D. et al. Engineering toward a bacterial "endoplasmic reticulum" for the rapid expression of immunoglobulin proteins. *mAbs* 6, 671-678 (2014).

46. Ryabova, L. A., Desplancq, D., Spirin, A. S. & Pluckthun, A. Functional antibody production using cell-free translation: Effects of protein disulfide isomerase and chaperones. *Nature Biotechnology* 15, 79-84 (1997).

47. Carter, P. et al. Humanization of an anti-p185HER2 antibody for human cancer therapy. *Proceedings of the National Academy of Sciences* 89, 4285-4289 (1992).

48. Hanson, Q. M. et al. Targeting ACE2-RBD Interaction as a Platform for COVID-19 Therapeutics: Development and Drug-Repurposing Screen of an AlphaLISA Proximity Assay. *ACS Pharmacology & Translational Science* 3, 1352-1360 (2020).

49. Benjamini, Y. & Hochberg, Y. Controlling the False Discovery Rate: A Practical and Powerful Approach to Multiple Testing. *Journal of the Royal Statistical Society: Series B (Methodological)* 57, 289-300 (1995).

50. Greaney, A. J. et al. Comprehensive mapping of mutations in the SARS-CoV-2 receptor-binding domain that affect recognition by polyclonal human plasma antibodies. *Cell Host & Microbe* 29, 463-476.e6 (2021).

51. Tan, C. W. et al. A SARS-CoV-2 surrogate virus neutralization test based on antibody-mediated blockage of ACE2-spike protein-protein interaction. *Nature Biotechnology* 38, 1073-1078 (2020).

52. Wrobel, A. G. et al. Antibody-mediated disruption of the SARS-CoV-2 spike glycoprotein. *Nature Communications* 11, 5337 (2020).

53. Newton, P., Harrison, P. & Clulow, S. A novel method for determination of the affinity of protein: Protein interactions in homogeneous assays. *Journal of Biomolecular Screening* 13, 674-682 (2008).

54. Kightlinger, W. et al. Design of glycosylation sites by rapid synthesis and analysis of glycosyltransferases. *Nature Chemical Biology* 14, 627-635 (2018).

55. Ojima-Kato, T., Nagai, S. & Nakano, H. N-terminal SKIK peptide tag markedly improves expression of difficult-to-express proteins in *Escherichia coli* and *Saccharomyces cerevisiae*. *Journal of Bioscience and Bioengineering* 123, 540-546 (2017).

56. Gibson, D. et al. Enzymatic assembly of DNA molecules up to several hundred kilobases. *Nat Methods* 6, 343-345 (2009).

57. Rabe, B. A. & Cepko, C. A Simple Enhancement for Gibson Isothermal Assembly. 10-15 (2020).

58. Kwon, Y. C. & Jewett, M. C. High-throughput preparation methods of crude extract for robust cell-free protein synthesis. *Scientific Reports* 5, 1-8 (2015).

59. Chen, Z. et al. De novo design of protein logic gates. *Science* 368, 78-84 (2020).

60. Hunt, A. C. et al. Multivalent designed proteins protect against SARS-CoV-2 variants of concern. bioRxiv 2021.07.07.451375 (2021) doi:10.1101/2021.07.07.451375.

61. Silverman, A. D., Kelley-Loughnane, N., Lucks, J. B. & Jewett, M. C. Deconstructing Cell-Free Extract Preparation for in Vitro Activation of Transcriptional Genetic Circuitry. *ACS synthetic biology* 8, 403-414 (2019).

62. Matsuda, T., Watanabe, S. & Kigawa, T. Cell-free synthesis system suitable for disulfide-containing proteins. *Biochemical and Biophysical Research Communications* 431, 296-301 (2013).

63. Swartz, J. R., Jewett, M. C. & Woodrow, K. A. Cell-Free Protein Synthesis With Prokaryotic Combined Transcription-Translation. in *Recombinant Gene Expression: Reviews and Protocols* (eds. Balbás, P. & Lorence, A.) 169-182 (Humana Press, 2004). doi:10.1385/1-59259-774-2:169.

64. Bouvet, J.-P. Immunoglobulin Fab fragment-binding proteins. *International Journal of Immunopharmacology* 16, 419-424 (1994).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

All methods described herein can be performed in any suitable order unless otherwise indicated herein or otherwise clearly contradicted by context. The use of any and all examples provided herein, is intended merely to better illuminate the invention and does not pose a limitation on the scope of the invention unless otherwise claimed. No language in the specification should be construed as indicating any non-claimed element as essential to the practice of the invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

The methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

We claim:

1. A method comprising:
   a) assembling a linear expression template (LET) from nucleic acid sequences, wherein assembling does not include the use of cells or cell culture; and wherein assembling comprises Golden Gate assembly or Gibson assembly;
   b) amplifying the LET to generate amplification products;
   c) contacting the amplification products of (b) with a cell-free protein expression system (CFPS) to produce protein products;
   d) characterizing the protein products of (c), wherein characterization comprises Amplified Luminescent Proximity Homogeneous Linked Immunosorbent Assay (AlphaLISA).

2. The method of claim 1, wherein the CFPS comprises an *Escherichia coli* (*E. coli*) extract.

3. The method of claim 2, wherein the *E. coli* comprises a mutation in the trxB and gor *E. coli* reductase genes.

4. The method of claim 1, wherein the nucleic acid sequences of step (a) comprise one or more of:
   (i) double-stranded linear DNA encoding a variable heavy (VH) chain sequence of a target antibody;
   (ii) double-stranded linear DNA encoding a variable light (VL) chain sequence of a target antibody;
   (iii) double-stranded linear DNA encoding a heavy chain constant (CH1) domain of a target antibody;
   (iv) double-stranded linear DNA encoding a light chain constant (CL) domain of a target antibody;
   (v) double-stranded linear DNA comprising an expression vector backbone or fragments thereof.

5. The method of claim 4, wherein the expression vector of (v) comprises a prokaryotic expression vector.

6. The method of claim 4, wherein the protein products of (c) comprise antigen-binding proteins.

7. The method of claim 6, wherein the antigen binding proteins comprise one or more of a full-length antibody, a Fab, and a scFV.

8. The method of claim 7, wherein the Fab comprises a sdFab.

9. The method of claim 1, wherein the AlphaLISA assay comprises donor and acceptor beads, wherein the donor beads comprise a first antigen, and wherein the acceptor beads comprise a second antigen, and wherein the protein products of (c) comprise antigen-binding proteins.

10. The method of claim 9, wherein the first and second antigens comprise the same protein.

11. The method of claim 9, wherein the first and second antigens comprise different proteins.

12. The method of claim 9, wherein the nucleic acid sequences of step (a) comprises:
   (i) double-stranded linear DNA coding for variable heavy (VH) chain domain of a target antibody and a double-stranded linear DNA coding for heavy chain constant (CH1) domain of the target antibody; or
   (ii) double-stranded linear DNA coding for variable light (VL) chain sequences of the target antibody and double-stranded linear DNA coding for light chain constant (CL) domain of the target antibody.

13. The method of claim 4, wherein the nucleic acid sequences of step (a) are from a B-cell isolated from an immunized animal.

14. The method of claim 4, wherein the nucleic acid sequences of step (a) are amplified via PCR from single cells after FACS sorting.

15. The method of claim 4, wherein the nucleic acid sequences of step (a) are identified via in vitro selection and individual sequences are recovered after cloning and transformation of the selected sequences.

16. The method of claim 4 wherein the nucleic acid sequences of step (a) are identified via in vitro selection and individual sequences are identified via DNA sequencing.

17. The method of claim 4 wherein the nucleic acid sequences of step (a) are identified via computational methods for predicting protein structure and function.

18. The method of claim 4 wherein the nucleic acids of step (a) are produced via DNA synthesis.

19. The method of claim 1, wherein the AlphaLISA assay comprises donor beads and acceptor beads, wherein the donor beads comprise a first protein product of step (c), wherein the first protein product of (c) comprises a VL domain and a CL domain of a target antibody; and wherein the acceptor beads comprises a second protein product of step (c), wherein the second protein product of (c) comprises a VH and a CH1 of the target antibody.

20. The method of claim 19, wherein the AlphaLISA further comprises an antigen that binds the target antibody.

* * * * *